United States Patent
Malona et al.

(10) Patent No.: US 11,230,551 B2
(45) Date of Patent: Jan. 25, 2022

(54) DEUTERATED ANALOGS OF MK2 INHIBITORS AND USES THEREOF

(71) Applicant: Celgene CAR LLC, Pembroke (BM)

(72) Inventors: John Malona, Brookline, MA (US); Sekhar S. Surapaneni, Warren, NJ (US)

(73) Assignee: Celgene CAR LLC, Pembroke (BM)

( * ) Notice: Subject to any disclaimer, the term of this patent is extended or adjusted under 35 U.S.C. 154(b) by 0 days.

(21) Appl. No.: 16/494,711

(22) PCT Filed: Mar. 15, 2018

(86) PCT No.: PCT/US2018/022545
§ 371 (c)(1),
(2) Date: Sep. 16, 2019

(87) PCT Pub. No.: WO2018/170201
PCT Pub. Date: Sep. 20, 2018

(65) Prior Publication Data
US 2021/0122762 A1    Apr. 29, 2021

Related U.S. Application Data

(60) Provisional application No. 62/472,022, filed on Mar. 16, 2017.

(51) Int. Cl.
*C07D 495/14* (2006.01)

(52) U.S. Cl.
CPC ........ *C07D 495/14* (2013.01); *C07B 2200/05* (2013.01)

(58) Field of Classification Search
CPC .......................... C07D 495/14; C07B 2200/05
USPC ....................................................... 514/219
See application file for complete search history.

(56) References Cited

U.S. PATENT DOCUMENTS

| | | | |
|---|---|---|---|
| 7,517,990 B2 * | 4/2009 | Ito | C07D 213/16 546/184 |
| 7,838,674 B2 | 11/2010 | Schlapbach et al. | |
| 9,458,175 B2 | 10/2016 | Alexander et al. | |
| 9,790,235 B2 | 10/2017 | Alexander et al. | |
| 10,138,256 B2 | 11/2018 | Alexander et al. | |
| 10,253,040 B1 | 4/2019 | Alexander et al. | |
| 10,577,380 B2 | 3/2020 | Alexander et al. | |
| 10,882,867 B2 | 1/2021 | Han et al. | |
| 10,894,796 B2 | 1/2021 | Feigelson et al. | |
| 2012/0022030 A1 | 1/2012 | Schlapbach et al. | |
| 2013/0137708 A1 | 5/2013 | Garske et al. | |
| 2014/0018343 A1 | 1/2014 | Romero et al. | |
| 2019/0375762 A1 | 12/2019 | Alexander et al. | |
| 2020/0102325 A1 | 4/2020 | Guo et al. | |
| 2020/0102326 A1 | 4/2020 | Feigelson et al. | |
| 2020/0102327 A1 | 4/2020 | Malona et al. | |
| 2020/0148701 A1 | 5/2020 | Han et al. | |
| 2021/0053984 A1 | 2/2021 | Alexander et al. | |
| 2021/0139501 A1 | 5/2021 | Feigelson et al. | |
| 2021/0198276 A1 | 7/2021 | Han et al. | |

FOREIGN PATENT DOCUMENTS

| | | |
|---|---|---|
| WO | WO-1995/26325 A2 | 10/1995 |
| WO | WO-2004/058762 A1 | 7/2004 |
| WO | WO-2005/105814 A1 | 11/2005 |
| WO | WO-2009/010488 A1 | 1/2009 |
| WO | WO-2014/149164 A1 | 9/2014 |
| WO | WO-2016/044463 A2 | 3/2016 |
| WO | WO-2018/170199 A1 | 9/2018 |
| WO | WO-2018/170200 A1 | 9/2018 |
| WO | WO-2018/170201 A1 | 9/2018 |
| WO | WO-2018/170203 A1 | 9/2018 |
| WO | WO-2018/170204 A1 | 9/2018 |

OTHER PUBLICATIONS

Dumont, P., Perspective in the use of deuterated molecules as therapeutic agents, Revue IRE Tijdschrift, 6:2-10 (1982).
Foster, A. B., Deuterium Isotope Effects in the Metabolism of Drugs and Xenobiotics: Implications for Drug Design, Advances in Drug Research, 14:1-40 (1985).
O'Driscoll, C., Heavyweight drugs, Chem. & Industry, 24-26 (2009).
Tung, R. et al., The Development of Deuterium-Containing Drugs, Innovations in Pharmaceutical Technology, 32:24-26 (2010).
International Search Report for PCT/US2015/050495, 2 pages (dated Dec. 11, 2015).
International Search Report for PCT/US2018/022545, 3 pages (dated Apr. 27, 2018).

\* cited by examiner

*Primary Examiner* — Kristin A Vajda
(74) *Attorney, Agent, or Firm* — Choate, Hall & Stewart LLP; Kristen C. Buteau; Nicholas J. Pace

(57) ABSTRACT

The present invention provides compounds, pharmaceutically acceptable compositions thereof, and methods of using the same.

13 Claims, No Drawings

DEUTERATED ANALOGS OF MK2 INHIBITORS AND USES THEREOF

CROSS-REFERENCE TO RELATED APPLICATIONS

The present application claims priority to U.S. Provisional Patent Application No. 62/472,022, filed on Mar. 16, 2017, the entirety of which is hereby incorporated by reference.

TECHNICAL FIELD OF THE INVENTION

The present invention relates to compounds useful as inhibitors of MK2 kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNF-α), interleukin 6 (IL-6) and interferon gamma (IFNγ), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α. (see Deak et al., EMBO. 17:4426-4441 (1998); Shi et al., Biol. Chem. 383:1519-1536 (2002); Staklatvala., Curr. Opin. Pharmacol. 4:372-377 (2004), and Shiroto et al., J. Mol. Cardiol. 38:93-97 (2005)).

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of the present invention, and pharmaceutically acceptable compositions thereof, are effective as inhibitors of MK2. Such compounds have general Formula I:

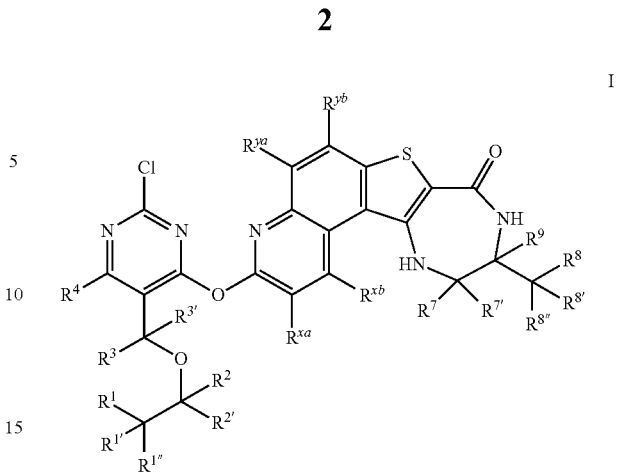

or a pharmaceutically acceptable salt thereof, wherein each of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is as defined herein.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

1. General Description of Certain Aspects of the Invention

In certain embodiments, the present invention provides irreversible inhibitors of MK2. In some embodiments, such compounds include those of the formulae described herein, or a pharmaceutically acceptable salt thereof, wherein each variable is as defined and described herein. Such compounds have the structure of Formula I:

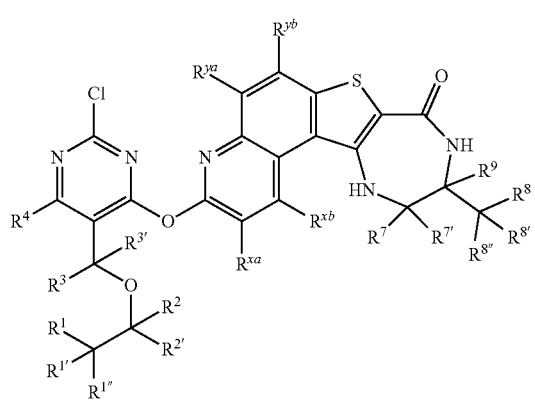

or a pharmaceutically acceptable salt thereof, wherein:
 each of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is independently selected from hydrogen or deuterium;

provided that at least one of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is deuterium.

In some embodiments, the compound of Formula I is a compound other than

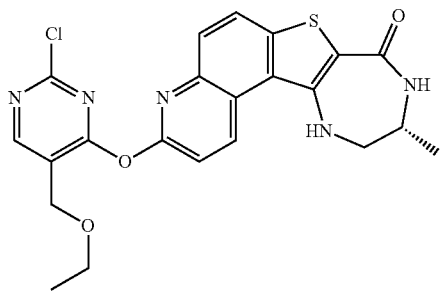

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof. Inhibition of activity of a protein kinase, for example, MK2 or a mutant thereof, in a biological sample is useful for a variety of purposes that are known to one of skill in the art. Examples of such purposes include, but are not limited to, blood transfusion, organ transplantation, biological specimen storage, and biological assays.

As used herein, a "disease or disorder associated with MK2" or, alternatively, "an MK2-mediated disease or disorder" means any disease or other deleterious condition in which MK2, or a mutant thereof, is known or suspected to play a role.

The term "subject", as used herein, means a mammal and includes human and animal subjects, such as domestic animals (e.g., horses, dogs, cats, etc.). The terms "subject" and "patient" are used interchangeably. In some embodiments, the "patient" or "subject" means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The amount of compounds of the present invention that may be combined with the carrier materials to produce a composition in a single dosage form will vary depending upon the host treated, the particular mode of administration, etc. Preferably, provided compositions are formulated so that a dosage of between 0.01 to about 100 mg/kg, or about 0.1 mg/kg to about 50 mg/kg, and preferably from about 1 mg/kg to about 25 mg/kg, of subject body weight/day of the inhibitor can be administered to a patient receiving these compositions to obtain the desired therapeutic effect. The amount of a compound of the present invention in the composition will also depend upon the particular compound in the composition.

The expression "unit dosage form" as used herein refers to a physically discrete unit of a provided compound and/or compositions thereof appropriate for the subject to be treated. It will be understood, however, that the total daily usage of the active agent (i.e., compounds and compositions of the present invention) will be decided by the attending physician within the scope of sound medical judgment. The specific effective dose level for any particular subject (i.e., patient) or organism will depend upon a variety of factors including the disorder being treated and the severity of the disorder; activity of specific active agent employed; specific composition employed; age, body weight, general health, sex and diet of the subject; time of administration, route of administration, and rate of excretion of the specific active agent employed; duration of the treatment; and like factors well known in the medical arts.

The term "parenteral" as used herein includes subcutaneous, intravenous, intramuscular, intra-articular, intra-synovial, intrasternal, intrathecal, intrahepatic, intralesional and intracranial injection or infusion techniques.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a provided compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a "therapeutically effective amount" is at least a minimal amount of a provided compound, or composition containing a provided compound, which is sufficient for treating one or more symptoms of an MK2-mediated disease or disorder.

As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

As used herein, the term "inhibitor" is defined as a compound that binds to and/or inhibits the target protein kinase, MK2, with measurable affinity. In certain embodiments, an inhibitor has an $IC_{50}$ and/or binding constant of less than about 50 µM, less than about 1 µM, less than about 500 nM, less than about 100 nM, or less than about 10 nM.

The terms "measurable affinity" and "measurably inhibit," as used herein, means a measurable change in MK2 activity between a sample comprising a compound of the present invention, or composition thereof, and MK2, and an equivalent sample comprising MK2, in the absence of said compound, or composition thereof.

As used herein, the term "irreversible" or "irreversible inhibitor" refers to an inhibitor (i.e. a compound) that is able to be covalently bonded to a kinase in a substantially non-reversible manner. That is, whereas a reversible inhibitor is able to bind to (but is generally unable to form a covalent bond with) a kinase, and therefore can become dissociated from the kinase, an irreversible inhibitor will remain substantially bound to a kinase once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to a kinase once covalent bond formation has occurred and will remain bound for a time period that is longer than the life of the protein.

Methods for identifying if a compound is an irreversible inhibitor are known to one of ordinary skill in the art. Such methods include, but are not limited to, enzyme kinetic analysis of the inhibition profile of the compound with a kinase, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

As used herein, the term "drug resistance" refers to changes in the wild-type nucleic acid sequence coding a target protein, and/or the amino acid sequence of the target protein, and/or the amino acid sequence of another protein, which changes or decreases or abolishes the inhibitory effect of the inhibitor on the target protein. Without wishing to be bound by any particular theory, it is believed that certain compounds of the present invention, i.e., compounds that are irreversible kinase inhibitors, may be effective inhibitors of drug resistant forms of protein kinases.

3. Description of Exemplary Compounds

According to one aspect, the present invention provides a compound of Formula I:

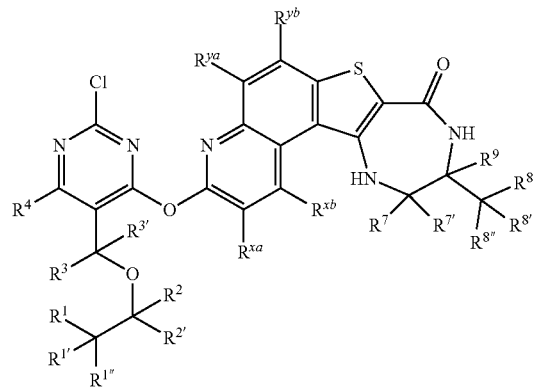

I or a pharmaceutically acceptable salt thereof, wherein:
each of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is independently selected from hydrogen or deuterium;
provided that at least one of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is deuterium.

Deuterium (D or $^2H$) is a stable, non-radioactive isotope of hydrogen and has an atomic weight of 2.0144. Hydrogen naturally occurs as a mixture of the isotopes $^1H$ (hydrogen or protium), D (2H or deuterium), and T ($^3H$ or tritium). It will be appreciated that the designation "hydrogen" in hydrogen-containing chemical compounds actually represents a mixture of hydrogen and about 0.015% deuterium.

Complete deuteration, or 100% deuteration, at any one site can be difficult to achieve in the laboratory. When a deuterium atom is indicated at a given site on any compound described herein, it is understood that a small percentage of hydrogen may still be present. Such compounds are said to be enriched with deuterium. Deuterium-enriched compounds are prepared via synthesis utilizing appropriately enriched starting materials. As used herein, the terms "deuterium-enriched" or "deuterium enrichment" refer to a compound, or a particular site of said compound, which comprises deuterium in an amount that is greater than its natural isotopic abundance (0.015%). Accordingly, in some embodiments, the present invention provides compounds comprising deuterium at a given site, wherein the percentage or level of deuterium incorporation is greater than its natural isotopic abundance.

In some embodiments, the present invention provides a compound of Formulae I' or I":

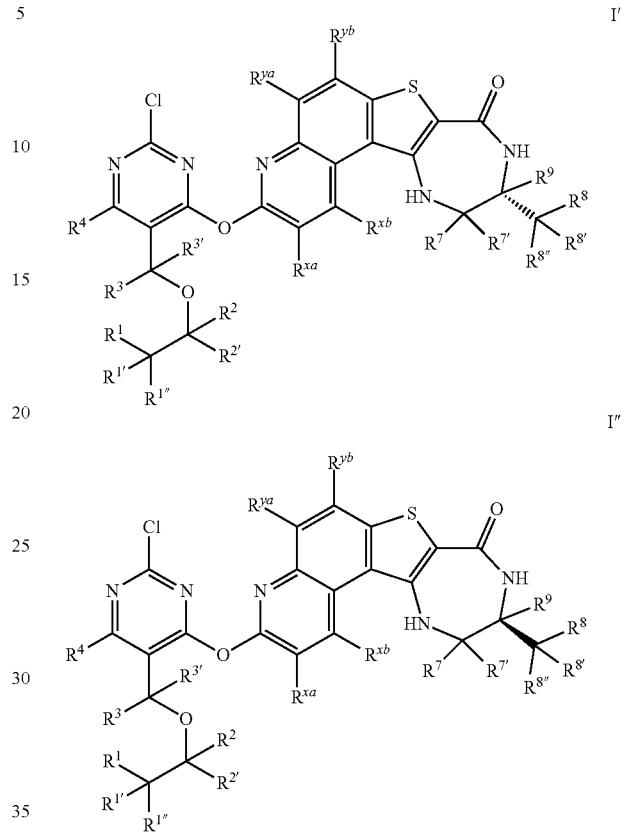

or a pharmaceutically acceptable salt thereof, wherein each of $R^1$, $R^{1'}$, $R^{1''}$, $R^2$, $R^{2'}$, $R^3$, $R^{3'}$, $R^4$, $R^7$, $R^{7'}$, $R^8$, $R^{8''}$, $R^9$, $R^{xa}$, $R^{xb}$, $R^{ya}$, and $R^{yb}$ is as defined herein.

In some embodiments, $R^1$ is hydrogen. In some embodiments, $R^1$ is deuterium. In some embodiments, $R^{1'}$ is hydrogen. In some embodiments, $R^{1'}$ is deuterium. In some embodiments, $R^{1''}$ is hydrogen. In some embodiments, $R^{1''}$ is deuterium.

In some embodiments, $R^1$, $R^{1'}$, and $R^{1''}$ are different. In some embodiments, each of $R^1$ and $R^{1'}$ is hydrogen and $R^{1''}$ is deuterium. In some embodiments, each of $R^1$ and $R^{1''}$ is hydrogen and $R^{1'}$ is deuterium. In some embodiments, each of $R^{1'}$ and $R^{1''}$ is hydrogen and $R^1$ is deuterium. In some embodiments, $R^1$ is hydrogen and each of $R^{1'}$ and $R^{1''}$ is deuterium. In some embodiments, $R^{1'}$ is hydrogen and each of $R^1$ and $R^{1''}$ is deuterium. In some embodiments, $R^{1''}$ is hydrogen and each of $R^1$ and $R^{1'}$ is deuterium.

In some embodiments, $R^1$, $R^{1'}$, and $R^{1''}$ are the same. In some embodiments, each of $R^1$, $R^{1'}$, and $R^{1''}$ is deuterium. In some embodiments, each of $R^1$, $R^{1'}$, and $R^{1''}$ is deuterium and each of $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is hydrogen. In some embodiments, each of $R^1$, $R^{1'}$, and $R^{1''}$ is deuterium and at least one of $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is deuterium. In some embodiments, each of $R^1$, $R^{1'}$, and $R^{1''}$ is hydrogen.

In some embodiments, $R^2$ is hydrogen. In some embodiments, $R^2$ is deuterium. In some embodiments, $R^{2'}$ is hydrogen. In some embodiments, $R^{2'}$ is deuterium.

In some embodiments, $R^2$ and $R^{2'}$ are different. In some embodiments, $R^2$ is hydrogen and $R^{2'}$ is deuterium. In some embodiments, $R^2$ is deuterium and $R^{2'}$ is hydrogen.

In some embodiments, $R^2$ and $R^{2'}$ are the same. In some embodiments, each of $R^2$ and $R^{2'}$ is deuterium. In some embodiments, each of $R^2$ and $R^{2'}$ is deuterium and each of $R^1$, $R^{1'}$, $R^{1''}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is hydrogen. In some embodiments, each of $R^2$ and $R^{2'}$ is deuterium and at least one of $R^1$, $R^{1'}$, $R^{1''}$, $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is deuterium. In some embodiments, each of $R^2$ and $R^{2'}$ is hydrogen.

In some embodiments, $R^3$ is hydrogen. In some embodiments, $R^3$ is deuterium. In some embodiments, $R^{3'}$ is hydrogen. In some embodiments, $R^{3'}$ is deuterium.

In some embodiments, $R^3$ and $R^{3'}$ are different. In some embodiments, $R^3$ is hydrogen and $R^{3'}$ is deuterium. In some embodiments, $R^3$ is deuterium and $R^{3'}$ is hydrogen.

In some embodiments, $R^3$ and $R^{3'}$ are the same. In some embodiments, each of $R^3$ and $R^{3'}$ is deuterium. In some embodiments, each of $R^3$ and $R^{3'}$ is deuterium and each of $R^1$, $R^{1'}$, $R^{1''}$, $R^2$, $R^{2'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is hydrogen. In some embodiments, each of $R^3$ and $R^{3'}$ is deuterium and at least one of $R^1$, $R^{1'}$, $R^{1''}$, $R^2$, $R^{2'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is deuterium. In some embodiments, each of $R^3$ and $R^{3'}$ is hydrogen.

In some embodiments, $R^4$ is hydrogen. In some embodiments, $R^4$ is deuterium. In some embodiments, $R^4$ is deuterium and each of $R^1$, $R^{1'}$, $R^{1''}$, $R^2$, $R^{2'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is hydrogen. In some embodiments, $R^4$ is deuterium and at least one of $R^1$, $R^{1'}$, $R^{1''}$, $R^2$, $R^{2'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is deuterium.

In some embodiments, $R^7$ is hydrogen. In some embodiments, $R^7$ is deuterium. In some embodiments, $R^{7'}$ is hydrogen. In some embodiments, $R^{7'}$ is deuterium.

In some embodiments, $R^7$ and $R^{7'}$ are different. In some embodiments, $R^7$ is hydrogen and $R^{7'}$ is deuterium. In some embodiments, $R^7$ is deuterium and $R^{7'}$ is hydrogen.

In some embodiments, $R^7$ and $R^{7'}$ are the same. In some embodiments, each of $R^7$ and $R^{7'}$ is deuterium. In some embodiments, each of $R^7$ and $R^{7'}$ is deuterium and each of $R^1$, $R^{1'}$, $R^{1''}$, $R^2$, $R^{2'}$, $R^3$, $R^{3'}$, $R^4$, $R^8$, $R^{8'}$, $R^{8''}$, $R^9$, $R^{xa}$, $R^{xb}$, $R^{ya}$, and $R^{yb}$ is hydrogen. In some embodiments, each of $R^7$ and $R^{7'}$ is deuterium and at least one of $R^1$, $R^{1'}$, $R^{1''}$, $R^2$, $R^{2'}$, $R^3$, $R^{3'}$, $R^4$, $R^8$, $R^{8'}$, $R^{8''}$, $R^9$, $R^{xa}$, $R^{xb}$, $R^{ya}$, and $R^{yb}$ is deuterium. In some embodiments, each of $R^7$ and $R^{7'}$ is hydrogen.

In some embodiments, $R^8$ is hydrogen. In some embodiments, $R^8$ is deuterium. In some embodiments, $R^{8'}$ is hydrogen. In some embodiments, $R^{8'}$ is deuterium. In some embodiments, $R^{8''}$ is hydrogen. In some embodiments, $R^{8''}$ is deuterium.

In some embodiments, $R^8$, $R^{8'}$, and $R^{8''}$ are different. In some embodiments, each of $R^8$ and $R^{8'}$ is hydrogen and $R^{8''}$ is deuterium. In some embodiments, each of $R^8$ and $R^{8''}$ is hydrogen and $R^{8'}$ is deuterium. In some embodiments, each of $R^{8'}$ and $R^{8''}$ is hydrogen and $R^8$ is deuterium. In some embodiments, $R^8$ is hydrogen and each of $R^{8'}$ and $R^{8''}$ is deuterium. In some embodiments, $R^{8'}$ is hydrogen and each of $R^8$ and $R^{8''}$ is deuterium. In some embodiments, $R^{8''}$ is hydrogen and each of $R^8$ and $R^{8'}$ is deuterium.

In some embodiments, $R^8$, $R^{8'}$, and $R^{8''}$ are the same. In some embodiments, each of $R^8$, $R^{8'}$, and $R^{8''}$ is deuterium. In some embodiments, each of $R^8$, $R^{8'}$, and $R^{8''}$ is deuterium and each of $R^1$, $R^{1'}$, $R^{1''}$, $R^2$, $R^{2'}$, $R^3$, $R^{3'}$, $R^4$, $R^7$, $R^{7'}$, $R^9$, $R^{xa}$, $R^{xb}$, $R^{ya}$, and $R^{yb}$ is hydrogen. In some embodiments, each of $R^8$, $R^{8'}$, and $R^{8''}$ is deuterium and at least one of $R^1$, $R^{1'}$, $R^{1''}$, $R^2$, $R^{2'}$, $R^3$, $R^{3'}$, $R^4$, $R^7$, $R^{7'}$, $R^9$, $R^{xa}$, $R^{xb}$, $R^{ya}$, and $R^{yb}$ is deuterium. In some embodiments, each of $R^8$, $R^{8'}$, and $R^{8''}$ is hydrogen.

In some embodiments, $R^9$ is hydrogen. In some embodiments, $R^9$ is deuterium. In some embodiments, $R^9$ is deuterium and each of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^{xa}$, $R^{xb}$, $R^{ya}$, and $R^{yb}$ is hydrogen. In some embodiments, $R^9$ is deuterium and at least one of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^{xa}$, $R^{xb}$, $R^{ya}$, and $R^{yb}$ is deuterium.

In some embodiments, $R^{xa}$ is hydrogen. In some embodiments, $R^{xa}$ is deuterium. In some embodiments, $R^{xb}$ is hydrogen. In some embodiments, $R^{xb}$ is deuterium.

In some embodiments, $R^{xa}$ and $R^{xb}$ are different. In some embodiments, $R^{xa}$ is hydrogen and $R^{xb}$ is deuterium. In some embodiments, $R^{xa}$ is deuterium and $R^{xb}$ is hydrogen.

In some embodiments, $R^{xa}$ and $R^{xb}$ are the same. In some embodiments, each of $R^{xa}$ and $R^{xb}$ is deuterium. In some embodiments, each of $R^{xa}$ and $R^{xb}$ is deuterium and each of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{ya}$, and $R^{yb}$ is hydrogen. In some embodiments, each of $R^{xa}$ and $R^{xb}$ is deuterium and at least one of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{ya}$, and $R^{yb}$ is deuterium. In some embodiments, each of $R^{xa}$ and $R^{xb}$ is hydrogen.

In some embodiments, $R^{ya}$ is hydrogen. In some embodiments, $R^{ya}$ is deuterium. In some embodiments, $R^{yb}$ is hydrogen. In some embodiments, $R^{yb}$ is deuterium.

In some embodiments, $R^{ya}$ and $R^{yb}$ are different. In some embodiments, $R^{ya}$ is hydrogen and $R^{yb}$ is deuterium. In some embodiments, $R^{ya}$ is deuterium and $R^{yb}$ is hydrogen.

In some embodiments, $R^{ya}$ and $R^{yb}$ are the same. In some embodiments, each of $R^{ya}$ and $R^{yb}$ is deuterium. In some embodiments, each of $R^{ya}$ and $R^{yb}$ is deuterium and each of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, and $R^{xb}$ is hydrogen. In some embodiments, each of $R^{ya}$ and $R^{yb}$ is deuterium and at least one of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, $R^9$, $R^{xa}$, and $R^{xb}$ is deuterium. In some embodiments, each of $R^{ya}$ and $R^{yb}$ is hydrogen.

In some embodiments, each of $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is deuterium. In some embodiments, each of $R^3$, $R^{3'}$, $R^4$, $R^7$, $R^{7'}$, $R^8$, $R^{8'}$, $R^{8''}$, $R^9$, $R^{xa}$, $R^{xb}$, $R^{ya}$, and $R^{yb}$ is hydrogen. Accordingly, in some embodiments, the present invention provides a compound of Formulae II, II' or II'':

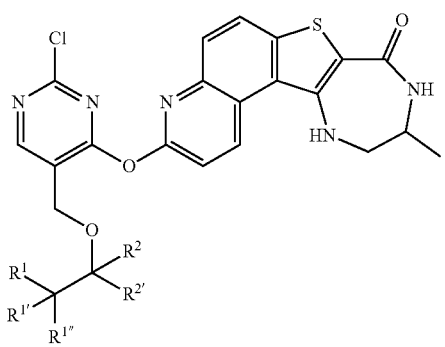

-continued

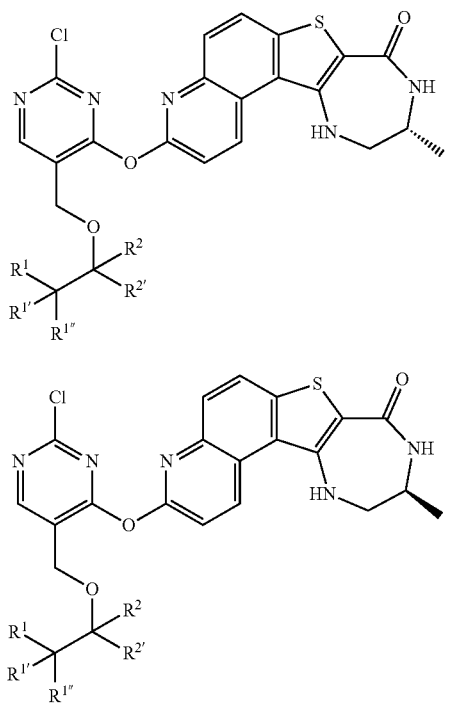

or a pharmaceutically acceptable salt thereof, wherein each of $R^1$, $R^{1'}$, $R^{1''}$, $R^2$, and $R^{2'}$ is as defined above and described herein, provided that at least one of $R^1$, $R^{1'}$, $R^{1''}$, $R^2$, and $R^{2'}$ is deuterium.

In some embodiments, a compound of Formulae II, II' or II'' is selected from the compounds in Table 1.

TABLE 1

Compounds of Formulae II, II' or II''.

| Formula II | Formula II' | Formula II'' | $R^1$ | $R^{1'}$ | $R^{1''}$ | $R^2$ | $R^{2'}$ |
|---|---|---|---|---|---|---|---|
| II-1 | II'-1 | II''-1 | D | H | H | H | H |
| II-2 | II'-2 | II''-2 | H | D | H | H | H |
| II-3 | II'-3 | II''-3 | H | H | D | H | H |
| II-4 | II'-4 | II''-4 | D | D | H | H | H |
| II-5 | II'-5 | II''-5 | D | H | D | H | H |
| II-6 | II'-6 | II''-6 | H | D | D | H | H |
| II-7 | II'-7 | II''-7 | D | D | D | H | H |
| II-8 | II'-8 | II''-8 | H | H | H | H | D |
| II-9 | II'-9 | II''-9 | D | H | H | H | D |
| II-10 | II'-10 | II''-10 | H | D | H | H | D |
| II-11 | II'-11 | II''-11 | H | H | D | H | D |
| II-12 | II'-12 | II''-12 | D | D | H | H | D |
| II-13 | II'-13 | II''-13 | D | H | D | H | D |
| II-14 | II'-14 | II''-14 | H | D | D | H | D |
| II-15 | II'-15 | II''-15 | D | D | D | H | D |
| II-16 | II'-16 | II''-16 | H | H | H | D | H |
| II-17 | II'-17 | II''-17 | D | H | H | D | H |
| II-18 | II'-18 | II''-18 | H | D | H | D | H |
| II-19 | II'-19 | II''-19 | H | H | D | D | H |
| II-20 | II'-20 | II''-20 | D | D | H | D | H |
| II-21 | II'-21 | II''-21 | D | H | D | D | H |
| II-22 | II'-22 | II''-22 | H | D | D | D | H |
| II-23 | II'-23 | II''-23 | D | D | D | D | H |
| II-24 | II'-24 | II''-24 | H | H | H | D | D |
| II-25 | II'-25 | II''-25 | D | H | H | D | D |
| II-26 | II'-26 | II''-26 | H | D | H | D | D |
| II-27 | II'-27 | II''-27 | H | H | D | D | D |
| II-28 | II'-28 | II''-28 | D | D | H | D | D |
| II-29 | II'-29 | II''-29 | D | H | D | D | D |
| II-30 | II'-30 | II''-30 | H | D | D | D | D |
| II-31 | II'-31 | II''-31 | D | D | D | D | D |

In some embodiments, each of $R^7$, $R^{7'}$, $R^8$, $R^{8'}$, $R^{8''}$, $R^9$, $R^{xa}$, $R^{xb}$, $R^{ya}$, and $R^{yb}$ is deuterium. In some embodiments, each of $R^7$, $R^{7'}$, $R^8$, $R^{8'}$, $R^{8''}$, $R^9$, $R^{xa}$, $R^{xb}$, $R^{ya}$, and $R^{yb}$ is hydrogen. Accordingly, in some embodiments, the present invention provides a compound of Formulae III, III' or III'':

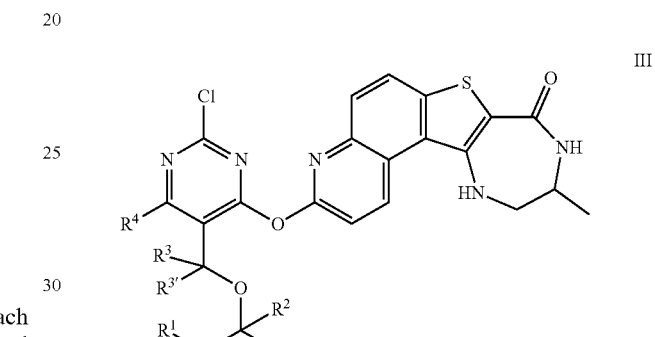

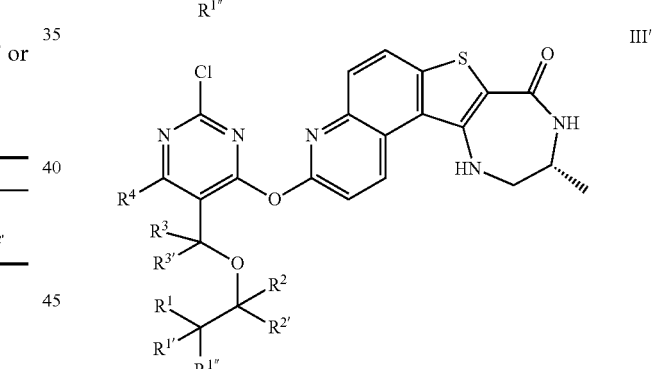

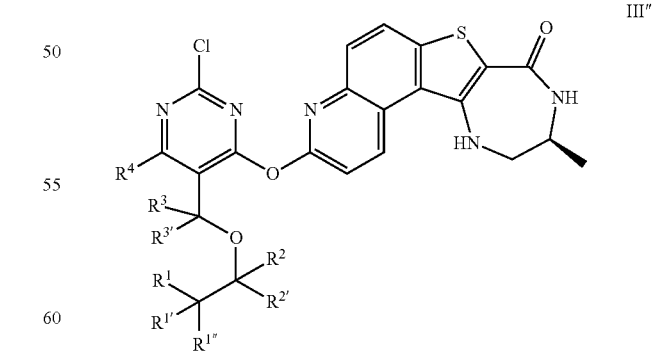

or a pharmaceutically acceptable salt thereof, wherein each of $R^1$, $R^{1'}$, $R^{1''}$, $R^2$, $R^{2'}$, $R^3$, $R^{3'}$, and $R^4$ is as defined above and described herein, provided that at least one of $R^1$, $R^{1'}$, $R^{1''}$, $R^2$, $R^{2'}$, $R^3$, $R^{3'}$, and $R^4$ is deuterium.

In some embodiments, a compound of Formulae III, III' or III" is selected from the compounds in Table 2.

TABLE 2

Compounds of Formulae III, III' or III".

| Formula III | Formula III' | Formula III" | $R^1/R^{1'}/R^{1"}$ | $R^2/R^{2'}$ | $R^3/R^{3'}$ | $R^4$ |
|---|---|---|---|---|---|---|
| III-1 | III'-1 | III"-1 | D | H | H | H |
| III-2 | III'-2 | III"-2 | H | D | H | H |
| III-3 | III'-3 | III"-3 | H | H | D | H |
| III-4 | III'-4 | III"-4 | D | D | H | H |
| III-5 | III'-5 | III"-5 | D | H | D | H |
| III-6 | III'-6 | III"-6 | H | D | D | H |
| III-7 | III'-7 | III"-7 | D | D | D | H |
| III-8 | III'-8 | III"-8 | H | H | H | D |
| III-9 | III'-9 | III"-9 | D | H | H | D |
| III-10 | III'-10 | III"-10 | H | D | H | D |
| III-11 | III'-11 | III"-11 | H | H | D | D |
| III-12 | III'-12 | III"-12 | D | D | H | D |
| III-13 | III'-13 | III"-13 | D | H | D | D |
| III-14 | III'-14 | III"-14 | H | D | D | D |
| III-15 | III'-15 | III"-15 | D | D | D | D |

In some embodiments, each of each of $R^1$, $R^{1'}$, $R^{1"}$, $R^2$, $R^{2'}$, $R^3$, $R^{3'}$, $R^4$, $R^{xa}$, $R^{xb}$, $R^{ya}$, and $R^{yb}$ is deuterium. In some embodiments, each of each of $R^1$, $R^{1'}$, $R^{1"}$, $R^2$, $R^{2'}$, $R^3$, $R^{3'}$, $R^4$, $R^{xa}$, $R^{xb}$, $R^{ya}$, and $R^{yb}$ is hydrogen. Accordingly, in some embodiments, the present invention provides a compound of Formulae IV, IV' or IV":

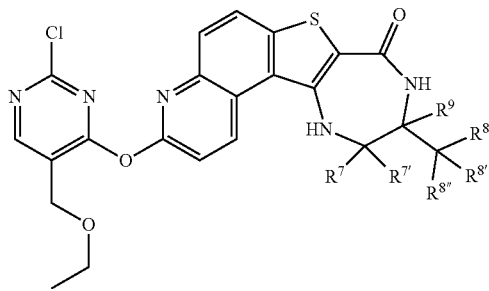

IV

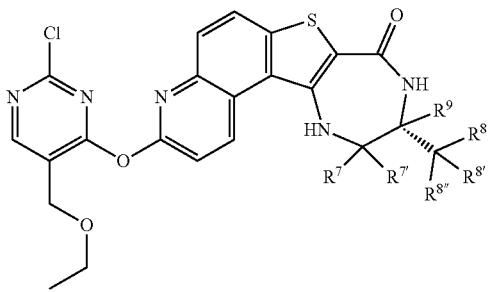

IV'

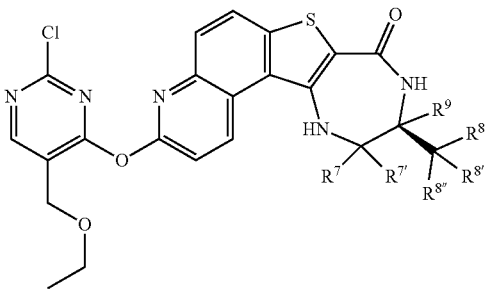

IV"

or a pharmaceutically acceptable salt thereof, wherein each of $R^7$, $R^{7'}$, $R^8$, $R^{8'}$, $R^{8"}$, and $R^9$ is as defined above and described herein, provided that at least one of $R^7$, $R^{7'}$, $R^8$, $R^{8'}$, $R^{8"}$, and $R^9$ is deuterium.

In some embodiments, a compound of Formulae IV, IV' or IV" is selected from those in Table 3.

TABLE 3

Compounds of Formulae IV, IV' or IV".

| Formula IV | Formula IV' | Formula IV" | $R^7$ | $R^{7'}$ | $R^8$ | $R^{8'}$ | $R^{8"}$ | $R^9$ |
|---|---|---|---|---|---|---|---|---|
| IV-1 | IV'-1 | IV"-1 | H | H | D | H | H | H |
| IV-2 | IV'-2 | IV"-2 | H | H | H | D | H | H |
| IV-3 | IV'-3 | IV"-3 | H | H | H | H | D | H |
| IV-4 | IV'-4 | IV"-4 | H | H | D | D | H | H |
| IV-5 | IV'-5 | IV"-5 | H | H | D | H | D | H |
| IV-6 | IV'-6 | IV"-6 | H | H | H | D | D | H |
| IV-7 | IV'-7 | IV"-7 | H | H | D | D | D | H |
| IV-8 | IV'-8 | IV"-8 | H | D | H | H | H | H |
| IV-9 | IV'-9 | IV"-9 | H | D | D | H | H | H |
| IV-10 | IV'-10 | IV"-10 | H | D | H | D | H | H |
| IV-11 | IV'-11 | IV"-11 | H | D | H | H | D | H |
| IV-12 | IV'-12 | IV"-12 | H | D | D | D | H | H |
| IV-13 | IV'-13 | IV"-13 | H | D | D | H | D | H |
| IV-14 | IV'-14 | IV"-14 | H | D | H | D | D | H |
| IV-15 | IV'-15 | IV"-15 | H | D | D | D | D | H |
| IV-16 | IV'-16 | IV"-16 | D | H | H | H | H | H |
| IV-17 | IV'-17 | IV"-17 | D | H | D | H | H | H |
| IV-18 | IV'-18 | IV"-18 | D | H | H | D | H | H |
| IV-19 | IV'-19 | IV"-19 | D | H | H | H | D | H |
| IV-20 | IV'-20 | IV"-20 | D | H | D | D | H | H |
| IV-21 | IV'-21 | IV"-21 | D | H | D | H | D | H |
| IV-22 | IV'-22 | IV"-22 | D | H | H | D | D | H |
| IV-23 | IV'-23 | IV"-23 | D | H | D | D | D | H |
| IV-24 | IV'-24 | IV"-24 | D | D | H | H | H | H |
| IV-25 | IV'-25 | IV"-25 | D | D | D | H | H | H |
| IV-26 | IV'-26 | IV"-26 | D | D | H | D | H | H |
| IV-27 | IV'-27 | IV"-27 | D | D | H | H | D | H |
| IV-28 | IV'-28 | IV"-28 | D | D | D | D | H | H |
| IV-29 | IV'-29 | IV"-29 | D | D | D | H | D | H |
| IV-30 | IV'-30 | IV"-30 | D | D | H | D | D | H |
| IV-31 | IV'-31 | IV"-31 | D | D | D | D | D | H |
| IV-32 | IV'-32 | IV"-32 | H | H | H | H | H | D |
| IV-33 | IV'-33 | IV"-33 | H | H | D | H | H | D |
| IV-34 | IV'-34 | IV"-34 | H | H | H | D | H | D |
| IV-35 | IV'-35 | IV"-35 | H | H | H | H | D | D |
| IV-36 | IV'-36 | IV"-36 | H | H | D | D | H | D |
| IV-37 | IV'-37 | IV"-37 | H | H | D | H | D | D |
| IV-38 | IV'-38 | IV"-38 | H | H | H | D | D | D |
| IV-39 | IV'-39 | IV"-39 | H | H | D | D | D | D |
| IV-40 | IV'-40 | IV"-40 | H | D | H | H | H | D |
| IV-41 | IV'-41 | IV"-41 | H | D | D | H | H | D |
| IV-42 | IV'-42 | IV"-42 | H | D | H | D | H | D |
| IV-43 | IV'-43 | IV"-43 | H | D | H | H | D | D |
| IV-44 | IV'-44 | IV"-44 | H | D | D | D | H | D |
| IV-45 | IV'-45 | IV"-45 | H | D | D | H | D | D |
| IV-46 | IV'-46 | IV"-46 | H | D | H | D | D | D |
| IV-47 | IV'-47 | IV"-47 | H | D | D | D | D | D |
| IV-48 | IV'-48 | IV"-48 | D | H | H | H | H | D |
| IV-49 | IV'-49 | IV"-49 | D | H | D | H | H | D |
| IV-50 | IV'-50 | IV"-50 | D | H | H | D | H | D |
| IV-51 | IV'-51 | IV"-51 | D | H | H | H | D | D |
| IV-52 | IV'-52 | IV"-52 | D | H | D | D | H | D |
| IV-53 | IV'-53 | IV"-53 | D | H | D | H | D | D |
| IV-54 | IV'-54 | IV"-54 | D | H | H | D | D | D |
| IV-55 | IV'-55 | IV"-55 | D | H | D | D | D | D |
| IV-56 | IV'-56 | IV"-56 | D | D | H | H | H | D |
| IV-57 | IV'-57 | IV"-57 | D | D | D | H | H | D |
| IV-58 | IV'-58 | IV"-58 | D | D | H | D | H | D |
| IV-59 | IV'-59 | IV"-59 | D | D | H | H | D | D |
| IV-60 | IV'-60 | IV"-60 | D | D | D | D | H | D |
| IV-61 | IV'-61 | IV"-61 | D | D | D | H | D | D |
| IV-62 | IV'-62 | IV"-62 | D | D | H | D | D | D |
| IV-63 | IV'-63 | IV"-63 | D | D | D | D | D | D |

In some embodiments, each of $R^3$, $R^{3'}$, $R^4$, $R^{xa}$, $R^{xb}$, $R^{ya}$, and $R^{yb}$ is deuterium. In some embodiments, each of $R^3$, $R^{3'}$, $R^4$, $R^{xa}$, $R^{xb}$, $R^{ya}$, and $R^{yb}$ is hydrogen. Accordingly, in some embodiments, the present invention provides a compound of Formulae V, V' or V":

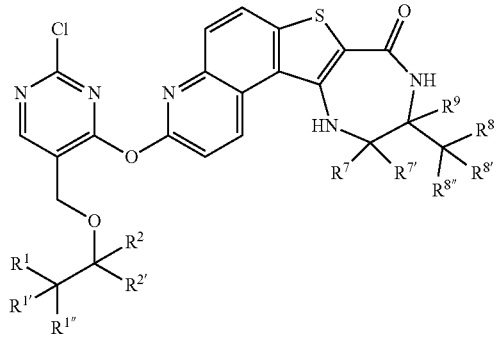

V

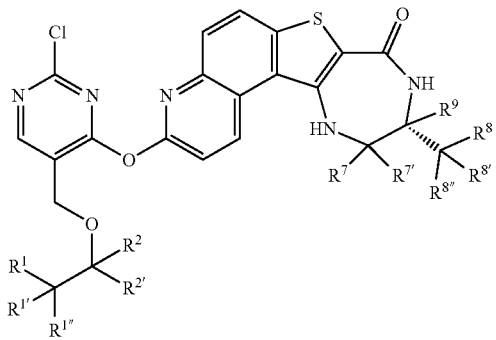

V'

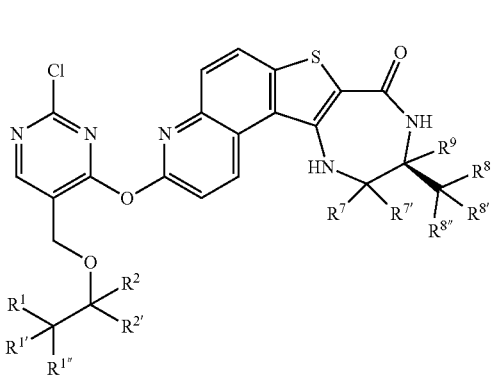

V"

or a pharmaceutically acceptable salt thereof, wherein each of $R^1$, $R^{1'}$, $R^{1''}$, $R^2$, $R^{2'}$, $R^7$, $R^{7'}$, $R^8$, $R^{8'}$, $R^{8''}$, and $R^9$ is as defined above and described herein, provided that at least one of $R^1$, $R^{1'}$, $R^{1''}$, $R^2$, $R^{2'}$, $R^7$, $R^{7'}$, $R^8$, $R^{8'}$, $R^{8''}$, and $R^9$ is deuterium.

In some embodiments, a compound of Formulae V, V' or V" is selected from those in Table 4:

TABLE 4

Compounds of Formulae V, V' or V".

| Formula V | Formula V' | Formula V" | $R^1/R^{1'}/R^{1''}$ | $R^2/R^{2'}$ | $R^7/R^{7'}$ | $R^8/R^{8'}/R^{8''}$ | $R^9$ |
|---|---|---|---|---|---|---|---|
| V-1 | V'-1 | V"-1 | D | H | D | H | H |
| V-2 | V'-2 | V"-2 | D | H | H | D | H |
| V-3 | V'-3 | V"-3 | D | H | H | H | D |
| V-4 | V'-4 | V"-4 | D | H | D | D | H |
| V-5 | V'-5 | V"-5 | D | H | D | H | D |
| V-6 | V'-6 | V"-6 | D | H | H | D | D |
| V-7 | V'-7 | V"-7 | D | H | D | D | D |
| V-8 | V'-8 | V"-8 | H | D | D | H | H |
| V-9 | V'-9 | V"-9 | H | D | H | D | H |
| V-10 | V'-10 | V"-10 | H | D | H | H | D |
| V-11 | V'-11 | V"-11 | H | D | D | D | H |
| V-12 | V'-12 | V"-12 | H | D | D | H | D |
| V-13 | V'-13 | V"-13 | H | D | H | D | D |
| V-14 | V'-14 | V"-14 | H | D | D | D | D |
| V-15 | V'-15 | V"-15 | D | D | D | H | H |
| V-16 | V'-16 | V"-16 | D | D | H | D | H |
| V-17 | V'-17 | V"-17 | D | D | H | H | D |
| V-18 | V'-18 | V"-18 | D | D | D | D | H |
| V-19 | V'-19 | V"-19 | D | D | D | H | D |
| V-20 | V'-20 | V"-20 | D | D | H | D | D |
| V-21 | V'-21 | V"-21 | D | D | D | D | D |

In some embodiments, each of $R^3$, $R^{3'}$, and $R^4$ is deuterium. In some embodiments, each of $R^3$, $R^{3'}$, and $R^4$ is hydrogen. Accordingly, in some embodiments, the present invention provides a compound of Formulae VI, VI' or VI":

-continued

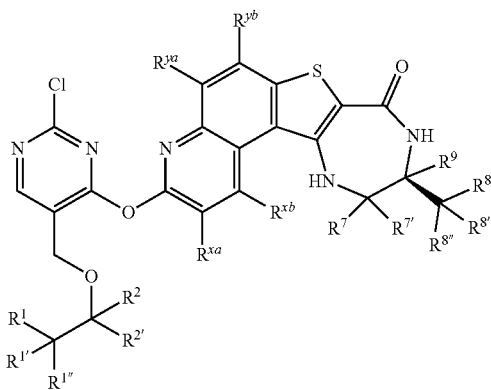

VI″ or a pharmaceutically acceptable salt thereof, wherein each of $R^1$, $R^{1'}$, $R^{1''}$, $R^2$, $R^{2'}$, $R^7$, $R^{7'}$, $R^8$, $R^{8'}$, $R^{8''}$, $R^9$, $R^{xa}$, $R^{xb}$, $R^{ya}$, and $R^{yb}$ is as defined above and described herein, provided that at least one of $R^1$, $R^{1'}$, $R^{1''}$, $R^2$, $R^{2'}$, $R^7$, $R^{7'}$, $R^8$, $R^{8'}$, $R^{8''}$, $R^9$, $R^{xa}$, $R^{xb}$, $R^{ya}$, and $R^{yb}$ is deuterium.

In some embodiments of Formulae VI, VI' or VI″, at least one of $R^1$, $R^{1'}$, $R^{1''}$, $R^2$, $R^{2'}$, $R^7$, $R^{7'}$, $R^8$, $R^{8'}$, $R^{8''}$, $R^9$, $R^{xa}$, $R^{xb}$, $R^{ya}$, and $R^{yb}$ is deuterium. In some embodiments of Formulae VI, VI' or VI″, the compound is selected from those in Table 5, Table 6, Table 7 and Table 8:

TABLE 5

Compounds of Formulae VI, VI' or VI″, wherein each of $R^{ya}$ and $R^{yb}$ is hydrogen.

| Formula VI | Formula VI' | Formula VI″ | $R^1/R^{1'}/R^{1''}$ | $R^2/R^{2'}$ | $R^7/R^{7'}$ | $R^8/R^{8'}/R^{8''}$ | $R^9$ | $R^{xa}$ | $R^{xb}$ |
|---|---|---|---|---|---|---|---|---|---|
| VI-1 | VI'-1 | VI″-1 | H | H | H | H | H | H | D |
| VI-2 | VI'-2 | VI″-2 | H | H | D | H | H | H | D |
| VI-3 | VI'-3 | VI″-3 | H | H | H | D | H | H | D |
| VI-4 | VI'-4 | VI″-4 | H | H | H | H | D | H | D |
| VI-5 | VI'-5 | VI″-5 | H | H | D | D | H | H | D |
| VI-6 | VI'-6 | VI″-6 | H | H | D | H | D | H | D |
| VI-7 | VI'-7 | VI″-7 | H | H | H | D | D | H | D |
| VI-8 | VI'-8 | VI″-8 | H | H | D | D | D | H | D |
| VI-9 | VI'-9 | VI″-9 | H | D | H | H | H | H | D |
| VI-10 | VI'-10 | VI″-10 | H | D | D | H | H | H | D |
| VI-11 | VI'-11 | VI″-11 | H | D | H | D | H | H | D |
| VI-12 | VI'-12 | VI″-12 | H | D | H | H | D | H | D |
| VI-13 | VI'-13 | VI″-13 | H | D | D | D | H | H | D |
| VI-14 | VI'-14 | VI″-14 | H | D | D | H | D | H | D |
| VI-15 | VI'-15 | VI″-15 | H | D | H | D | D | H | D |
| VI-16 | VI'-16 | VI″-16 | H | D | D | D | D | H | D |
| VI-17 | VI'-17 | VI″-17 | D | H | H | H | H | H | D |
| VI-18 | VI'-18 | VI″-18 | D | H | D | H | H | H | D |
| VI-19 | VI'-19 | VI″-19 | D | H | H | D | H | H | D |
| VI-20 | VI'-20 | VI″-20 | D | H | H | H | D | H | D |
| VI-21 | VI'-21 | VI″-21 | D | H | D | D | H | H | D |
| VI-22 | VI'-22 | VI″-22 | D | H | D | H | D | H | D |
| VI-23 | VI'-23 | VI″-23 | D | H | H | D | D | H | D |
| VI-24 | VI'-24 | VI″-24 | D | H | D | D | D | H | D |
| VI-25 | VI'-25 | VI″-25 | D | D | H | H | H | H | D |
| VI-26 | VI'-26 | VI″-26 | D | D | D | H | H | H | D |
| VI-27 | VI'-27 | VI″-27 | D | D | H | D | H | H | D |
| VI-28 | VI'-28 | VI″-28 | D | D | H | H | D | H | D |
| VI-29 | VI'-29 | VI″-29 | D | D | D | D | H | H | D |
| VI-30 | VI'-30 | VI″-30 | D | D | D | H | D | H | D |
| VI-31 | VI'-31 | VI″-31 | D | D | H | D | D | H | D |
| VI-32 | VI'-32 | VI″-32 | D | D | D | D | D | H | D |
| VI-33 | VI'-33 | VI″-33 | H | H | H | H | H | D | H |
| VI-34 | VI'-34 | VI″-34 | H | H | D | H | H | D | H |
| VI-35 | VI'-35 | VI″-35 | H | H | H | D | H | D | H |
| VI-36 | VI'-36 | VI″-36 | H | H | H | H | D | D | H |
| VI-37 | VI'-37 | VI″-37 | H | H | D | D | H | D | H |
| VI-38 | VI'-38 | VI″-38 | H | H | D | H | D | D | H |

TABLE 5-continued

Compounds of Formulae VI, VI' or VI″, wherein each of $R^{ya}$ and $R^{yb}$ is hydrogen.

| Formula VI | Formula VI' | Formula VI″ | $R^1/R^{1'}/R^{1''}$ | $R^2/R^{2'}$ | $R^7/R^{7'}$ | $R^8/R^{8'}/R^{8''}$ | $R^9$ | $R^{xa}$ | $R^{xb}$ |
|---|---|---|---|---|---|---|---|---|---|
| VI-39 | VI'-39 | VI″-39 | H | H | H | D | D | D | H |
| VI-40 | VI'-40 | VI″-40 | H | H | D | D | D | D | H |
| VI-41 | VI'-41 | VI″-41 | H | D | H | H | H | D | H |
| VI-42 | VI'-42 | VI″-42 | H | D | D | H | H | D | H |
| VI-43 | VI'-43 | VI″-43 | H | D | H | D | H | D | H |
| VI-44 | VI'-44 | VI″-44 | H | D | H | H | D | D | H |
| VI-45 | VI'-45 | VI″-45 | H | D | D | D | H | D | H |
| VI-46 | VI'-46 | VI″-46 | H | D | D | H | D | D | H |
| VI-47 | VI'-47 | VI″-47 | H | D | H | D | D | D | H |
| VI-48 | VI'-48 | VI″-48 | H | D | D | D | D | D | H |
| VI-49 | VI'-49 | VI″-49 | D | H | H | H | H | D | H |
| VI-50 | VI'-50 | VI″-50 | D | H | D | H | H | D | H |
| VI-51 | VI'-51 | VI″-51 | D | H | H | D | H | D | H |
| VI-52 | VI'-52 | VI″-52 | D | H | H | H | D | D | H |
| VI-53 | VI'-53 | VI″-53 | D | H | D | D | H | D | H |
| VI-54 | VI'-54 | VI″-54 | D | H | D | H | D | D | H |
| VI-55 | VI'-55 | VI″-55 | D | H | H | D | D | D | H |
| VI-56 | VI'-56 | VI″-56 | D | H | D | D | D | D | H |
| VI-57 | VI'-57 | VI″-57 | D | D | H | H | H | D | H |
| VI-58 | VI'-58 | VI″-58 | D | D | D | H | H | D | H |
| VI-59 | VI'-59 | VI″-59 | D | D | H | D | H | D | H |
| VI-60 | VI'-60 | VI″-60 | D | D | H | H | D | D | H |
| VI-61 | VI'-61 | VI″-61 | D | D | D | D | H | D | H |
| VI-62 | VI'-62 | VI″-62 | D | D | D | H | D | D | H |
| VI-63 | VI'-63 | VI″-63 | D | D | H | D | D | D | H |
| VI-64 | VI'-64 | VI″-64 | D | D | D | D | D | D | H |
| VI-65 | VI'-65 | VI″-65 | H | H | H | H | H | D | D |
| VI-66 | VI'-66 | VI″-66 | H | H | D | H | H | D | D |
| VI-67 | VI'-67 | VI″-67 | H | H | H | D | H | D | D |
| VI-68 | VI'-68 | VI″-68 | H | H | H | H | D | D | D |
| VI-69 | VI'-69 | VI″-69 | H | H | D | D | H | D | D |
| VI-70 | VI'-70 | VI″-70 | H | H | D | H | D | D | D |
| VI-71 | VI'-71 | VI″-71 | H | H | H | D | D | D | D |
| VI-72 | VI'-72 | VI″-72 | H | H | D | D | D | D | D |
| VI-73 | VI'-73 | VI″-73 | H | D | H | H | H | D | D |
| VI-74 | VI'-74 | VI″-74 | H | D | D | H | H | D | D |
| VI-75 | VI'-75 | VI″-75 | H | D | H | D | H | D | D |
| VI-76 | VI'-76 | VI″-76 | H | D | H | H | D | D | D |
| VI-77 | VI'-77 | VI″-77 | H | D | D | D | H | D | D |
| VI-78 | VI'-78 | VI″-78 | H | D | D | H | D | D | D |
| VI-79 | VI'-79 | VI″-79 | H | D | H | D | D | D | D |
| VI-80 | VI'-80 | VI″-80 | H | D | D | D | D | D | D |
| VI-81 | VI'-81 | VI″-81 | D | H | H | H | H | D | D |
| VI-82 | VI'-82 | VI″-82 | D | H | D | H | H | D | D |
| VI-83 | VI'-83 | VI″-83 | D | H | H | D | H | D | D |
| VI-84 | VI'-84 | VI″-84 | D | H | H | H | D | D | D |
| VI-85 | VI'-85 | VI″-85 | D | H | D | D | H | D | D |
| VI-86 | VI'-86 | VI″-86 | D | H | D | H | D | D | D |
| VI-87 | VI'-87 | VI″-87 | D | H | H | D | D | D | D |
| VI-88 | VI'-88 | VI″-88 | D | H | D | D | D | D | D |
| VI-89 | VI'-89 | VI″-89 | D | D | H | H | H | D | D |
| VI-90 | VI'-90 | VI″-90 | D | D | D | H | H | D | D |
| VI-91 | VI'-91 | VI″-91 | D | D | H | D | H | D | D |
| VI-92 | VI'-92 | VI″-92 | D | D | H | H | D | D | D |
| VI-93 | VI'-93 | VI″-93 | D | D | D | D | H | D | D |
| VI-94 | VI'-94 | VI″-94 | D | D | D | H | D | D | D |
| VI-95 | VI'-95 | VI″-95 | D | D | H | D | D | D | D |
| VI-96 | VI'-96 | VI″-96 | D | D | D | D | D | D | D |

TABLE 6

Compounds of Formulae VI, VI' or VI″, wherein each of $R^{ya}$ and $R^{yb}$ is deuterium.

| Formula VI | Formula VI' | Formula VI″ | $R^1/R^{1'}/R^{1''}$ | $R^2/R^{2'}$ | $R^7/R^{7'}$ | $R^8/R^{8'}/R^{8''}$ | $R^9$ | $R^{xa}$ | $R^{xb}$ |
|---|---|---|---|---|---|---|---|---|---|
| VI-97 | VI'-97 | VI″-97 | H | H | H | H | H | H | H |
| VI-98 | VI'-98 | VI″-98 | H | H | D | H | H | H | H |
| VI-99 | VI'-99 | VI″-99 | H | H | H | D | H | H | H |
| VI-100 | VI'-100 | VI″-100 | H | H | H | H | D | H | H |

TABLE 6-continued

Compounds of Formulae VI, VI' or VI", wherein each of $R^{ya}$ and $R^{yb}$ is deuterium.

| Formula VI | Formula VI' | Formula VI" | $R^1/R^{1'}/R^{1''}$ | $R^2/R^{2'}$ | $R^7/R^{7'}$ | $R^8/R^{8'}/R^{8''}$ | $R^9$ | $R^{xa}$ | $R^{xb}$ |
|---|---|---|---|---|---|---|---|---|---|
| VI-101 | VI'-101 | VI"-101 | H | H | D | D | H | H | H |
| VI-102 | VI'-102 | VI"-102 | H | H | D | H | D | H | H |
| VI-103 | VI'-103 | VI"-103 | H | H | H | D | D | H | H |
| VI-104 | VI'-104 | VI"-104 | H | H | D | D | D | H | H |
| VI-105 | VI'-105 | VI"-105 | H | D | H | H | H | H | H |
| VI-106 | VI'-106 | VI"-106 | H | D | D | H | H | H | H |
| VI-107 | VI'-107 | VI"-107 | H | D | H | D | H | H | H |
| VI-108 | VI'-108 | VI"-108 | H | D | H | H | D | H | H |
| VI-109 | VI'-109 | VI"-109 | H | D | D | D | H | H | H |
| VI-110 | VI'-110 | VI"-110 | H | D | D | H | D | H | H |
| VI-111 | VI'-111 | VI"-111 | H | D | H | D | D | H | H |
| VI-112 | VI'-112 | VI"-112 | H | D | D | D | D | H | H |
| VI-113 | VI'-113 | VI"-113 | D | H | H | H | H | H | H |
| VI-114 | VI'-114 | VI"-114 | D | H | D | H | H | H | H |
| VI-115 | VI'-115 | VI"-115 | D | H | H | D | H | H | H |
| VI-116 | VI'-116 | VI"-116 | D | H | H | H | D | H | H |
| VI-117 | VI'-117 | VI"-117 | D | H | D | D | H | H | H |
| VI-118 | VI'-118 | VI"-118 | D | H | D | H | D | H | H |
| VI-119 | VI'-119 | VI"-119 | D | H | H | D | D | H | H |
| VI-120 | VI'-120 | VI"-120 | D | H | D | D | D | H | H |
| VI-121 | VI'-121 | VI"-121 | D | D | H | H | H | H | H |
| VI-122 | VI'-122 | VI"-122 | D | D | D | H | H | H | H |
| VI-123 | VI'-123 | VI"-123 | D | D | H | D | H | H | H |
| VI-124 | VI'-124 | VI"-124 | D | D | H | H | D | H | H |
| VI-125 | VI'-125 | VI"-125 | D | D | D | D | H | H | H |
| VI-126 | VI'-126 | VI"-126 | D | D | D | H | D | H | H |
| VI-127 | VI'-127 | VI"-127 | D | D | H | D | D | H | H |
| VI-128 | VI'-128 | VI"-128 | D | D | D | D | D | H | H |
| VI-129 | VI'-129 | VI"-129 | H | H | H | H | H | H | D |
| VI-130 | VI'-130 | VI"-130 | H | H | D | H | H | H | D |
| VI-131 | VI'-131 | VI"-131 | H | H | H | D | H | H | D |
| VI-132 | VI'-132 | VI"-132 | H | H | H | H | D | H | D |
| VI-133 | VI'-133 | VI"-133 | H | H | D | D | H | H | D |
| VI-134 | VI'-134 | VI"-134 | H | H | D | H | D | H | D |
| VI-135 | VI'-135 | VI"-135 | H | H | H | D | D | H | D |
| VI-136 | VI'-136 | VI"-136 | H | H | D | D | D | H | D |
| VI-137 | VI'-137 | VI"-137 | H | D | H | H | H | H | D |
| VI-138 | VI'-138 | VI"-138 | H | D | D | H | H | H | D |
| VI-139 | VI'-139 | VI"-139 | H | D | H | D | H | H | D |
| VI-140 | VI'-140 | VI"-140 | H | D | H | H | D | H | D |
| VI-141 | VI'-141 | VI"-141 | H | D | D | D | H | H | D |
| VI-142 | VI'-142 | VI"-142 | H | D | D | H | D | H | D |
| VI-143 | VI'-143 | VI"-143 | H | D | H | D | D | H | D |
| VI-144 | VI'-144 | VI"-144 | H | D | D | D | D | H | D |
| VI-145 | VI'-145 | VI"-145 | D | H | H | H | H | H | D |
| VI-146 | VI'-146 | VI"-146 | D | H | D | H | H | H | D |
| VI-147 | VI'-147 | VI"-147 | D | H | H | D | H | H | D |
| VI-148 | VI'-148 | VI"-148 | D | H | H | H | D | H | D |
| VI-149 | VI'-149 | VI"-149 | D | H | D | D | H | H | D |
| VI-150 | VI'-150 | VI"-150 | D | H | D | H | D | H | D |
| VI-151 | VI'-151 | VI"-151 | D | H | H | D | D | H | D |
| VI-152 | VI'-152 | VI"-152 | D | H | D | D | D | H | D |
| VI-153 | VI'-153 | VI"-153 | D | D | H | H | H | H | D |
| VI-154 | VI'-154 | VI"-154 | D | D | D | H | H | H | D |
| VI-155 | VI'-155 | VI"-155 | D | D | H | D | H | H | D |
| VI-156 | VI'-156 | VI"-156 | D | D | H | H | D | H | D |
| VI-157 | VI'-157 | VI"-157 | D | D | D | D | H | H | D |
| VI-158 | VI'-158 | VI"-158 | D | D | D | H | D | H | D |
| VI-159 | VI'-159 | VI"-159 | D | D | H | D | D | H | D |
| VI-160 | VI'-160 | VI"-160 | D | D | D | D | D | H | D |
| VI-161 | VI'-161 | VI"-161 | H | H | H | H | H | D | H |
| VI-162 | VI'-162 | VI"-162 | H | H | D | H | H | D | H |
| VI-163 | VI'-163 | VI"-163 | H | H | H | D | H | D | H |
| VI-164 | VI'-164 | VI"-164 | H | H | H | H | D | D | H |
| VI-165 | VI'-165 | VI"-165 | H | H | D | D | H | D | H |
| VI-166 | VI'-166 | VI"-166 | H | H | D | H | D | D | H |
| VI-167 | VI'-167 | VI"-167 | H | H | H | D | D | D | H |
| VI-168 | VI'-168 | VI"-168 | H | H | D | D | D | D | H |
| VI-169 | VI'-169 | VI"-169 | H | D | H | H | H | D | H |
| VI-170 | VI'-170 | VI"-170 | H | D | D | H | H | D | H |
| VI-171 | VI'-171 | VI"-171 | H | D | H | D | H | D | H |
| VI-172 | VI'-172 | VI"-172 | H | D | H | H | D | D | H |
| VI-173 | VI'-173 | VI"-173 | H | D | D | D | H | D | H |
| VI-174 | VI'-174 | VI"-174 | H | D | D | H | D | D | H |
| VI-175 | VI'-175 | VI"-175 | H | D | H | D | D | D | H |
| VI-176 | VI'-176 | VI"-176 | H | D | D | D | D | D | H |
| VI-177 | VI'-177 | VI"-177 | D | H | H | H | H | D | H |
| VI-178 | VI'-178 | VI"-178 | D | H | D | H | H | D | H |
| VI-179 | VI'-179 | VI"-179 | D | H | H | D | H | D | H |
| VI-180 | VI'-180 | VI"-180 | D | H | H | H | D | D | H |
| VI-181 | VI'-181 | VI"-181 | D | H | D | D | H | D | H |
| VI-182 | VI'-182 | VI"-182 | D | H | D | H | D | D | H |
| VI-183 | VI'-183 | VI"-183 | D | H | H | D | D | D | H |
| VI-184 | VI'-184 | VI"-184 | D | H | D | D | D | D | H |
| VI-185 | VI'-185 | VI"-185 | D | D | H | H | H | D | H |
| VI-186 | VI'-186 | VI"-186 | D | D | D | H | H | D | H |
| VI-187 | VI'-187 | VI"-187 | D | D | H | D | H | D | H |
| VI-188 | VI'-188 | VI"-188 | D | D | H | H | D | D | H |
| VI-189 | VI'-189 | VI"-189 | D | D | D | D | H | D | H |
| VI-190 | VI'-190 | VI"-190 | D | D | D | H | D | D | H |
| VI-191 | VI'-191 | VI"-191 | D | D | H | D | D | D | H |
| VI-192 | VI'-192 | VI"-192 | D | D | D | D | D | D | H |
| VI-193 | VI'-193 | VI"-193 | H | H | H | H | H | H | D |
| VI-194 | VI'-194 | VI"-194 | H | H | D | H | H | H | D |
| VI-195 | VI'-195 | VI"-195 | H | H | H | D | H | H | D |
| VI-196 | VI'-196 | VI"-196 | H | H | H | H | D | H | D |
| VI-197 | VI'-197 | VI"-197 | H | H | D | D | H | D | D |
| VI-198 | VI'-198 | VI"-198 | H | H | D | H | D | D | D |
| VI-199 | VI'-199 | VI"-199 | H | H | H | D | D | D | D |
| VI-200 | VI'-200 | VI"-200 | H | H | D | D | D | D | D |
| VI-201 | VI'-201 | VI"-201 | H | D | H | H | H | D | D |
| VI-202 | VI'-202 | VI"-202 | H | D | D | H | H | D | D |
| VI-203 | VI'-203 | VI"-203 | H | D | H | D | H | D | D |
| VI-204 | VI'-204 | VI"-204 | H | D | H | H | D | D | D |
| VI-205 | VI'-205 | VI"-205 | H | D | D | D | H | D | D |
| VI-206 | VI'-206 | VI"-206 | H | D | D | H | D | D | D |
| VI-207 | VI'-207 | VI"-207 | H | D | H | D | D | D | D |
| VI-208 | VI'-208 | VI"-208 | H | D | D | D | D | D | D |
| VI-209 | VI'-209 | VI"-209 | D | H | H | H | H | D | D |
| VI-210 | VI'-210 | VI"-210 | D | H | D | H | H | D | D |
| VI-211 | VI'-211 | VI"-211 | D | H | H | D | H | D | D |
| VI-212 | VI'-212 | VI"-212 | D | H | H | H | D | D | D |
| VI-213 | VI'-213 | VI"-213 | D | H | D | D | H | D | D |
| VI-214 | VI'-214 | VI"-214 | D | H | D | H | D | D | D |
| VI-215 | VI'-215 | VI"-215 | D | H | H | D | D | D | D |
| VI-216 | VI'-216 | VI"-216 | D | H | D | D | D | D | D |
| VI-217 | VI'-217 | VI"-217 | D | D | H | H | H | D | D |
| VI-218 | VI'-218 | VI"-218 | D | D | D | H | H | D | D |
| VI-219 | VI'-219 | VI"-219 | D | D | H | D | H | D | D |
| VI-220 | VI'-220 | VI"-220 | D | D | H | H | D | D | D |
| VI-221 | VI'-221 | VI"-221 | D | D | D | D | H | D | D |
| VI-222 | VI'-222 | VI"-222 | D | D | D | H | D | D | D |
| VI-223 | VI'-223 | VI"-223 | D | D | H | D | D | D | D |
| VI-224 | VI'-224 | VI"-224 | D | D | D | D | D | D | D |

TABLE 7

Compounds of Formulae VI, VI' or VI", wherein $R^{ya}$ is hydrogen and $R^{yb}$ is deuterium.

| Formula VI | Formula VI' | Formula VI" | $R^1/R^{1'}/R^{1''}$ | $R^2/R^{2'}$ | $R^7/R^{7'}$ | $R^8/R^{8'}/R^{8''}$ | $R^9$ | $R^{xa}$ | $R^{xb}$ |
|---|---|---|---|---|---|---|---|---|---|
| VI-225 | VI'-225 | VI"-225 | H | H | H | H | H | H | H |
| VI-226 | VI'-226 | VI"-226 | H | H | D | H | H | H | H |
| VI-227 | VI'-227 | VI"-227 | H | H | H | D | H | H | H |
| VI-228 | VI'-228 | VI"-228 | H | H | H | H | D | H | H |
| VI-229 | VI'-229 | VI"-229 | H | H | D | D | H | H | H |
| VI-230 | VI'-230 | VI"-230 | H | H | D | H | D | H | H |
| VI-231 | VI'-231 | VI"-231 | H | H | H | D | D | H | H |
| VI-232 | VI'-232 | VI"-232 | H | H | D | D | D | H | H |
| VI-233 | VI'-233 | VI"-233 | H | D | H | H | H | H | H |
| VI-234 | VI'-234 | VI"-234 | H | D | D | H | H | H | H |
| VI-235 | VI'-235 | VI"-235 | H | D | H | D | H | H | H |
| VI-236 | VI'-236 | VI"-236 | H | D | H | H | D | H | H |

TABLE 7-continued

Compounds of Formulae VI, VI' or VI", wherein $R^{ya}$ is hydrogen and $R^{yb}$ is deuterium.

| Formula VI | Formula VI' | Formula VI" | $R^1/R^{1'}/R^{1''}$ | $R^2/R^{2'}$ | $R^7/R^{7'}$ | $R^8/R^{8'}/R^{8''}$ | $R^9$ | $R^{xa}$ | $R^{xb}$ |
|---|---|---|---|---|---|---|---|---|---|
| VI-237 | VI'-237 | VI"-237 | H | D | D | D | H | H | H |
| VI-238 | VI'-238 | VI"-238 | H | D | H | D | D | H | H |
| VI-239 | VI'-239 | VI"-239 | H | D | D | H | D | H | H |
| VI-240 | VI'-240 | VI"-240 | H | D | D | D | D | H | H |
| VI-241 | VI'-241 | VI"-241 | D | H | H | H | H | H | H |
| VI-242 | VI'-242 | VI"-242 | D | H | H | D | H | H | H |
| VI-243 | VI'-243 | VI"-243 | D | H | H | H | D | H | H |
| VI-244 | VI'-244 | VI"-244 | D | H | H | D | D | H | H |
| VI-245 | VI'-245 | VI"-245 | D | H | D | H | H | H | H |
| VI-246 | VI'-246 | VI"-246 | D | H | D | D | H | H | H |
| VI-247 | VI'-247 | VI"-247 | D | H | D | H | D | H | H |
| VI-248 | VI'-248 | VI"-248 | D | H | D | D | D | H | H |
| VI-249 | VI'-249 | VI"-249 | D | D | H | H | H | H | H |
| VI-250 | VI'-250 | VI"-250 | D | D | H | D | H | H | H |
| VI-251 | VI'-251 | VI"-251 | D | D | H | H | D | H | H |
| VI-252 | VI'-252 | VI"-252 | D | D | H | D | D | H | H |
| VI-253 | VI'-253 | VI"-253 | D | D | D | H | H | H | H |
| VI-254 | VI'-254 | VI"-254 | D | D | D | D | H | H | H |
| VI-255 | VI'-255 | VI"-255 | D | D | D | H | D | H | H |
| VI-256 | VI'-256 | VI"-256 | D | D | D | D | D | H | H |
| VI-257 | VI'-257 | VI"-257 | H | H | H | H | H | H | D |
| VI-258 | VI'-258 | VI"-258 | H | H | H | D | H | H | D |
| VI-259 | VI'-259 | VI"-259 | H | H | H | H | D | H | D |
| VI-260 | VI'-260 | VI"-260 | H | H | H | D | D | H | D |
| VI-261 | VI'-261 | VI"-261 | H | H | D | H | H | H | D |
| VI-262 | VI'-262 | VI"-262 | H | H | D | D | H | H | D |
| VI-263 | VI'-263 | VI"-263 | H | H | D | H | D | H | D |
| VI-264 | VI'-264 | VI"-264 | H | H | D | D | D | H | D |
| VI-265 | VI'-265 | VI"-265 | H | D | H | H | H | H | D |
| VI-266 | VI'-266 | VI"-266 | H | D | H | D | H | H | D |
| VI-267 | VI'-267 | VI"-267 | H | D | H | H | D | H | D |
| VI-268 | VI'-268 | VI"-268 | H | D | H | D | D | H | D |
| VI-269 | VI'-269 | VI"-269 | H | D | D | H | H | H | D |
| VI-270 | VI'-270 | VI"-270 | H | D | D | D | H | H | D |
| VI-271 | VI'-271 | VI"-271 | H | D | D | H | D | H | D |
| VI-272 | VI'-272 | VI"-272 | H | D | D | D | D | H | D |
| VI-273 | VI'-273 | VI"-273 | D | H | H | H | H | H | D |
| VI-274 | VI'-274 | VI"-274 | D | H | H | D | H | H | D |
| VI-275 | VI'-275 | VI"-275 | D | H | H | H | D | H | D |
| VI-276 | VI'-276 | VI"-276 | D | H | H | D | D | H | D |
| VI-277 | VI'-277 | VI"-277 | D | H | D | H | H | H | D |
| VI-278 | VI'-278 | VI"-278 | D | H | D | D | H | H | D |
| VI-279 | VI'-279 | VI"-279 | D | H | D | H | D | H | D |
| VI-280 | VI'-280 | VI"-280 | D | H | D | D | D | H | D |
| VI-281 | VI'-281 | VI"-281 | D | D | H | H | H | H | D |
| VI-282 | VI'-282 | VI"-282 | D | D | H | D | H | H | D |
| VI-283 | VI'-283 | VI"-283 | D | D | H | H | D | H | D |
| VI-284 | VI'-284 | VI"-284 | D | D | H | D | D | H | D |
| VI-285 | VI'-285 | VI"-285 | D | D | D | H | H | H | D |
| VI-286 | VI'-286 | VI"-286 | D | D | D | D | H | H | D |
| VI-287 | VI'-287 | VI"-287 | D | D | D | H | D | H | D |
| VI-288 | VI'-288 | VI"-288 | D | D | D | D | D | H | D |
| VI-289 | VI'-289 | VI"-289 | H | H | H | H | H | D | H |
| VI-290 | VI'-290 | VI"-290 | H | H | H | D | H | D | H |
| VI-291 | VI'-291 | VI"-291 | H | H | H | H | D | D | H |
| VI-292 | VI'-292 | VI"-292 | H | H | H | D | D | D | H |
| VI-293 | VI'-293 | VI"-293 | H | H | D | H | H | D | H |
| VI-294 | VI'-294 | VI"-294 | H | H | D | D | H | D | H |
| VI-295 | VI'-295 | VI"-295 | H | H | D | H | D | D | H |
| VI-296 | VI'-296 | VI"-296 | H | H | D | D | D | D | H |
| VI-297 | VI'-297 | VI"-297 | H | D | H | H | H | D | H |
| VI-298 | VI'-298 | VI"-298 | H | D | H | D | H | D | H |
| VI-299 | VI'-299 | VI"-299 | H | D | H | H | D | D | H |
| VI-300 | VI'-300 | VI"-300 | H | D | H | D | D | D | H |
| VI-301 | VI'-301 | VI"-301 | H | D | D | H | H | D | H |
| VI-302 | VI'-302 | VI"-302 | H | D | D | D | H | D | H |
| VI-303 | VI'-303 | VI"-303 | H | D | D | H | D | D | H |
| VI-304 | VI'-304 | VI"-304 | H | D | D | D | D | D | H |
| VI-305 | VI'-305 | VI"-305 | D | H | H | H | H | D | H |
| VI-306 | VI'-306 | VI"-306 | D | H | H | D | H | D | H |
| VI-307 | VI'-307 | VI"-307 | D | H | H | H | D | D | H |
| VI-308 | VI'-308 | VI"-308 | D | H | H | D | D | D | H |
| VI-309 | VI'-309 | VI"-309 | D | H | D | H | H | D | H |
| VI-310 | VI'-310 | VI"-310 | D | H | D | D | H | D | H |
| VI-311 | VI'-311 | VI"-311 | D | H | D | H | D | D | H |
| VI-312 | VI'-312 | VI"-312 | D | H | D | D | D | D | H |
| VI-313 | VI'-313 | VI"-313 | D | D | H | H | H | D | H |
| VI-314 | VI'-314 | VI"-314 | D | D | H | D | H | D | H |
| VI-315 | VI'-315 | VI"-315 | D | D | H | H | D | D | H |
| VI-316 | VI'-316 | VI"-316 | D | D | H | D | D | D | H |
| VI-317 | VI'-317 | VI"-317 | D | D | D | H | H | D | H |
| VI-318 | VI'-318 | VI"-318 | D | D | D | D | H | D | H |
| VI-319 | VI'-319 | VI"-319 | D | D | D | H | D | D | H |
| VI-320 | VI'-320 | VI"-320 | D | D | D | D | D | D | H |
| VI-321 | VI'-321 | VI"-321 | H | H | H | H | H | D | D |
| VI-322 | VI'-322 | VI"-322 | H | H | H | D | H | D | D |
| VI-323 | VI'-323 | VI"-323 | H | H | H | H | D | D | D |
| VI-324 | VI'-324 | VI"-324 | H | H | H | D | D | D | D |
| VI-325 | VI'-325 | VI"-325 | H | H | D | H | H | D | D |
| VI-326 | VI'-326 | VI"-326 | H | H | D | D | H | D | D |
| VI-327 | VI'-327 | VI"-327 | H | H | D | H | D | D | D |
| VI-328 | VI'-328 | VI"-328 | H | H | D | D | D | D | D |
| VI-329 | VI'-329 | VI"-329 | H | D | H | H | H | D | D |
| VI-330 | VI'-330 | VI"-330 | H | D | H | D | H | D | D |
| VI-331 | VI'-331 | VI"-331 | H | D | H | H | D | D | D |
| VI-332 | VI'-332 | VI"-332 | H | D | H | D | D | D | D |
| VI-333 | VI'-333 | VI"-333 | H | D | D | H | H | D | D |
| VI-334 | VI'-334 | VI"-334 | H | D | D | D | H | D | D |
| VI-335 | VI'-335 | VI"-335 | H | D | D | H | D | D | D |
| VI-336 | VI'-336 | VI"-336 | H | D | D | D | D | D | D |
| VI-337 | VI'-337 | VI"-337 | D | H | H | H | H | D | D |
| VI-338 | VI'-338 | VI"-338 | D | H | H | D | H | D | D |
| VI-339 | VI'-339 | VI"-339 | D | H | H | H | D | D | D |
| VI-340 | VI'-340 | VI"-340 | D | H | H | D | D | D | D |
| VI-341 | VI'-341 | VI"-341 | D | H | D | H | H | D | D |
| VI-342 | VI'-342 | VI"-342 | D | H | D | D | H | D | D |
| VI-343 | VI'-343 | VI"-343 | D | H | D | H | D | D | D |
| VI-344 | VI'-344 | VI"-344 | D | H | D | D | D | D | D |
| VI-345 | VI'-345 | VI"-345 | D | D | H | H | H | D | D |
| VI-346 | VI'-346 | VI"-346 | D | D | H | D | H | D | D |
| VI-347 | VI'-347 | VI"-347 | D | D | H | H | D | D | D |
| VI-348 | VI'-348 | VI"-348 | D | D | H | D | D | D | D |
| VI-349 | VI'-349 | VI"-349 | D | D | D | H | H | D | D |
| VI-350 | VI'-350 | VI"-350 | D | D | D | D | H | D | D |
| VI-351 | VI'-351 | VI"-351 | D | D | D | H | D | D | D |
| VI-352 | VI'-352 | VI"-352 | D | D | D | D | D | D | D |

TABLE 8

Compounds of Formulae VI, VI' or VI", wherein $R^{ya}$ is deuterium and $R^{yb}$ is hydrogen.

| Formula VI | Formula VI' | Formula VI" | $R^1/R^{1'}/R^{1''}$ | $R^2/R^{2'}$ | $R^7/R^{7'}$ | $R^8/R^{8'}/R^{8''}$ | $R^9$ | $R^{xa}$ | $R^{xb}$ |
|---|---|---|---|---|---|---|---|---|---|
| VI-353 | VI'-353 | VI"-353 | H | H | H | H | H | H | H |
| VI-354 | VI'-354 | VI"-354 | H | H | H | D | H | H | H |
| VI-355 | VI'-355 | VI"-355 | H | H | H | H | D | H | H |
| VI-356 | VI'-356 | VI"-356 | H | H | H | D | D | H | H |
| VI-357 | VI'-357 | VI"-357 | H | H | D | H | H | H | H |
| VI-358 | VI'-358 | VI"-358 | H | H | D | D | H | H | H |
| VI-359 | VI'-359 | VI"-359 | H | H | D | H | D | H | H |
| VI-360 | VI'-360 | VI"-360 | H | H | D | D | D | H | H |
| VI-361 | VI'-361 | VI"-361 | H | D | H | H | H | H | H |
| VI-362 | VI'-362 | VI"-362 | H | D | H | D | H | H | H |
| VI-363 | VI'-363 | VI"-363 | H | D | H | H | D | H | H |
| VI-364 | VI'-364 | VI"-364 | H | D | H | D | D | H | H |
| VI-365 | VI'-365 | VI"-365 | H | D | D | H | H | H | H |
| VI-366 | VI'-366 | VI"-366 | H | D | D | D | H | H | H |
| VI-367 | VI'-367 | VI"-367 | H | D | D | H | D | H | H |
| VI-368 | VI'-368 | VI"-368 | H | D | D | D | D | H | H |
| VI-369 | VI'-369 | VI"-369 | D | H | H | H | H | H | H |
| VI-370 | VI'-370 | VI"-370 | D | H | H | D | H | H | H |
| VI-371 | VI'-371 | VI"-371 | D | H | H | H | D | H | H |
| VI-372 | VI'-372 | VI"-372 | D | H | H | D | D | H | H |

TABLE 8-continued

Compounds of Formulae VI, VI' or VI'', wherein $R^{ya}$ is deuterium and $R^{yb}$ is hydrogen.

| Formula VI | Formula VI' | Formula VI'' | $R^1/R^{1'}/R^{1''}$ | $R^2/R^{2'}$ | $R^7/R^{7'}$ | $R^8/R^{8'}/R^{8''}$ | $R^9$ | $R^{xa}$ | $R^{xb}$ |
|---|---|---|---|---|---|---|---|---|---|
| VI-373 | VI'-373 | VI''-373 | D | H | D | D | H | H | H |
| VI-374 | VI'-374 | VI''-374 | D | H | D | H | D | H | H |
| VI-375 | VI'-375 | VI''-375 | D | H | H | D | D | H | H |
| VI-376 | VI'-376 | VI''-376 | D | H | D | D | D | H | H |
| VI-377 | VI'-377 | VI''-377 | D | D | H | H | H | H | H |
| VI-378 | VI'-378 | VI''-378 | D | D | D | H | H | H | H |
| VI-379 | VI'-379 | VI''-379 | D | D | H | D | H | H | H |
| VI-380 | VI'-380 | VI''-380 | D | D | H | H | D | H | H |
| VI-381 | VI'-381 | VI''-381 | D | D | D | D | H | H | H |
| VI-382 | VI'-382 | VI''-382 | D | D | D | H | D | H | H |
| VI-383 | VI'-383 | VI''-383 | D | D | H | D | D | H | H |
| VI-384 | VI'-384 | VI''-384 | D | D | D | D | D | H | H |
| VI-385 | VI'-385 | VI''-385 | H | H | H | H | H | H | D |
| VI-386 | VI'-386 | VI''-386 | H | H | D | H | H | H | D |
| VI-387 | VI'-387 | VI''-387 | H | H | H | D | H | H | D |
| VI-388 | VI'-388 | VI''-388 | H | H | H | H | D | H | D |
| VI-389 | VI'-389 | VI''-389 | H | H | D | D | H | H | D |
| VI-390 | VI'-390 | VI''-390 | H | H | D | H | D | H | D |
| VI-391 | VI'-391 | VI''-391 | H | H | H | D | D | H | D |
| VI-392 | VI'-392 | VI''-392 | H | H | D | D | D | H | D |
| VI-393 | VI'-393 | VI''-393 | H | D | H | H | H | H | D |
| VI-394 | VI'-394 | VI''-394 | H | D | D | H | H | H | D |
| VI-395 | VI'-395 | VI''-395 | H | D | H | D | H | H | D |
| VI-396 | VI'-396 | VI''-396 | H | D | H | H | D | H | D |
| VI-397 | VI'-397 | VI''-397 | H | D | D | D | H | H | D |
| VI-398 | VI'-398 | VI''-398 | H | D | D | H | D | H | D |
| VI-399 | VI'-399 | VI''-399 | H | D | H | D | D | H | D |
| VI-400 | VI'-400 | VI''-400 | H | D | D | D | D | H | D |
| VI-401 | VI'-401 | VI''-401 | D | H | H | H | H | H | D |
| VI-402 | VI'-402 | VI''-402 | D | H | D | H | H | H | D |
| VI-403 | VI'-403 | VI''-403 | D | H | H | D | H | H | D |
| VI-404 | VI'-404 | VI''-404 | D | H | H | H | D | H | D |
| VI-405 | VI'-405 | VI''-405 | D | H | D | D | H | H | D |
| VI-406 | VI'-406 | VI''-406 | D | H | D | H | D | H | D |
| VI-407 | VI'-407 | VI''-407 | D | H | H | D | D | H | D |
| VI-408 | VI'-408 | VI''-408 | D | H | D | D | D | H | D |
| VI-409 | VI'-409 | VI''-409 | D | D | H | H | H | H | D |
| VI-410 | VI'-410 | VI''-410 | D | D | D | H | H | H | D |
| VI-411 | VI'-411 | VI''-411 | D | D | H | D | H | H | D |
| VI-412 | VI'-412 | VI''-412 | D | D | H | H | D | H | D |
| VI-413 | VI'-413 | VI''-413 | D | D | D | D | H | H | D |
| VI-414 | VI'-414 | VI''-414 | D | D | D | H | D | H | D |
| VI-415 | VI'-415 | VI''-415 | D | D | H | D | D | H | D |
| VI-416 | VI'-416 | VI''-416 | D | D | D | D | D | H | D |
| VI-417 | VI'-417 | VI''-417 | H | H | H | H | H | D | H |
| VI-418 | VI'-418 | VI''-418 | H | H | D | H | H | D | H |
| VI-419 | VI'-419 | VI''-419 | H | H | H | D | H | D | H |
| VI-420 | VI'-420 | VI''-420 | H | H | H | H | D | D | H |
| VI-421 | VI'-421 | VI''-421 | H | H | D | D | H | D | H |
| VI-422 | VI'-422 | VI''-422 | H | H | D | H | D | D | H |
| VI-423 | VI'-423 | VI''-423 | H | H | H | D | D | D | H |
| VI-424 | VI'-424 | VI''-424 | H | H | D | D | D | D | H |
| VI-425 | VI'-425 | VI''-425 | H | D | H | H | H | D | H |
| VI-426 | VI'-426 | VI''-426 | H | D | D | H | H | D | H |
| VI-427 | VI'-427 | VI''-427 | H | D | H | D | H | D | H |
| VI-428 | VI'-428 | VI''-428 | H | D | H | H | D | D | H |
| VI-429 | VI'-429 | VI''-429 | H | D | D | D | H | D | H |
| VI-430 | VI'-430 | VI''-430 | H | D | D | H | D | D | H |
| VI-431 | VI'-431 | VI''-431 | H | D | H | D | D | D | H |
| VI-432 | VI'-432 | VI''-432 | H | D | D | D | D | D | H |
| VI-433 | VI'-433 | VI''-433 | D | H | H | H | H | D | H |
| VI-434 | VI'-434 | VI''-434 | D | H | D | H | H | D | H |
| VI-435 | VI'-435 | VI''-435 | D | H | H | D | H | D | H |
| VI-436 | VI'-436 | VI''-436 | D | H | H | H | D | D | H |
| VI-437 | VI'-437 | VI''-437 | D | H | D | D | H | D | H |
| VI-438 | VI'-438 | VI''-438 | D | H | D | H | D | D | H |
| VI-439 | VI'-439 | VI''-439 | D | H | H | D | D | D | H |
| VI-440 | VI'-440 | VI''-440 | D | H | D | D | D | D | H |
| VI-441 | VI'-441 | VI''-441 | D | D | H | H | H | D | H |
| VI-442 | VI'-442 | VI''-442 | D | D | D | H | H | D | H |
| VI-443 | VI'-443 | VI''-443 | D | D | H | D | H | D | H |
| VI-444 | VI'-444 | VI''-444 | D | D | H | H | D | D | H |
| VI-445 | VI'-445 | VI''-445 | D | D | D | D | H | D | H |
| VI-446 | VI'-446 | VI''-446 | D | D | D | H | D | D | H |
| VI-447 | VI'-447 | VI''-447 | D | D | H | D | D | D | H |
| VI-448 | VI'-448 | VI''-448 | D | D | D | D | D | D | H |
| VI-449 | VI'-449 | VI''-449 | H | H | H | H | H | D | D |
| VI-450 | VI'-450 | VI''-450 | H | H | D | H | H | D | D |
| VI-451 | VI'-451 | VI''-451 | H | H | H | D | H | D | D |
| VI-452 | VI'-452 | VI''-452 | H | H | H | H | D | D | D |
| VI-453 | VI'-453 | VI''-453 | H | H | D | D | H | D | D |
| VI-454 | VI'-454 | VI''-454 | H | H | D | H | D | D | D |
| VI-455 | VI'-455 | VI''-455 | H | H | H | D | D | D | D |
| VI-456 | VI'-456 | VI''-456 | H | H | D | D | D | D | D |
| VI-457 | VI'-457 | VI''-457 | H | D | H | H | H | D | D |
| VI-458 | VI'-458 | VI''-458 | H | D | D | H | H | D | D |
| VI-459 | VI'-459 | VI''-459 | H | D | H | D | H | D | D |
| VI-460 | VI'-460 | VI''-460 | H | D | H | H | D | D | D |
| VI-461 | VI'-461 | VI''-461 | H | D | D | D | H | D | D |
| VI-462 | VI'-462 | VI''-462 | H | D | D | H | D | D | D |
| VI-463 | VI'-463 | VI''-463 | H | D | H | D | D | D | D |
| VI-464 | VI'-464 | VI''-464 | H | D | D | D | D | D | D |
| VI-465 | VI'-465 | VI''-465 | D | H | H | H | H | D | D |
| VI-466 | VI'-466 | VI''-466 | D | H | D | H | H | D | D |
| VI-467 | VI'-467 | VI''-467 | D | H | H | D | H | D | D |
| VI-468 | VI'-468 | VI''-468 | D | H | H | H | D | D | D |
| VI-469 | VI'-469 | VI''-469 | D | H | D | D | H | D | D |
| VI-470 | VI'-470 | VI''-470 | D | H | D | H | D | D | D |
| VI-471 | VI'-471 | VI''-471 | D | H | H | D | D | D | D |
| VI-472 | VI'-472 | VI''-472 | D | H | D | D | D | D | D |
| VI-473 | VI'-473 | VI''-473 | D | D | H | H | H | D | D |
| VI-474 | VI'-474 | VI''-474 | D | D | D | H | H | D | D |
| VI-475 | VI'-475 | VI''-475 | D | D | H | D | H | D | D |
| VI-476 | VI'-476 | VI''-476 | D | D | H | H | D | D | D |
| VI-477 | VI'-477 | VI''-477 | D | D | D | D | H | D | D |
| VI-478 | VI'-478 | VI''-478 | D | D | D | H | D | D | D |
| VI-479 | VI'-479 | VI''-479 | D | D | H | D | D | D | D |
| VI-480 | VI'-480 | VI''-480 | D | D | D | D | D | D | D |

In some embodiments, each of $R^{xa}$, $R^{xb}$, $R^{ya}$, and $R^{yb}$ is deuterium. In some embodiments, each of $R^{xa}$, $R^{xb}$, $R^{ya}$, and $R^{yb}$ is hydrogen. Accordingly, in some embodiments, the present invention provides a compound of Formulae VII, VII' or VII'':

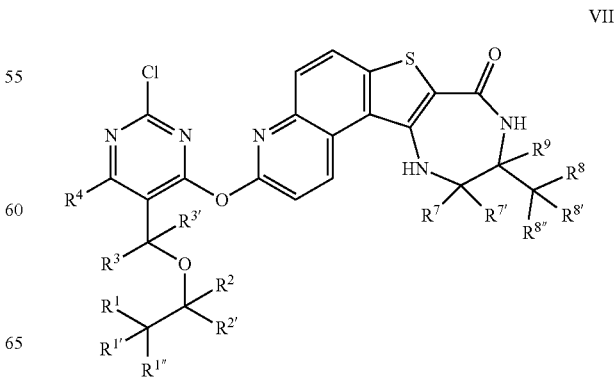

VII

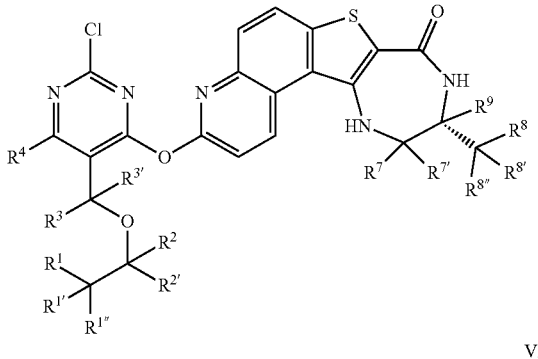

VII'

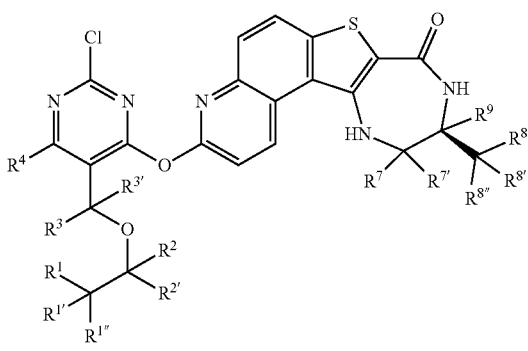

VII"

or a pharmaceutically acceptable salt thereof, wherein each of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, and $R^9$, is as defined above and described herein, provided that at least one of $R^1$, $R^{1'}$, $R^{1''}$, $R^2$, $R^{2'}$, $R^3$, $R^{3'}$, $R^4$, $R^7$, $R^{7'}$, $R^8$, $R^{8'}$, $R^{8''}$, and $R^9$ is deuterium.

In some embodiments of Formulae VII, VII' or VII", at least one of $R^1$, $R^{1'}$, $R^{1''}$, $R^2$, $R^{2'}$, $R^3$, $R^{3'}$, $R^4$, $R^{7'}$, $R^{7'}$, $R^8$, $R^{8'}$, $R^{8''}$, and $R^9$ is deuterium. In some embodiments of Formulae VII, VII' or VII", the compound is selected from those of Table 13, Table 14, and Table 15:

TABLE 13

Compounds of Formulae VII, VII' or VII", wherein each of $R^3$, $R^{3'}$, and $R^4$ are deuterium.

| Formula VII | Formula VII' | Formula VII" | $R^1/R^{1'}/R^{1''}$ | $R^2/R^{2'}$ | $R^7/R^{7'}$ | $R^8/R^{8'}/R^{8''}$ | $R^9$ |
|---|---|---|---|---|---|---|---|
| VII-1 | VII'-1 | VII"-1 | H | H | H | H | H |
| VII-2 | VII'-2 | VII"-2 | H | H | D | H | H |
| VII-3 | VII'-3 | VII"-3 | H | H | H | D | H |
| VII-4 | VII'-4 | VII"-4 | H | H | H | H | D |
| VII-5 | VII'-5 | VII"-5 | H | H | D | D | H |
| VII-6 | VII'-6 | VII"-6 | H | H | D | H | D |
| VII-7 | VII'-7 | VII"-7 | H | H | H | D | D |
| VII-8 | VII'-8 | VII"-8 | H | H | D | D | D |
| VII-9 | VII'-9 | VII"-9 | H | D | H | H | H |
| VII-10 | VII'-10 | VII"-10 | H | D | D | H | H |
| VII-11 | VII'-11 | VII"-11 | H | D | H | D | H |
| VII-12 | VII'-12 | VII"-12 | H | D | H | H | D |
| VII-13 | VII'-13 | VII"-13 | H | D | D | D | H |
| VII-14 | VII'-14 | VII"-14 | H | D | D | H | D |
| VII-15 | VII'-15 | VII"-15 | H | D | H | D | D |
| VII-16 | VII'-16 | VII"-16 | H | D | D | D | D |
| VII-17 | VII'-17 | VII"-17 | D | H | H | H | H |
| VII-18 | VII'-18 | VII"-18 | D | H | D | H | H |
| VII-19 | VII'-19 | VII"-19 | D | H | H | D | H |
| VII-20 | VII'-20 | VII"-20 | D | H | H | H | D |
| VII-21 | VII'-21 | VII"-21 | D | H | D | D | H |
| VII-22 | VII'-22 | VII"-22 | D | H | D | H | D |

TABLE 13-continued

Compounds of Formulae VII, VII' or VII", wherein each of $R^3$, $R^{3'}$, and $R^4$ are deuterium.

| Formula VII | Formula VII' | Formula VII" | $R^1/R^{1'}/R^{1''}$ | $R^2/R^{2'}$ | $R^7/R^{7'}$ | $R^8/R^{8'}/R^{8''}$ | $R^9$ |
|---|---|---|---|---|---|---|---|
| VII-23 | VII'-23 | VII"-23 | D | H | H | D | D |
| VII-24 | VII'-24 | VII"-24 | D | H | D | D | D |
| VII-25 | VII'-25 | VII"-25 | D | D | H | H | H |
| VII-26 | VII'-26 | VII"-26 | D | D | D | H | H |
| VII-27 | VII'-27 | VII"-27 | D | D | H | D | H |
| VII-28 | VII'-28 | VII"-28 | D | D | H | H | D |
| VII-29 | VII'-29 | VII"-29 | D | D | D | D | H |
| VII-30 | VII'-30 | VII"-30 | D | D | D | H | D |
| VII-31 | VII'-31 | VII"-31 | D | D | H | D | D |
| VII-32 | VII'-32 | VII"-32 | D | D | D | D | D |

TABLE 14

Compounds of Formulae VII, VII' or VII", wherein each of $R^3$ and $R^{3'}$ is deuterium and $R^4$ is hydrogen.

| Formula VII | Formula VII' | Formula VII" | $R^1/R^{1'}/R^{1''}$ | $R^2/R^{2'}$ | $R^7/R^{7'}$ | $R^8/R^{8'}/R^{8''}$ | $R^9$ |
|---|---|---|---|---|---|---|---|
| VII-33 | VII'-33 | VII"-33 | H | H | H | H | H |
| VII-34 | VII'-34 | VII"-34 | H | H | D | H | H |
| VII-35 | VII'-35 | VII"-35 | H | H | H | D | H |
| VII-36 | VII'-36 | VII"-36 | H | H | H | H | D |
| VII-37 | VII'-37 | VII"-37 | H | H | D | D | H |
| VII-38 | VII'-38 | VII"-38 | H | H | D | H | D |
| VII-39 | VII'-39 | VII"-39 | H | H | H | D | D |
| VII-40 | VII'-40 | VII"-40 | H | H | D | D | D |
| VII-41 | VII'-41 | VII"-41 | H | D | H | H | H |
| VII-42 | VII'-42 | VII"-42 | H | D | D | H | H |
| VII-43 | VII'-43 | VII"-43 | H | D | H | D | H |
| VII-44 | VII'-44 | VII"-44 | H | D | H | H | D |
| VII-45 | VII'-45 | VII"-45 | H | D | D | D | H |
| VII-46 | VII'-46 | VII"-46 | H | D | D | H | D |
| VII-47 | VII'-47 | VII"-47 | H | D | H | D | D |
| VII-48 | VII'-48 | VII"-48 | H | D | D | D | D |
| VII-49 | VII'-49 | VII"-49 | D | H | H | H | H |
| VII-50 | VII'-50 | VII"-50 | D | H | D | H | H |
| VII-51 | VII'-51 | VII"-51 | D | H | H | D | H |
| VII-52 | VII'-52 | VII"-52 | D | H | H | H | D |
| VII-53 | VII'-53 | VII"-53 | D | H | D | D | H |
| VII-54 | VII'-54 | VII"-54 | D | H | D | H | D |
| VII-55 | VII'-55 | VII"-55 | D | H | H | D | D |
| VII-56 | VII'-56 | VII"-56 | D | H | D | D | D |
| VII-57 | VII'-57 | VII"-57 | D | D | H | H | H |
| VII-58 | VII'-58 | VII"-58 | D | D | D | H | H |
| VII-59 | VII'-59 | VII"-59 | D | D | H | D | H |
| VII-60 | VII'-60 | VII"-60 | D | D | H | H | D |
| VII-61 | VII'-61 | VII"-61 | D | D | D | D | H |
| VII-62 | VII'-62 | VII"-62 | D | D | D | H | D |
| VII-63 | VII'-63 | VII"-63 | D | D | H | D | D |
| VII-64 | VII'-64 | VII"-64 | D | D | D | D | D |

TABLE 15

Compounds of Formulae VII, VII' or VII", wherein each of $R^3$ and $R^{3'}$ is hydrogen and $R^4$ is deuterium.

| Formula VII | Formula VII' | Formula VII" | $R^1/R^{1'}/R^{1''}$ | $R^2/R^{2'}$ | $R^7/R^{7'}$ | $R^8/R^{8'}/R^{8''}$ | $R^9$ |
|---|---|---|---|---|---|---|---|
| VII-65 | VII'-65 | VII"-65 | H | H | H | H | H |
| VII-66 | VII'-66 | VII"-66 | H | H | D | H | H |
| VII-67 | VII'-67 | VII"-67 | H | H | H | D | H |
| VII-68 | VII'-68 | VII"-68 | H | H | H | H | D |
| VII-69 | VII'-69 | VII"-69 | H | H | D | D | H |
| VII-70 | VII'-70 | VII"-70 | H | H | D | H | D |
| VII-71 | VII'-71 | VII"-71 | H | H | H | D | D |
| VII-72 | VII'-72 | VII"-72 | H | H | D | D | D |
| VII-73 | VII'-73 | VII"-73 | H | D | H | H | H |

TABLE 15-continued

Compounds of Formulae VII, VII' or VII", wherein each of $R^3$ and $R^{3'}$ is hydrogen and $R^4$ is deuterium.

| Formula VII | Formula VII' | Formula VII" | $R^1/R^{1'}/R^{1''}$ | $R^2/R^{2'}$ | $R^7/R^{7'}$ | $R^8/R^{8'}/R^{8''}$ | $R^9$ |
|---|---|---|---|---|---|---|---|
| VII-74 | VII'-74 | VII"-74 | H | D | D | H | H |
| VII-75 | VII'-75 | VII"-75 | H | D | H | D | H |
| VII-76 | VII'-76 | VII"-76 | H | D | H | H | D |
| VII-77 | VII'-77 | VII"-77 | H | D | D | D | H |
| VII-78 | VII'-78 | VII"-78 | H | D | D | H | D |
| VII-79 | VII'-79 | VII"-79 | H | D | H | D | D |
| VII-80 | VII'-80 | VII"-80 | H | D | D | D | D |
| VII-81 | VII'-81 | VII"-81 | D | H | H | H | H |
| VII-82 | VII'-82 | VII"-82 | D | H | D | H | H |
| VII-83 | VII'-83 | VII"-83 | D | H | H | D | H |
| VII-84 | VII'-84 | VII"-84 | D | H | H | H | D |
| VII-85 | VII'-85 | VII"-85 | D | H | D | D | H |
| VII-86 | VII'-86 | VII"-86 | D | H | D | H | D |
| VII-87 | VII'-87 | VII"-87 | D | H | H | D | D |
| VII-88 | VII'-88 | VII"-88 | D | H | D | D | D |
| VII-89 | VII'-89 | VII"-89 | D | D | H | H | H |
| VII-90 | VII'-90 | VII"-90 | D | D | D | H | H |
| VII-91 | VII'-91 | VII"-91 | D | D | H | D | H |
| VII-92 | VII'-92 | VII"-92 | D | D | H | H | D |
| VII-93 | VII'-93 | VII"-93 | D | D | D | D | H |
| VII-94 | VII'-94 | VII"-94 | D | D | D | H | D |
| VII-95 | VII'-95 | VII"-95 | D | D | H | D | D |
| VII-96 | VII'-96 | VII"-96 | D | D | D | D | D |

In some embodiments, each of each of $R^3$, $R^{3'}$, $R^4$, $R^{xa}$, $R^{xb}$, $R^{ya}$, and $R^{yb}$ is deuterium. Accordingly, in some embodiments, the present invention provides a compound of Formulae VIII, VIII' or VIII":

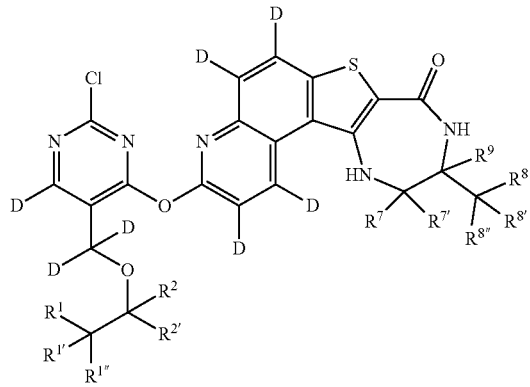

VIII

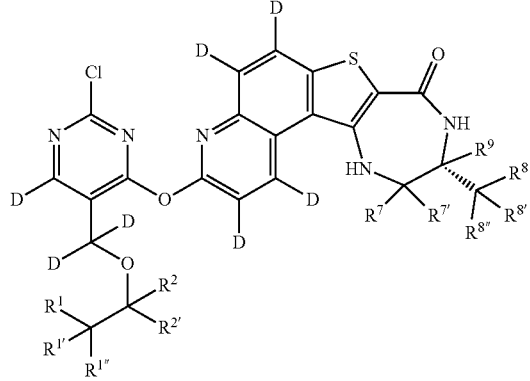

VIII'

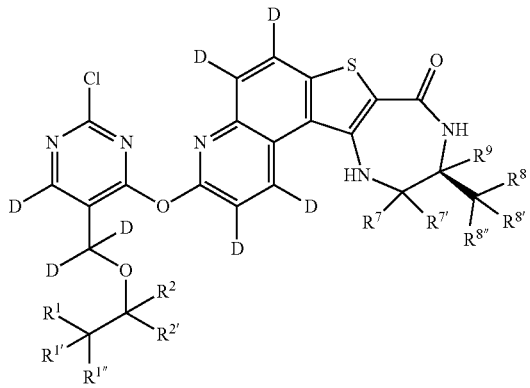

VIII"

In some embodiments of Formulae VIII, VIII' or VIII", the compound is selected from those of Table 16:

TABLE 16

Compounds of Formulae VIII, VIII' or VIII".

| Formula VIII | Formula VIII' | Formula VIII" | $R^1/R^{1'}/R^{1''}$ | $R^2/R^{2'}$ | $R^7/R^{7'}$ | $R^8/R^{8'}/R^{8''}$ | $R^9$ |
|---|---|---|---|---|---|---|---|
| VIII-1 | VIII'-1 | VIII"-1 | H | H | H | H | H |
| VIII-2 | VIII'-2 | VIII"-2 | H | H | D | H | H |
| VIII-3 | VIII'-3 | VIII"-3 | H | H | H | D | H |
| VIII-4 | VIII'-4 | VIII"-4 | H | H | H | H | D |
| VIII-5 | VIII'-5 | VIII"-5 | H | H | D | D | H |
| VIII-6 | VIII'-6 | VIII"-6 | H | H | D | H | D |
| VIII-7 | VIII'-7 | VIII"-7 | H | H | D | D | H |
| VIII-8 | VIII'-8 | VIII"-8 | H | H | D | D | D |
| VIII-9 | VIII'-9 | VIII"-9 | H | D | H | H | H |
| VIII-10 | VIII'-10 | VIII"-10 | H | D | H | H | H |
| VIII-11 | VIII'-11 | VIII"-11 | H | D | H | D | H |
| VIII-12 | VIII'-12 | VIII"-12 | H | D | H | H | D |
| VIII-13 | VIII'-13 | VIII"-13 | H | D | D | D | H |
| VIII-14 | VIII'-14 | VIII"-14 | H | D | D | H | D |
| VIII-15 | VIII'-15 | VIII"-15 | H | D | H | D | D |
| VIII-16 | VIII'-16 | VIII"-16 | H | D | D | D | D |
| VIII-17 | VIII'-17 | VIII"-17 | D | H | H | H | H |
| VIII-18 | VIII'-18 | VIII"-18 | D | H | D | H | H |
| VIII-19 | VIII'-19 | VIII"-19 | D | H | H | D | H |
| VIII-20 | VIII'-20 | VIII"-20 | D | H | H | H | D |
| VIII-21 | VIII'-21 | VIII"-21 | D | H | D | D | H |
| VIII-22 | VIII'-22 | VIII"-22 | D | H | D | H | D |
| VIII-23 | VIII'-23 | VIII"-23 | D | H | H | D | D |
| VIII-24 | VIII'-24 | VIII"-24 | D | H | D | D | D |
| VIII-25 | VIII'-25 | VIII"-25 | D | D | H | H | H |
| VIII-26 | VIII'-26 | VIII"-26 | D | D | D | H | H |
| VIII-27 | VIII'-27 | VIII"-27 | D | D | H | D | H |
| VIII-28 | VIII'-28 | VIII"-28 | D | D | H | H | D |
| VIII-29 | VIII'-29 | VIII"-29 | D | D | D | D | H |
| VIII-30 | VIII'-30 | VIII"-30 | D | D | D | H | D |
| VIII-31 | VIII'-31 | VIII"-31 | D | D | H | D | D |
| VIII-32 | VIII'-32 | VIII"-32 | D | D | D | D | D |

In some embodiments, the present invention provides compounds comprising one, two, three, four, five, six, seven, eight, nine, ten, eleven, twelve, thirteen, fourteen, fifteen, sixteen, seventeen, or eighteen deuterium atoms. In some embodiments, provided compounds comprise deuterium in an amount of about 6%, or about 11%, or about 17%, or about 22%, or about 28%, or about 33%, or about 39%, or about 44%, or about 50%, or about 56%, or about 61%, or about 67%, or about 72%, or about 78%, or about 83%, or about 89%, or about 94%, or about 100%. In some embodiments, the present invention provides deuterium-enriched compounds according to Table 17:

TABLE 17

Deuterium Enriched Compounds of Formula I, I' or I".

| Number of Deuterium Atoms | Percent Enrichment |
| --- | --- |
| 1 | 5.6 |
| 2 | 11.1 |
| 3 | 16.7 |
| 4 | 22.2 |
| 5 | 27.8 |
| 6 | 33.3 |
| 7 | 38.9 |
| 8 | 44.4 |
| 9 | 50.0 |
| 10 | 55.6 |
| 11 | 61.1 |
| 12 | 66.7 |
| 13 | 72.2 |
| 14 | 77.8 |
| 15 | 83.3 |
| 16 | 88.9 |
| 17 | 94.4 |
| 18 | 100 |

In some embodiments, the present invention provides a compound selected from any of Tables 1-16 above, or a pharmaceutically acceptable salt thereof.

In some embodiments, the present inventions provides a compound selected from any of those depicted below:

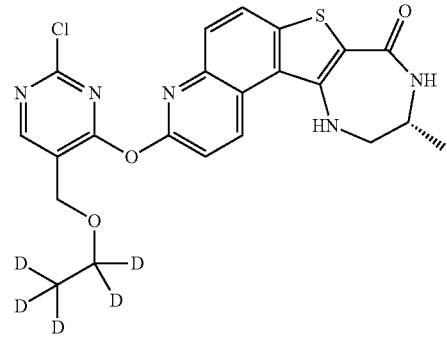

I'-1

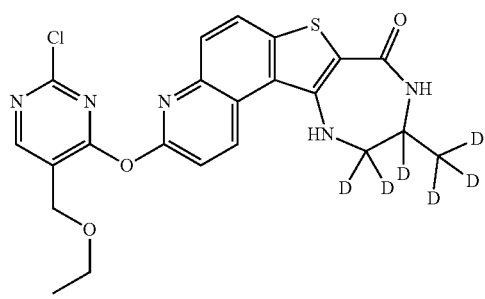

I-2

In some embodiments, the present inventions provides a compound selected from any of those depicted below:

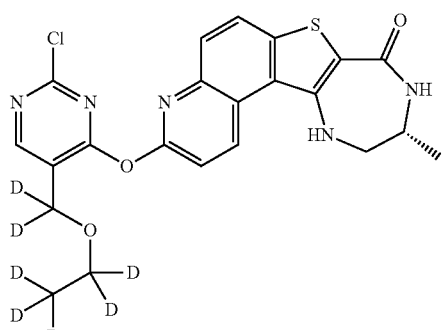

I'-3 or

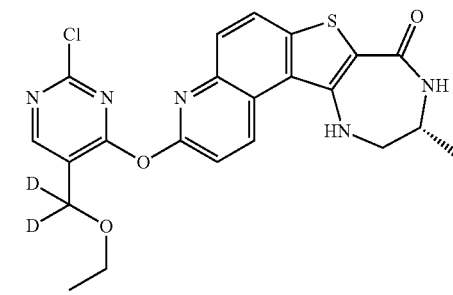

I'-4

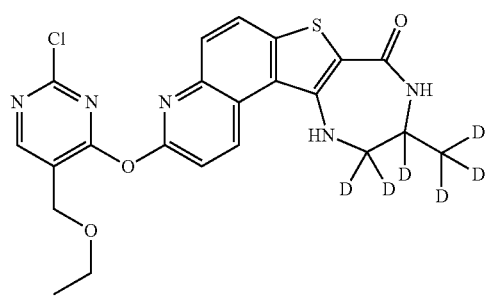

I-2

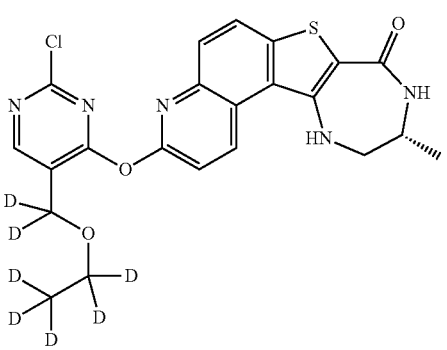

I'-3 or

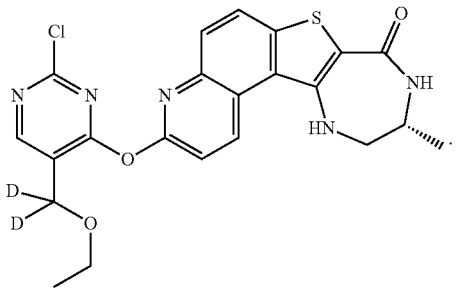

In some embodiments, the present invention provides an isolated or purified compound of any of Formulae I, I', I", II, II', II"', III, III', III"', IV, IV', IV"', V, V', V"', VI, VI', VI"', VII, VII', VII"', VIII, VIII', or VIII". In some embodiments of any of Formulae I, I', II, II', III, III', V, V', VII, or VII', the compound is other than:

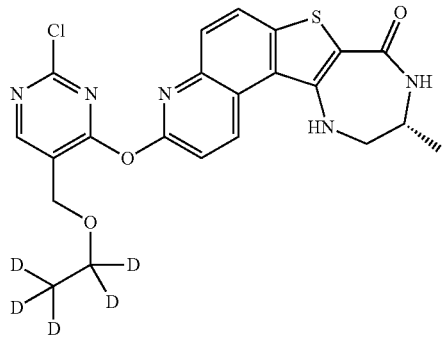

Compounds of Formulae I, I', I", II, II', II"', III, III', III"', IV, IV', IV"', V, V', V"', VI, VI', VI"', VII, VII', VII"', VIII, VIII', or VIII" contain a chloropyrimidine moiety which is capable of and particularly suitable for covalently binding to a key cysteine residue in the binding domain of MK2. In certain embodiments, compounds of the present invention having a chloropyrimidine group target Cys140 of MK2. In certain embodiments, Cys140 of MK2 is characterized in that Cys140 is the cysteine embedded in the following amino acid sequence of MK2:

SEQ ID NO. 1:
MLSNSQGQSPPVPFPAPAPPPQPPTPALPHPPAQPPPPPPQQFPQFHVKSG

LQIKKNAIIDDYKVTSQVLGLGINGKVLQIFNKRTQEKFALKMLQDCPKAR

REVELHWRASQCPHIVRIVDVYENLYAGRKCLLIVME<u>C</u>LDGGELFSRIQDR

GDQAFTEREASEIMKSIGEAIQYLHSINIAHRDVKPENLLYTSKRPNAILK

LTDFGFAKETTSHNSLTTPCYTPYYVAPEVLGPEKYDKSCDMWSLGVIMYI

LLCGYPPFYSNHGLAISPGMKTRIRMGQYEFPNPEWSEVSEEVKMLIRNLL

KTEPTQRMTITEFMNHPWIMQSTKVPQTPLHTSRVLKEDKERWEDVKEEMT

SALATMRVDYEQIKIKKIEDASNPLLLKRRKKARALEAAALAH.

For the purpose of clarity, Cys140 is provided in the abbreviated amino acid sequence below:

SEQ ID NO. 2:
NLYAGRKCLLIVME<u>C(140)</u>LDGGELFSRIQDR.

In both SEQ ID NOS. 1 and 2, Cysteine 140 is highlighted in bold with underlining.

Thus, in some embodiments, compounds of the present invention having a chloropyrimidine group are capable of covalently binding to a cysteine residue of MK2, thereby irreversibly inhibiting the enzyme. In some embodiments, the cysteine residue is Cys140.

In some embodiments, provided compounds are irreversible inhibitors of MK2, or a mutant thereof, and therefore useful for treating one or disorders as described herein.

4. Uses, Formulation and Administration

Pharmaceutically Acceptable Compositions

According to another embodiment, the invention provides a composition comprising a compound of this invention or a pharmaceutically acceptable salt thereof and a pharmaceutically acceptable carrier, adjuvant, or vehicle. In certain embodiments, the amount of compound in compositions of this invention is such that it is effective to measurably inhibit MK2, or a mutant thereof, in a biological sample or in a patient. In certain embodiments, a composition of this invention is formulated for administration to a patient in need of such composition. In some embodiments, a composition of this invention is formulated for oral administration to a patient.

Compounds and compositions, according to method of the present invention, are administered using any amount and any route of administration effective for treating or lessening the severity of a disorder provided herein (i.e., an MK2-mediated disease or disorder). The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage.

Compositions of the present invention may be administered orally, parenterally, by inhalation spray, topically, rectally, nasally, buccally, vaginally, intraperitoneally, intracisternally or via an implanted reservoir. In some embodiments, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, provided pharmaceutically acceptable compositions are formulated for oral administration. Such formulations may be administered with or without food. In some embodiments, pharmaceutically acceptable compositions of this invention are administered without food. In other embodiments, pharmaceutically acceptable compositions of this invention are administered with food. Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutically Acceptable Compositions

Compounds and compositions described herein are generally useful for the inhibition of kinase activity of one or more enzymes. Examples of kinases that are inhibited by the compounds and compositions described herein and against which the methods described herein are useful include MK2, or a mutant thereof.

The activity of a compound utilized in this invention as an inhibitor of a MK2 kinase, or a mutant thereof, may be assayed in vitro, in vivo or in a cell line. In vitro assays include assays that determine inhibition of either the phosphorylation activity and/or the subsequent functional consequences, or ATPase activity of activated MK2 kinase, or a mutant thereof. Alternate in vitro assays quantitate the ability of the test compound to bind to MK2. Inhibitor binding may be measured by radiolabeling the test compound prior to binding, isolating the test compound/MK2 complex and determining the amount of radiolabel bound. Alternatively, inhibitor binding may be determined by running a competition experiment where test compounds are incubated with MK2 kinase bound to known radioligands. Detailed conditions for assaying a compound utilized in this invention as an inhibitor of MK2, or a mutant thereof, are set forth in the Examples, below.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting MK2 kinase, or a mutant thereof, activity in a biological sample comprising the step of contacting said biological sample with a compound of this invention, or a composition comprising said compound. In certain embodiments, the invention relates to a method of irreversibly inhibiting MK2 kinase, or a mutant thereof, activity in a biological sample comprising the step of contacting said biological sample with a compound of this invention, or a composition comprising said compound.

According to another embodiment, the invention relates to a method of inhibiting MK2 kinase, or a mutant thereof, activity in a patient comprising the step of administering to said patient a compound of the present invention, or a composition comprising said compound. According to certain embodiments, the invention relates to a method of irreversibly inhibiting MK2 kinase, or a mutant thereof, activity in a patient comprising the step of administering to said patient a compound of the present invention, or a composition comprising said compound. In other embodiments, the present invention provides a method for treating an MK2-mediated disease or disorder, in a patient in need thereof, comprising the step of administering to said patient a compound according to the present invention or pharmaceutically acceptable composition thereof. Such disorders are described in detail herein.

MK2 Kinase

MAP kinase-activated protein kinase 2 ("MK2") is an enzyme that in humans is encoded by the MAPKAPK2 gene. The MAPKAPK2 gene encodes a member of the Ser/Thr protein kinase family and two transcript variants encoding two different isoforms have been found. MK2 is regulated through direct phosphorylation by p38 MAP kinase.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS.

MK2 is known to be involved in many cellular processes including stress and inflammatory responses, nuclear export, gene expression regulation and cell proliferation. Indeed, MK2 regulates, by a post-transcriptional mechanism, biosynthesis of tumor necrosis factor α (TNFα) that is overproduced in inflammatory diseases such as rheumatoid arthritis and inflammatory bowel disease. See Natesan et al., *J. Med. Chem.* 2012, 55, 2035-2047.

Inhibition of Hsp27 phosphorylation occurs by inhibiting the formation of the p38 kinase-MK2-Hsp27 signaling complex. Phosphorylation of Hsp27 is the penultimate event in a complex signaling cascade that occurs in response to extracellular stimuli. See Zheng et al., *The Journal of Biological Chemistry*, vol. 281, no. 48, 37215-37226, Dec. 1, 2006. Hsp27 usually exists as oligomers and plays a role in regulation of many cellular functions such as inhibition of the death receptor-mediated apoptosis, promotion of proper refolding of denatured proteins by acting as a molecular chaperone, and regulation of cytoskeleton. The presence of MK2 is a necessary condition for the formation of p38 kinase-MK2-Hsp27 signaling complex in cells. See Zheng et al., *The Journal of Biological Chemistry*, vol. 281, no. 48, 37215-37226, Dec. 1, 2006.

Evidence suggests that many signaling proteins form multimeric complexes. See Zheng et al., *The Journal of Biological Chemistry*, vol. 281, no. 48, 37215-37226, Dec. 1, 2006. One such complex is the Hsp27/Akt (a serine/threonine kinase) dimer, which forms in the cytoplasm of a cell. Another complex is formed between MK2 and p38. See Ben-Levy et al., *Current Biology* 1998, 8:1049-1057; Natesan et al., *J. Med. Chem.* 2012, 55, 2035-2047; Zheng et al., *The Journal of Biological Chemistry*, vol. 281, no. 48, 37215-37226, Dec. 1, 2006.

In unstimulated conditions, inactive p38 and unphosphorylated MK2 form such dimer in the nucleus of a cell. Upon activation, p38 phosphorylates MK2, thereby inducing a conformational change of the autoinhibitory domain of MK2 and exposing the active site for substrate binding. Once MK2 is phosphorylated, the p38-MK2 dimer is translocated to the cytoplasm, where it forms a quaternary complex with the Hsp27-Akt dimer. See Zheng et al., *The Journal of Biological Chemistry*, vol. 281, no. 48, 37215-37226, Dec. 1, 2006. Hsp27 is then phosphorylated by MK2, resulting in degradation of the quaternary complex and the release of p-Hsp27 monomers and dimers. Because inhibition of MK2 blocks phosphorylation of Hsp27, without wishing to be bound by theory, it is believed that inhibition of MK2 prevents degradation of the p38-MK2-Akt-Hsp27 quaternary complex, thereby altering downstream effects. Consequent to the inhibition of quaternary complex degradation, the amount of quaternary complex would thereby increase. Moreover, the equilibrium of p38 and MK2 between the cytoplasm and nucleus would be shifted towards the cytoplasm.

Interestingly, transport of the MK2/p38 complex out of the nucleus does not require catalytically active MK2, as the active site mutant, Asp207Ala, is still transported to the cytoplasm. Phosphorylation of human MK2 by p38 on residues T222, S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

Diseases or disorders associated with MK2 that are treated by compounds of the present invention include autoimmune disorders, chronic inflammatory disorders, acute inflammatory disorders, auto-inflammatory disorders, fibrotic disorders, metabolic disorders, neoplasias, or cardiovascular or cerebrovascular disorders. Thus, in some embodiments, the present invention provides a method for treating an MK2-mediated disease or disorder in a patient in need thereof, wherein said method comprises administering to said patient a therapeutically effective amount of a provided compound, or composition thereof. Such MK2-mediated diseases or disorders include, but are not limited to those described herein.

In some embodiments, the MK2-mediated disease or disorder is an autoimmune disorder, chronic and/or acute inflammatory disorder, and/or auto-inflammatory disorder. Exemplary autoimmune and/or inflammatory and/or auto-inflammatory disorders include: inflammatory bowel diseases (for example, ulcerative colitis or Crohn's disease), multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic syndrome, acute and chronic pancreatitis, atherosclerosis, gout, ankylosing spondylitis, fibrotic disorders (for example, hepatic fibrosis or idiopathic pulmonary fibrosis), nephropathy, sarcoidosis, scleroderma, anaphylaxis, diabetes (for example, diabetes mellitus type 1 or diabetes mellitus type 2), diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes (for example, temporal, Takayasu's and giant cell arteritis, Behget's disease or Wegener's granulomatosis), vitiligo, secondary hematologic manifestation of autoimmune diseases (for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (for example, Meniere's disease), Goodpasture's syndrome, Graves' disease, HW-related autoimmune syndromes, Guillian-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction (for example, graft vs. host disease), allograft rejections (for example, acute allograft rejection or chronic allograft rejection), early transplantation rejection (for example, acute allograft rejection), reperfusion injury, pain (for example, acute pain, chronic pain, neuropathic pain, or fibromyalgia), chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

In some embodiments, the MK2-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension-induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation-induced fibrosis (for example, head and neck, gastrointestinal or pulmonary), primary sclerosing cholangitis, restenosis, cardiac fibrosis (for example, endomyocardial fibrosis or atrial fibrosis), opthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the MK2-mediated disease or disorder is a metabolic disorder. Exemplary metabolic disorders include obesity, steroid-resistance, glucose intolerance, and metabolic syndrome.

In some embodiments, the MK2-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the MK2-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

| Table of abbreviations. | |
|---|---|
| TFA | trifluoroacetic acid |
| TLC | thin layer chromatography |
| THF | tetrahydrofuran |
| DMF | N,N-dimethylformamide |
| EA | ethyl acetate |
| DMSO | dimethylsulfoxide |
| m-CPBA | m-chloroperoxybenzoic acid |
| DMAP | 4-dimethylaminopyridine |
| MeOH | methanol |
| PE | petroleum ether |
| h | hour |
| mins | minutes |

Example 1

Preparation of Deuterated Intermediate 1 (INT-1).

Deuterated intermediate 1 (INT-1) was prepared according to Scheme 1 below:

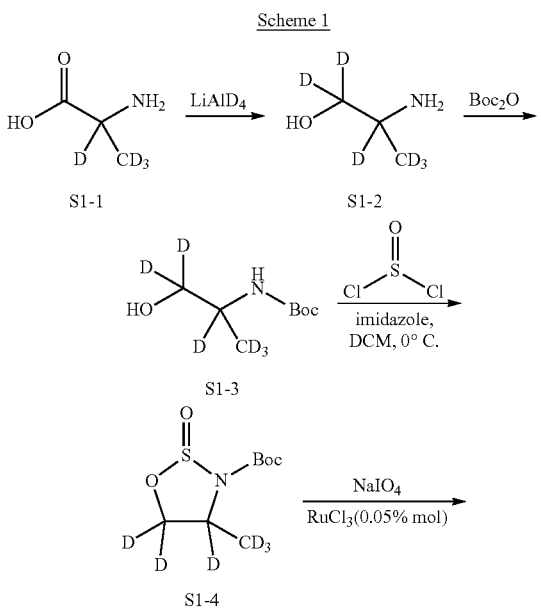

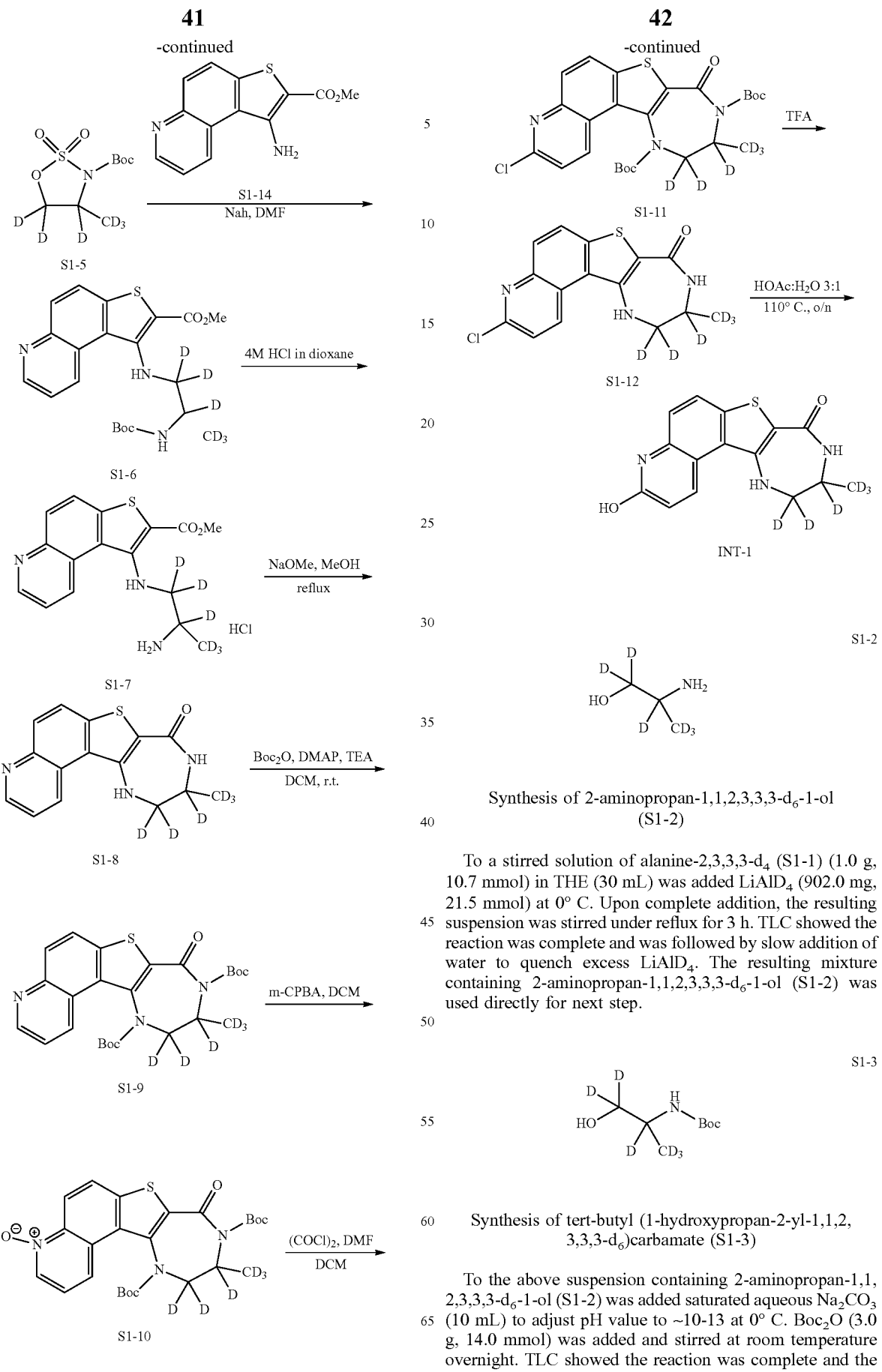

Synthesis of 2-aminopropan-1,1,2,3,3,3-$d_6$-1-ol (S1-2)

To a stirred solution of alanine-2,3,3,3-$d_4$ (S1-1) (1.0 g, 10.7 mmol) in THF (30 mL) was added LiAlD$_4$ (902.0 mg, 21.5 mmol) at 0° C. Upon complete addition, the resulting suspension was stirred under reflux for 3 h. TLC showed the reaction was complete and was followed by slow addition of water to quench excess LiAlD$_4$. The resulting mixture containing 2-aminopropan-1,1,2,3,3,3-$d_6$-1-ol (S1-2) was used directly for next step.

Synthesis of tert-butyl (1-hydroxypropan-2-yl-1,1,2,3,3,3-$d_6$)carbamate (S1-3)

To the above suspension containing 2-aminopropan-1,1,2,3,3,3-$d_6$-1-ol (S1-2) was added saturated aqueous Na$_2$CO$_3$ (10 mL) to adjust pH value to ~10-13 at 0° C. Boc$_2$O (3.0 g, 14.0 mmol) was added and stirred at room temperature overnight. TLC showed the reaction was complete and the reaction mixture was diluted with ethyl acetate (20 mL) and water (20 mL). The organic layer was separated and the aqueous layer was extracted with ethyl acetate (2×20 mL). The combined organic extracts were dried over sodium sulfate, filtered, and concentrated. Purification by flash column chromatography on silica gel (eluent:PE:EA 1:1) to afford tert-butyl (1-hydroxypropan-2-yl-1,1,2,3,3,3-d₆)carbamate (S1-3) (1.7 g, 87.5% over two steps) as a light-yellow oil.

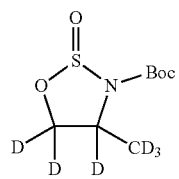

Synthesis of tert-butyl 4-(methyl-d₃)-1,2,3-oxathiazolidine-3-carboxylate-4,5,5-d₃ 2-oxide (S1-4)

To a stirred suspension of imidazole (3.9 g, 56.7 mmol) in dichloromethane (17 mL) was added a solution of thionyl chloride (1.2 mL, 17 mmol) in dichloromethane (12 mL) at 0° C. dropwise over 0.5 h. The resulting mixture was stirred at room temperature for 1 h followed by addition of a solution of tert-butyl (1-hydroxypropan-2-yl-1,1,2,3,3,3-d₆) carbamate (S1-3) (1.7 g, 9.4 mmol) in dichloromethane (17 mL) dropwise 0° C. The cooling bath was removed and the reaction mixture was stirred at room temperature for 10 mins. Aqueous citric acid (68 mL, 10 w/w %) was added and stirred for 15 min. The organic phase was separated, washed with saturated brine, dried over anhydrous sodium sulfate, and filtered and concentrated. The mixture was purified by column chromatography (eluent:PE:EA 5:1) to obtain tert-butyl 4-(methyl-d₃)-1,2,3-oxathiazolidine-3-carboxylate-4,5,5-d₃ 2-oxide (S1-4) (1.7 g, 79.8%) as a colorless oil. ¹H NMR: (300 MHz, CDCl₃) δ 1.53 (s, 9H).

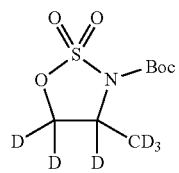

Synthesis of tert-butyl 4-(methyl-d₃)-1,2,3-oxathiazolidine-3-carboxylate-4,5,5-d₃ 2,2-dioxide (S1-5)

To a solution of tert-butyl 4-(methyl-d₃)-1,2,3-oxathiazolidine-3-carboxylate-4,5,5-d₃ 2-oxide (S1-4) (1.7 g, 7.5 mmol) in acetonitrile (28 L) was added RuCl₃ (0.84 mg, 0.004 mmol) followed by a solution of NaIO₄ (1.6 g, 7.5 mmol) in water (16 mL). The reaction mixture was stirred at room temperature for 40 mins and then diluted by addition of dichloromethane (30 mL) and water (30 mL). The organic phase was separated, washed with brine, dried over anhydrous sodium sulfate, and concentrated. The mixture was purified by column chromatography (eluent:PE:EA 3:1) to obtain tert-butyl 4-(methyl-d₃)-1,2,3-oxathiazolidine-3-carboxylate-4,5,5-d₃ 2,2-dioxide (S1-5) (1.6 g, 87.9%) as a white solid. ¹H NMR: (300 MHz, CDCl₃) δ 1.56 (s, 9H).

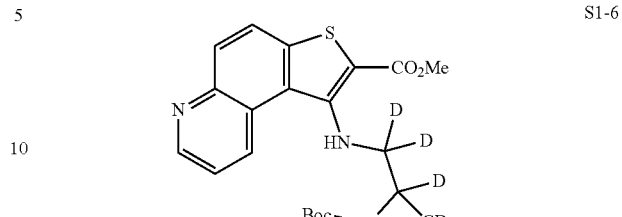

Synthesis of methyl 1-((2-((tert-butoxycarbonyl)amino)propyl-1,1,2,3,3,3-d₆)amino)thieno[3,2-f]quinoline-2-carboxylate (S1-6)

Methyl 1-((2-((tert-butoxycarbonyl)amino)propyl-1,1,2,3,3,3-d₆)amino)thieno[3,2-f]quinoline-2-carboxylate (S1-6) was prepared according to the following scheme:

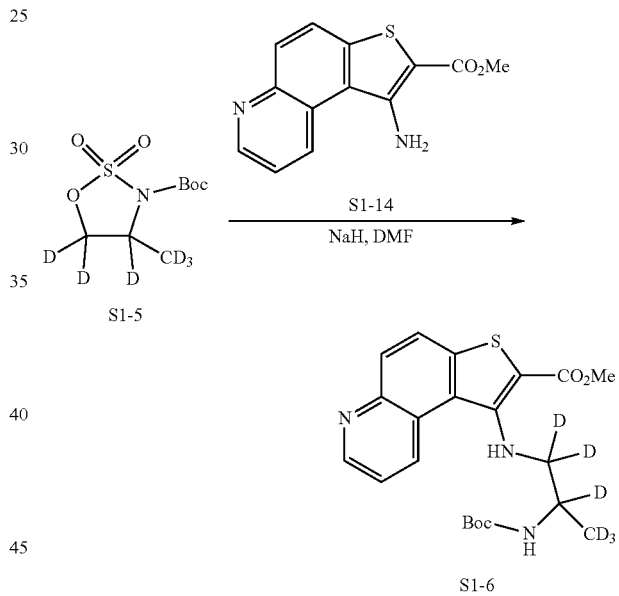

To a solution of methyl 1-aminothieno[3,2-f]quinoline-2-carboxylate (S1-14) (1.5 g, 5.8 mmol) in dry DMF (58 mL) at 0° C. was added NaH (60% in mineral oil, 278.2 mg, 7.0 mmol) portion wise over 0.5 h under nitrogen. The mixture was stirred at 0° C. for another 0.5 h followed by addition of tert-butyl 4-(methyl-d₃)-1,2,3-oxthiazolidine-3-carboxylate-4,5,5-d₃ 2,2-dioxide (S1-5) (1.4 g, 5.8 mmol) in portions over 0.5 h. Upon complete addition, TLC analysis showed that the starting material was fully consumed and formation of a less polar spot. Water (21 mL) was slowly added to the above mixture followed by aqueous HCl (1 M, 21 mL, 21 mmol). The mixture was extracted with 10% MeOH in dichloromethane, and the organic layer was separated. The aqueous layer was extracted 10% MeOH in dichloromethane (2×50 mL), and the combined organic extracts were dried over anhydrous sodium sulfate, filtered, and concentrated to give the crude material. Purification by column chromatography on silica gel (eluent: dichloromethane:MeOH 20:1) afforded methyl 1-((2-((tert-butoxycarbonyl)amino)propyl- 1,1,2,3,3,3-$d_6$)amino)thieno[3,2-f]quinoline-2-carboxylate (S1-6) (2.4 g, 90.4%) as a brown oil. MS m/z (M+H): 422.3.

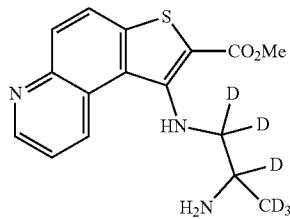

S1-7

Synthesis of methyl 1-((2-aminopropyl-1,1,2,3,3,3-$d_6$)amino)thieno[3,2-f]quinoline-2-carboxylate (S1-7)

Methyl 1-((2-((tert-butoxycarbonyl)amino)propyl-1,1,2,3,3,3-$d_6$)amino)thieno[3,2-f]quinoline-2-carboxylate (S1-6) (1.8 g, 4.3 mmol) was suspended in a stirred solution of HCl (4 M in 1,4-dioxane, 20 mL) at room temperature for 1 h. LCMS showed the reaction was complete. The resulting suspension was concentrated under reduced pressure to afford methyl 1-((2-aminopropyl-1,1,2,3,3,3-$d_6$)amino)thieno[3,2-f]quinoline-2-carboxylate (S1-7) as hydrochloride salt as a yellow solid, which was used in next step without further purification. MS m/z (M+H): 322.2.

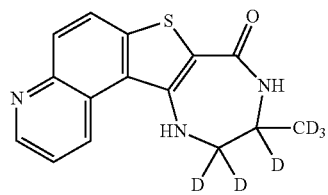

S1-8

Synthesis of 10-(methyl-$d_3$)-9,10,11,12-tetrahydro-8H-[1,4]diazepino[5',6':4,5]thieno[3,2-f]quinolin-8-one-10,11,11-$d_3$ (S1-8)

To a suspension of methyl 1-((2-aminopropyl-1,1,2,3,3,3-$d_6$)amino)thieno[3,2-f]quinoline-2-carboxylate hydrochloride (S1-7) in MeOH (60 mL) was added NaOMe (1.7 g, 30.7 mmol) at room temperature. The reaction mixture was heated at 70° C. for 3 h. LCMS and TLC showed the reaction was complete and the reaction mixture was concentrated to afford crude compound. Purification by column chromatography on silica gel (eluent:dichloromethane:MeOH 20:1) to afford 10-(methyl-d)-9,10,11,12-tetrahydro-8H-[1,4]diazepino[5',6':4,5]thieno[3,2-f]quinolin-8-one-10,11,11-$d_3$ (S1-8) (852 mg, 68.6% over two steps) as a yellow solid. MS m/z (M+H): 290.2.

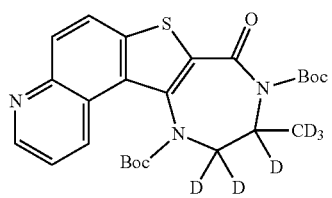

S1-9

Synthesis of di-tert-butyl 10-(methyl-$d_3$)-8-oxo-10,11-dihydro-8H-[1,4]diazepino[5',6':4,5]thieno[3,2-f]quinoline-9,12-dicarboxylate-10,11,11-$d_3$ (S1-9)

To a solution of 10-(methyl-$d_3$)-9,10,11,12-tetrahydro-8H-[1,4]diazepino[5',6':4,5]thieno[3,2-f]quinolin-8-one-10,11,11-$d_3$ (S1-8) (1.9 g, 6.6 mmol) in dichloromethane (42 mL) were added DMAP (200.7 mg, 1.6 mmol) and triethylamine (2.3 mL, 16.5 mmol). The mixture was stirred at room temperature for 10 mins followed by addition of Boc$_2$O (7.2 g, 32.9 mmol). The reaction mixture was stirred at room temperature overnight. TLC showed the reaction was complete and concentrated to give crude compound. Purification by column chromatography on silica gel (eluent: PE:EA 5:1) to afford product di-tert-butyl 10-(methyl-$d_3$)-8-oxo-10,11-dihydro-8H-[1,4]diazepino[5',6':4,5]thieno[3,2-f]quinoline-9,12-dicarboxylate-10,11,11-$d_3$ (S1-9) (2.7 g, 83.8%) as a white solid. MS m/z (M+H): 490.3.

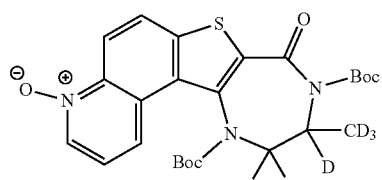

S1-10

Synthesis of 9,12-bis(tert-butoxycarbonyl)-10-(methyl-$d_3$)-8-oxo-9,10,11,12-tetrahydro-8H-[1,4]diazepino[5',6':4,5]thieno[3,2-f]quinoline 4-oxide-10,11,11-$d_3$ (S1-10)

To solution of di-tert-butyl 10-(methyl-$d_3$)-8-oxo-10,11-dihydro-8H-[1,4]diazepino[5',6':4,5]thieno[3,2-f]quinoline-9,12-dicarboxylate-10,11,11-$d_3$ (S1-9) (1.7 g, 3.5 mmol) in dichloromethane (30 mL) at 0° C. was charged with m-CPBA (1.2 g, 7.0 mmol) in portions. The reaction mixture was stirred at room temperature for 3 h. TLC showed the fully consumption of starting material. Aqueous Na$_2$SO$_3$ (20 mL, 5 w/w %) was added to quench excess oxidants. The organic phase was separated followed by saturated aqueous NaHCO$_3$ and brine wash, dried over anhydrous sodium sulfate, filtered, and concentrated to afford 9,12-bis(tert-butoxycarbonyl)-10-(methyl-d)-8-oxo-9,10,11,12-tetrahydro-8H-[1,4]diazepino[5',6':4,5]thieno[3,2-f]quinoline 4-oxide-10,11,11-$d_3$ (S1-10) as a yellow solid, which was used in the next step without further purification. MS m z (M+H): 506.4.

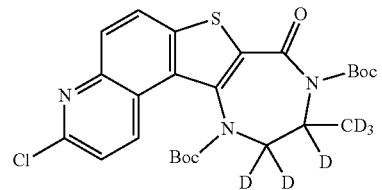

S1-11

Synthesis of di-tert-butyl 3-chloro-10-(methyl-d$_3$)-8-oxo-10,11-dihydro-8H-[1,4]diazepino[5',6':4,5]thieno[3,2-f]quinoline-9,12-dicarboxylate-10,11,11-d$_3$ (S1-11)

9,12-bis(tert-butoxycarbonyl)-10-(methyl-d$_3$)-8-oxo-9,10,11,12-tetrahydro-8H-[1,4]diazepino[5',6':4,5]thieno[3,2-f]quinoline 4-oxide-10,11,11-d$_3$ (S1-10) was dissolved in DMF (10 mL), and the mixture was cooled to 0° C. (COCl)$_2$ (192.0 mg, 1.5 mmol) was added over 1 h and stirred at room temperature for 1 h. TLC showed the reaction was complete. Water (30 mL) was added 0° C. and extracted with ethyl acetate (3×30 mL). The combined organic layer was dried over anhydrous sodium sulfate, filtered, and concentrated. Purification by column chromatography on silica gel (eluent: PE:EA 3:1) afforded di-tert-butyl 3-chloro-10-(methyl-d$_3$)-8-oxo-10,11-dihydro-8H-[1,4]diazepino[5',6':4,5]thieno[3,2-f]quinoline-9,12-dicarboxylate-10,11,11-d$_3$ (S1-11) (966 mg, 53.5%) as a white solid. MS m/z (M+H): 524.4.

S1-12

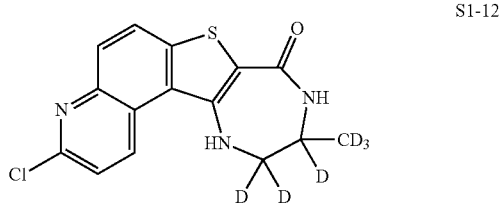 [SMILES: [2H]C([2H])([2H])C1([2H])NC(=O)c2sc3ccc4nc(Cl)ccc4c3c2NC1([2H])[2H]]

Synthesis of 3-chloro-10-(methyl-d$_3$)-9,10,11,12-tetrahydro-8H-[1,4]diazepino[5',6':4,5]thieno[3,2-f]quinolin-8-one-10,11,11-d$_3$ (S1-12)

To a solution of di-tert-butyl 3-chloro-10-(methyl-d$_3$)-8-oxo-10,11-dihydro-8H-[1,4]diazepino[5',6':4,5]thieno[3,2-f]quinoline-9,12-dicarboxylate-10,11,11-d$_3$ (S1-11) (966.0 mg, 1.8 mmol) in dichloromethane (6 mL) and TFA (2 mL) was added dropwise at 0° C. The resulting reaction mixture was stirred at room temperature for 2 h. After completion, the reaction mixture was concentrated under reduced pressure to afford 3-chloro-10-(methyl-d$_3$)-9,10,11,12-tetrahydro-8H-[1,4]diazepino[5',6':4,5]thieno[3,2-f]quinolin-8-one-10,11,11-d$_3$ (S1-12) as a brown oil, which was used in the next step without further purification. MS m/z (M+H): 324.2

INT-1

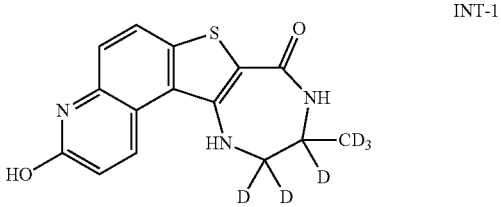 [SMILES: [2H]C([2H])([2H])C1([2H])NC(=O)c2sc3ccc4nc(O)ccc4c3c2NC1([2H])[2H]]

Synthesis of 3-hydroxy-10-(methyl-d$_3$)-9,10,11,12-tetrahydro-8H-[1,4]diazepino[5',6':4,5]thieno[3,2-f]quinolin-8-one-10,11,11-d$_3$ (INT-1)

Into a 25 mL round-bottom flask with acetic acid (12 mL) and water (6 mL) was added 3-chloro-10-(methyl-d$_3$)-9,10,11,12-tetrahydro-8H-[1,4]diazepino[5',6':4,5]thieno[3,2-f]quinolin-8-one-10,11,11-d$_3$ (S-12). The resulting suspension mixture was stirred at 110° C. for 24 hours to yield a brown solution. The resulting solution was cooled and concentrated to remove most of the solvent. Saturated ammonium hydroxide (2.0 g) was added to the residue, and precipitation was observed. Further stirring at room temperature for 1 h and filtration afforded a yellow solid. The filter cake was washed with water (3.6 mL) and dried under vacuum. The crude product was slurred with ethyl acetate (3.6 ml) for 1 hour and filtered. The solid was washed with ethyl acetate (3.6 mL), dried under vacuum at 55° C. to afford 3-hydroxy-10-(methyl-d$_3$)-9,10,11,12-tetrahydro-8H-[1,4]diazepino[5',6':4,5]thieno[3,2-f]quinolin-8-one-10,11,11-d$_3$ (INT-1) (880 mg, 97.4%). $^1$H NMR (300 MHz, DMSO-d$_6$) δ 12.1 (brs, 1H), 8.77 (d, J=9.0 Hz, 1H), 8.03 (s, 1H), 7.90 (d, J=9.0 Hz, 1H), 7.40 (d, J=9.0 Hz, 1H), 6.80 (s, 1H), 6.57 (d, J=9.0 Hz, 1H). MS m/z (M+H): 306.2.

Example 2

Preparation of 3-((2-chloro-5-(ethoxymethyl)pyrimidin-4-yl)oxy)-10-(methyl-d$_3$)-9,10,11,12-tetrahydro-8H-[1,4]diazepino[5',6':4,5]thieno[3,2-f]quinolin-8-one-10,11,11-d$_3$ (I-2)

3-((2-chloro-5-(ethoxymethyl)pyrimidin-4-yl)oxy)-10-(methyl-d)-9,10,11,12-tetrahydro-8H-[1,4]diazepino[5',6':4,5]thieno[3,2-f]quinolin-8-one-10,11,11-d$_3$ (I-2) was prepared according to Scheme 2 below.

Scheme 2.

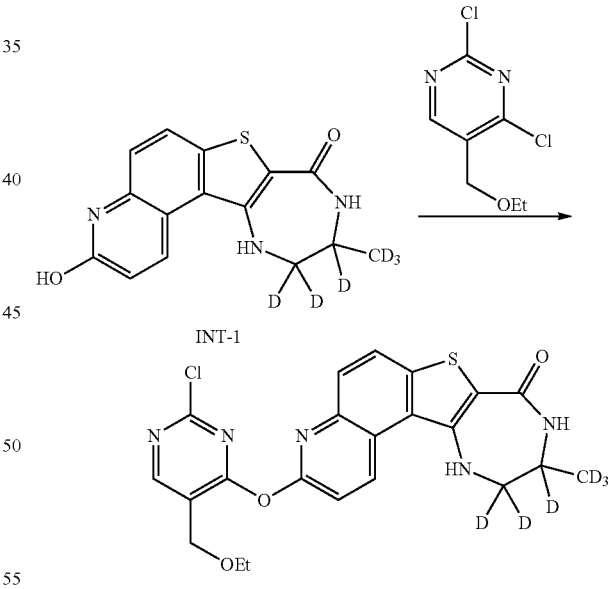

To a stirred solution of 3-hydroxy-10-(methyl-d$_3$)-9,10,11,12-tetrahydro-8H-[1,4]diazepino[5',6':4,5]thieno[3,2-f]quinolin-8-one-10,11,11-d$_3$ (INT-1) (200.0 mg, 0.6 mmol) in DMSO (4 mL) was added K$_2$CO$_3$ (180.8 mg, 1.3 mmol) and stirred at room temperature for 40 mins followed by addition of 2,4-dichloro-5-(ethoxymethyl)pyrimidine (203.4 mg, 1.0 mmol). This reaction mixture was stirred at room temperature overnight. LCMS showed the reaction was complete. The reaction mixture was passed though silica gel and purified by reverse phase prep-HPLC to afford 3-((2-chloro- 5-(ethoxymethyl)pyrimidin-4-yl)oxy)-10-(methyl-d$_3$)-9,10,11,12-tetrahydro-8H-[1,4]diazepino[5',6':4,5]thieno[3,2-f]quinolin-8-one-10,11,11-d$_3$ (I-2) (111.1 mg, 39.0%) as a yellow solid. $^1$H NMR (300 MHz, DMSO-d$_6$) δ 9.36 (d, J=9.0 Hz, 1H), 8.71 (s, 1H), 8.19 (s, J=9.0 Hz, 1H), 8.12 (s, 1H), 7.86 (d, J=9.0 Hz, 1H), 7.63 (d, J=9.0 Hz, 1H), 4.66 (s, 1H), 3.62 (dd, J=4.0 Hz, 2H), 1.20 (t, J=4.0 Hz, 3H). MS m/z (M+H): 476.3.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

ENUMERATED EMBODIMENTS

1. A compound of Formula I:

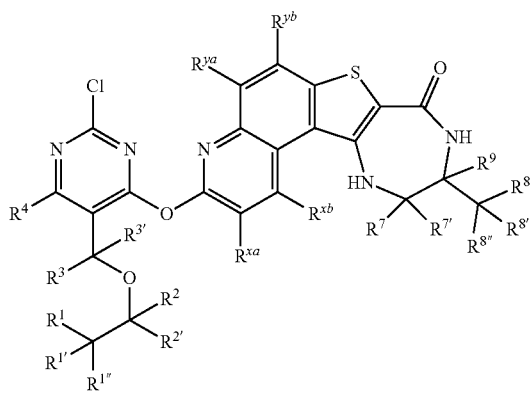

I or a pharmaceutically acceptable salt thereof, wherein:
each of R$^1$, R$^{1'}$, R$^{1''}$, R$^2$, R$^{2'}$, R$^3$, R$^{3'}$, R$^4$, R$^7$, R$^{7'}$, R$^8$, R$^{8'}$, R$^{8''}$, R$^9$, R$^{xa}$, R$^{xb}$, R$^{ya}$, and R$^{yb}$ is independently selected from hydrogen or deuterium;
provided that at least one of R$^1$, R$^{1'}$, R$^{1''}$, R$^2$, R$^{2'}$, R$^3$, R$^{3'}$, R$^4$, R$^7$, R$^{7'}$, R$^8$, R$^{8'}$, R$^{8''}$, R$^9$, R$^{xa}$, R$^{xb}$, R$^{ya}$, and R$^{yb}$ is deuterium.

2. The compound according to embodiment 1, wherein the compound is of Formulae I' or I":

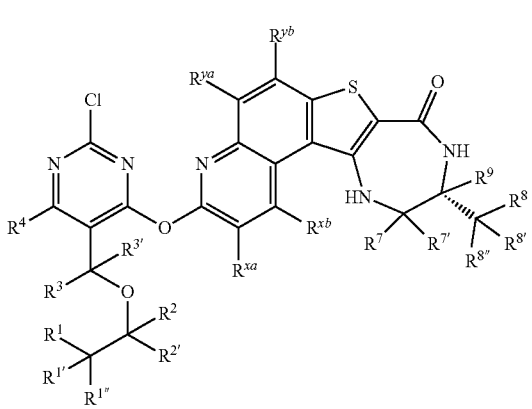

I'

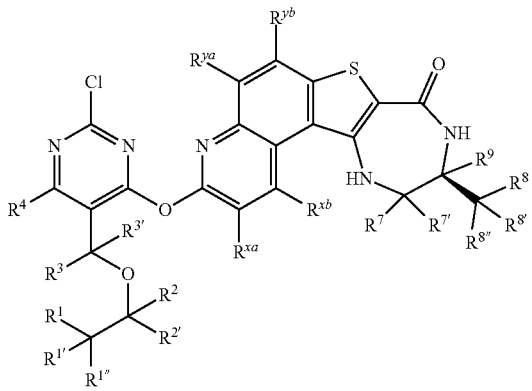

I"

or a pharmaceutically acceptable salt thereof.

3. The compound according to embodiments 1 or 2, wherein R$^1$, R$^{1'}$, R$^{1''}$ are the same.

4. The compound according to embodiments 1 or 2, wherein R$^2$, R$^{2'}$ are the same.

5. The compound according to any of embodiments 1-4, wherein each of R$^1$, R$^{1'}$, R$^{1''}$ is deuterium.

6. The compound according to any of embodiments 1-5, wherein each of R$^2$, R$^{2'}$ is deuterium.

7. The compound according to any of embodiments 1, 3, or 4, wherein each of R$^1$, R$^{1'}$, R$^{1''}$ is hydrogen.

8. The compound according to any of embodiments 1, 3, 4, or 5, wherein each of R$^2$, R$^{2'}$ is hydrogen.

9. The compound according to any of embodiments 1-8, wherein R$^7$ and R$^{7'}$ are the same.

10. The compound according to any of embodiments 1-9, wherein R$^8$, R$^{8'}$ and R$^{8''}$ are the same.

11. The compound according to any of embodiments 1-10, wherein each of R$^7$ and R$^{7'}$ is deuterium.

12. The compound according to any of embodiments 1-11, wherein each of R$^8$, R$^{8'}$ and R$^{8''}$ is deuterium.

13. The compound according to any of embodiments 1-12, wherein R$^9$ is deuterium.

14. The compound according to any of embodiments 1-10, wherein each of R$^7$ and R$^{7'}$ is hydrogen.

15. The compound according to any of embodiments 1-10 or 14, wherein each of R$^8$, R$^{8'}$, and R$^{8''}$ is hydrogen.

16. The compound according to any of embodiments 1-10, 14, or 15, wherein R$^9$ is hydrogen.

17. The compound according to any of embodiments 1-16, wherein each of R$^3$ and R$^{3'}$ is hydrogen.

18. The compound according to any of embodiments 1-16, wherein each of R$^3$ and R$^{3'}$ is deuterium.

19. The compound according to any of embodiments 1-18, wherein R$^4$ is hydrogen.

20. The compound according to any of embodiments 1-18, wherein R$^4$ is deuterium.

21. The compound according to any of embodiments 1-20, wherein each of R$^{xa}$ and R$^{xb}$ is hydrogen.

22. The compound according to any of embodiments 1-20, wherein each of R$^{xa}$ and R$^b$ is deuterium.

23. The compound according to any of embodiments 1-22, wherein each of R$^{ya}$ and R$^{yb}$ is hydrogen.

24. The compound according to any of embodiments 1-22, wherein each of R$^{ya}$ and R$^{yb}$ is deuterium.

25. The compound according to embodiment 1, wherein the compound is of Formulae II, II', or II":

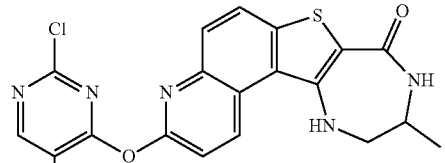

II

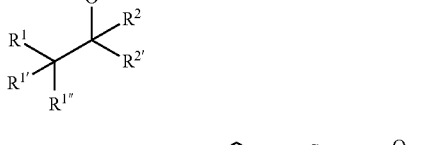

II'

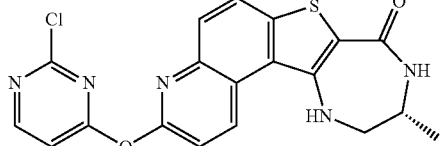

II"

or a pharmaceutically acceptable salt thereof.

26. The compound according to embodiment 25, wherein the compound is selected from:

| Formula II | Formula II' | Formula II" | R¹ | R¹' | R¹" | R² | R²' |
|---|---|---|---|---|---|---|---|
| II-1 | II'-1 | II"-1 | D | H | H | H | H |
| II-2 | II'-2 | II"-2 | H | D | H | H | H |
| II-3 | II'-3 | II"-3 | H | H | D | H | H |
| II-4 | II'-4 | II"-4 | D | D | H | H | H |
| II-5 | II'-5 | II"-5 | D | H | D | H | H |
| II-6 | II'-6 | II"-6 | H | D | D | H | H |
| II-7 | II'-7 | II"-7 | D | D | D | H | H |
| II-8 | II'-8 | II"-8 | H | H | H | H | D |
| II-9 | II'-9 | II"-9 | D | H | H | H | D |
| II-10 | II'-10 | II"-10 | H | D | H | H | D |
| II-11 | II'-11 | II"-11 | H | H | D | H | D |
| II-12 | II'-12 | II"-12 | D | D | H | H | D |
| II-13 | II'-13 | II"-13 | D | H | D | H | D |
| II-14 | II'-14 | II"-14 | H | D | D | H | D |
| II-15 | II'-15 | II"-15 | D | D | D | H | D |
| II-16 | II'-16 | II"-16 | H | H | H | D | H |
| II-17 | II'-17 | II"-17 | D | H | H | D | H |
| II-18 | II'-18 | II"-18 | H | D | H | D | H |
| II-19 | II'-19 | II"-19 | H | H | D | D | H |
| II-20 | II'-20 | II"-20 | D | D | H | D | H |
| II-21 | II'-21 | II"-21 | D | H | D | D | H |
| II-22 | II'-22 | II"-22 | H | D | D | D | H |
| II-23 | II'-23 | II"-23 | D | D | D | D | H |
| II-24 | II'-24 | II"-24 | H | H | H | D | D |
| II-25 | II'-25 | II"-25 | D | H | H | D | D |
| II-26 | II'-26 | II"-26 | H | D | H | D | D |
| II-27 | II'-27 | II"-27 | H | H | D | D | D |
| II-28 | II'-28 | II"-28 | D | D | H | D | D |
| II-29 | II'-29 | II"-29 | D | H | D | D | D |
| II-30 | II'-30 | II"-30 | H | D | D | D | D |
| II-31 | II'-31 | II"-31 | D | D | D | D | D. |

27. The compound according to embodiment 1, wherein the compound is of Formulae III, III', or III":

III

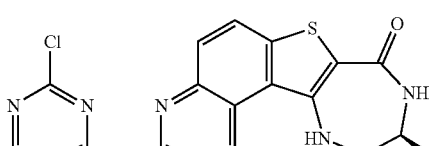

III'

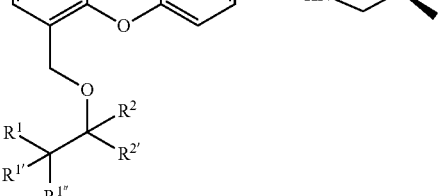

III"

or a pharmaceutically acceptable salt thereof.

28. The compound according to embodiment 27, wherein the compound is selected from:

| Formula III | Formula III' | Formula III" | R¹/R¹'/R¹" | R²/R²' | R³/R³' | R⁴ |
|---|---|---|---|---|---|---|
| III-1 | III'-1 | III"-1 | D | H | H | H |
| III-2 | III'-2 | III"-2 | H | D | H | H |
| III-3 | III'-3 | III"-3 | H | H | D | H |
| III-4 | III'-4 | III"-4 | D | D | H | H |
| III-5 | III'-5 | III"-5 | D | H | D | H |
| III-6 | III'-6 | III"-6 | H | D | D | H |
| III-7 | III'-7 | III"-7 | D | D | D | H |
| III-8 | III'-8 | III"-8 | H | H | H | D |
| III-9 | III'-9 | III"-9 | D | H | H | D |
| III-10 | III'-10 | III"-10 | H | D | H | D |
| III-11 | III'-11 | III"-11 | H | H | D | D |
| III-12 | III'-12 | III"-12 | D | D | H | D |
| III-13 | III'-13 | III"-13 | D | H | D | D |
| III-14 | III'-14 | III"-14 | H | D | D | D |
| III-15 | III'-15 | III"-15 | D | D | D | D. |

29. The compound according to embodiment 1, wherein the compound is of Formulae IV, IV', or IV":

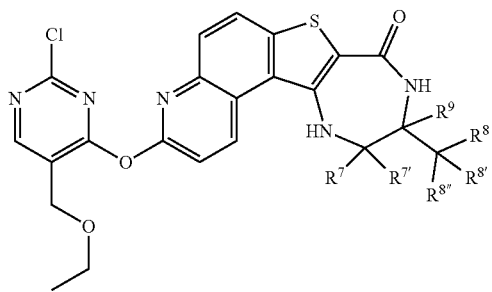

IV

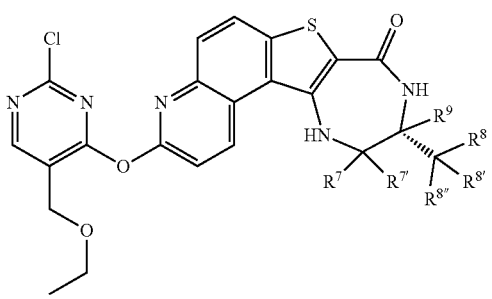

IV'

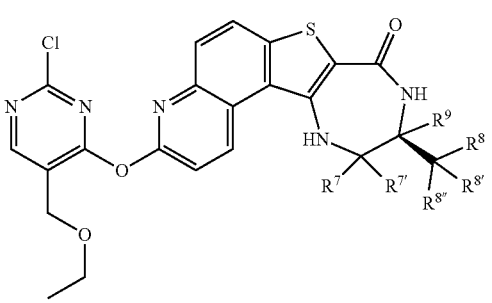

IV"

or a pharmaceutically acceptable salt thereof.

30. The compound according to embodiment 29, wherein the compound is selected from:

| Formula IV | Formula IV' | Formula IV" | R⁷ | R⁷' | R⁸ | R⁸' | R⁸" | R⁹ |
|---|---|---|---|---|---|---|---|---|
| IV-1 | IV'-1 | IV"-1 | H | H | D | H | H | H |
| IV-2 | IV'-2 | IV"-2 | H | H | H | D | H | H |
| IV-3 | IV'-3 | IV"-3 | H | H | H | H | D | H |
| IV-4 | IV'-4 | IV"-4 | H | H | D | D | H | H |
| IV-5 | IV'-5 | IV"-5 | H | H | D | H | D | H |
| IV-6 | IV'-6 | IV"-6 | H | H | H | D | D | H |
| IV-7 | IV'-7 | IV"-7 | H | H | D | D | D | H |
| IV-8 | IV'-8 | IV"-8 | H | D | H | H | H | H |
| IV-9 | IV'-9 | IV"-9 | H | D | D | H | H | H |
| IV-10 | IV'-10 | IV"-10 | H | D | H | D | H | H |
| IV-11 | IV'-11 | IV"-11 | H | D | H | H | D | H |
| IV-12 | IV'-12 | IV"-12 | H | D | D | D | H | H |
| IV-13 | IV'-13 | IV"-13 | H | D | D | H | D | H |
| IV-14 | IV'-14 | IV"-14 | H | D | H | D | D | H |
| IV-15 | IV'-15 | IV"-15 | H | D | D | D | D | H |
| IV-16 | IV'-16 | IV"-16 | D | H | H | H | H | H |
| IV-17 | IV'-17 | IV"-17 | D | H | D | H | H | H |
| IV-18 | IV'-18 | IV"-18 | D | H | H | D | H | H |
| IV-19 | IV'-19 | IV"-19 | D | H | H | H | D | H |
| IV-20 | IV'-20 | IV"-20 | D | H | D | D | H | H |
| IV-21 | IV'-21 | IV"-21 | D | H | D | H | D | H |
| IV-22 | IV'-22 | IV"-22 | D | H | H | D | D | H |
| IV-23 | IV'-23 | IV"-23 | D | H | D | D | D | H |
| IV-24 | IV'-24 | IV"-24 | D | D | H | H | H | H |
| IV-25 | IV'-25 | IV"-25 | D | D | D | H | H | H |
| IV-26 | IV'-26 | IV"-26 | D | D | H | D | H | H |
| IV-27 | IV'-27 | IV"-27 | D | D | H | H | D | H |
| IV-28 | IV'-28 | IV"-28 | D | D | D | D | H | H |
| IV-29 | IV'-29 | IV"-29 | D | D | D | H | D | H |
| IV-30 | IV'-30 | IV"-30 | D | D | H | D | D | H |
| IV-31 | IV'-31 | IV"-31 | D | D | D | D | D | H |
| IV-32 | IV'-32 | IV"-32 | H | H | H | H | H | D |
| IV-33 | IV'-33 | IV"-33 | H | H | D | H | H | D |
| IV-34 | IV'-34 | IV"-34 | H | H | H | D | H | D |
| IV-35 | IV'-35 | IV"-35 | H | H | H | H | D | D |
| IV-36 | IV'-36 | IV"-36 | H | H | D | D | H | D |
| IV-37 | IV'-37 | IV"-37 | H | H | D | H | D | D |
| IV-38 | IV'-38 | IV"-38 | H | H | H | D | D | D |
| IV-39 | IV'-39 | IV"-39 | H | H | D | D | D | D |
| IV-40 | IV'-40 | IV"-40 | H | D | H | H | H | D |
| IV-41 | IV'-41 | IV"-41 | H | D | D | H | H | D |
| IV-42 | IV'-42 | IV"-42 | H | D | H | D | H | D |
| IV-43 | IV'-43 | IV"-43 | H | D | H | H | D | D |
| IV-44 | IV'-44 | IV"-44 | H | D | D | D | H | D |
| IV-45 | IV'-45 | IV"-45 | H | D | D | H | D | D |
| IV-46 | IV'-46 | IV"-46 | H | D | H | D | D | D |
| IV-47 | IV'-47 | IV"-47 | H | D | D | D | D | D |
| IV-48 | IV'-48 | IV"-48 | D | H | H | H | H | D |
| IV-49 | IV'-49 | IV"-49 | D | H | D | H | H | D |
| IV-50 | IV'-50 | IV"-50 | D | H | H | D | H | D |
| IV-51 | IV'-51 | IV"-51 | D | H | H | H | D | D |
| IV-52 | IV'-52 | IV"-52 | D | H | D | D | H | D |
| IV-53 | IV'-53 | IV"-53 | D | H | D | H | D | D |
| IV-54 | IV'-54 | IV"-54 | D | H | H | D | D | D |
| IV-55 | IV'-55 | IV"-55 | D | H | D | D | D | D |
| IV-56 | IV'-56 | IV"-56 | D | D | H | H | H | D |
| IV-57 | IV'-57 | IV"-57 | D | D | D | H | H | D |
| IV-58 | IV'-58 | IV"-58 | D | D | H | D | H | D |
| IV-59 | IV'-59 | IV"-59 | D | D | H | H | D | D |
| IV-60 | IV'-60 | IV"-60 | D | D | D | D | H | D |
| IV-61 | IV'-61 | IV"-61 | D | D | D | H | D | D |
| IV-62 | IV'-62 | IV"-62 | D | D | H | D | D | D |
| IV-63 | IV'-63 | IV"-63 | D | D | D | D | D | D. |

31. The compound according to embodiment 1, wherein the compound is of Formulae V, V', or V".

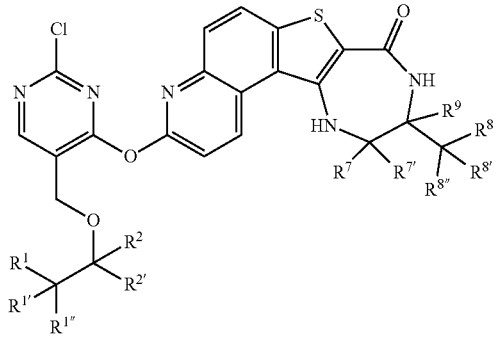

V

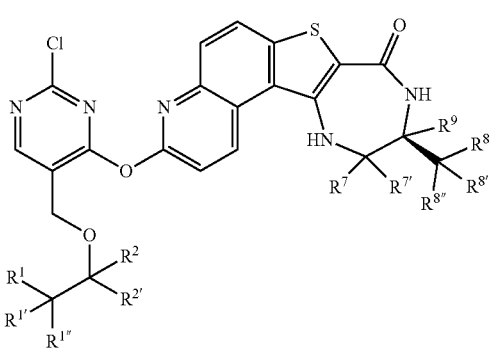

V'

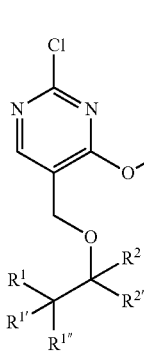

V"

or a pharmaceutically acceptable salt thereof.
32. The compound according to embodiment 31, wherein the compound is selected from:

| Formula V | Formula V' | Formula V" | R¹/R¹'/R¹" | R²/R²' | R⁷/R⁷' | R⁸/R⁸'/R⁸" | R⁹ |
|---|---|---|---|---|---|---|---|
| V-1 | V'-1 | V"-1 | D | H | D | H | H |
| V-2 | V'-2 | V"-2 | D | H | H | D | H |
| V-3 | V'-3 | V"-3 | D | H | H | H | D |
| V-4 | V'-4 | V"-4 | D | H | D | D | H |
| V-5 | V'-5 | V"-5 | D | H | D | H | D |
| V-6 | V'-6 | V"-6 | D | H | H | D | D |
| V-7 | V'-7 | V"-7 | D | H | D | D | D |
| V-8 | V'-8 | V"-8 | H | D | D | H | H |
| V-9 | V'-9 | V"-9 | H | D | H | D | H |
| V-10 | V'-10 | V"-10 | H | D | H | H | D |
| V-11 | V'-11 | V"-11 | H | D | D | D | H |
| V-12 | V'-12 | V"-12 | H | D | D | H | D |
| V-13 | V'-13 | V"-13 | H | D | H | D | D |
| V-14 | V'-14 | V"-14 | H | D | D | D | D |
| V-15 | V'-15 | V"-15 | D | D | D | H | H |
| V-16 | V'-16 | V"-16 | D | D | H | D | H |

-continued

| Formula V | Formula V' | Formula V" | R¹/R¹'/R¹" | R²/R²' | R⁷/R⁷' | R⁸/R⁸'/R⁸" | R⁹ |
|---|---|---|---|---|---|---|---|
| V-17 | V'-17 | V"-17 | D | D | H | H | D |
| V-18 | V'-18 | V"-18 | D | D | D | D | H |
| V-19 | V'-19 | V"-19 | D | D | D | H | D |
| V-20 | V'-20 | V"-20 | D | D | H | D | D |
| V-21 | V'-21 | V"-21 | D | D | D | D | D. |

33. The compound according to embodiment 1, wherein the compound is of Formulae VI,

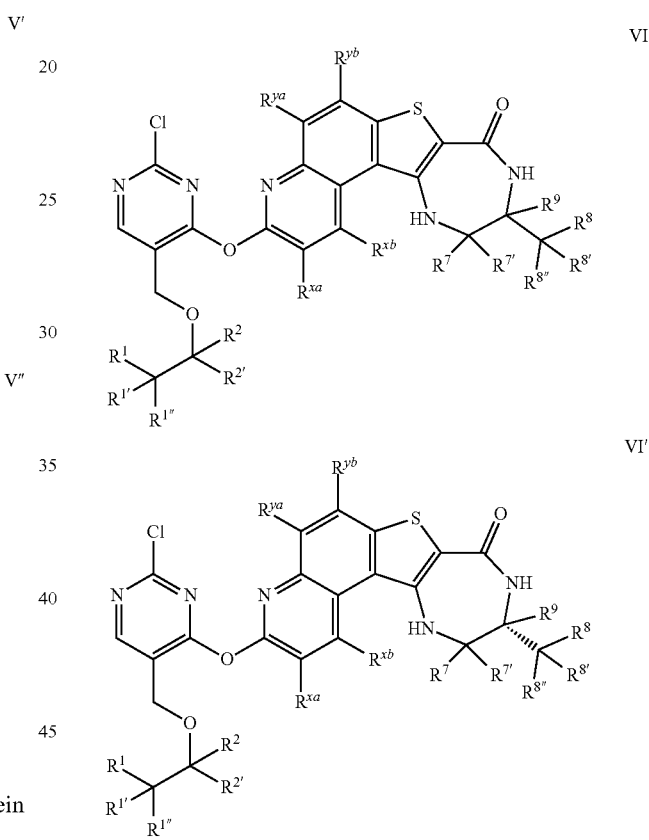

VI

VI'

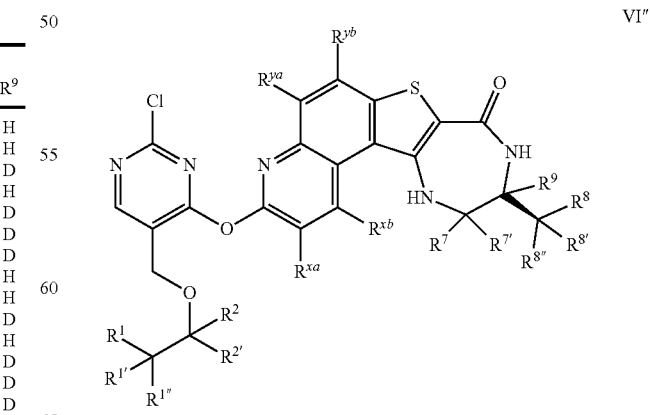

VI"

or a pharmaceutically acceptable salt thereof.

34. The compound according to embodiment 33, wherein each of $R^{ya}$ and $R^{yb}$ is hydrogen and the compound is selected from:

| Formula VI | Formula VI' | Formula VI" | $R^1/R^{1'}/R^{1"}$ | $R^2/R^{2'}/R^{2"}$ | $R^7/R^{7'}/R^{7"}$ | $R^8/R^{8'}/R^{8"}$ | $R^9$ | $R^{xa}$ | $R^{xb}$ |
|---|---|---|---|---|---|---|---|---|---|
| VI-1 | VI'-1 | VI"-1 | H | H | H | H | H | H | D |
| VI-2 | VI'-2 | VI"-2 | H | H | H | H | D | H | D |
| VI-3 | VI'-3 | VI"-3 | H | H | H | D | H | H | D |
| VI-4 | VI'-4 | VI"-4 | H | H | H | D | D | H | D |
| VI-5 | VI'-5 | VI"-5 | H | H | D | H | H | H | D |
| VI-6 | VI'-6 | VI"-6 | H | H | D | H | D | H | D |
| VI-7 | VI'-7 | VI"-7 | H | H | D | D | H | H | D |
| VI-8 | VI'-8 | VI"-8 | H | H | D | D | D | H | D |
| VI-9 | VI'-9 | VI"-9 | H | D | H | H | H | H | D |
| VI-10 | VI'-10 | VI"-10 | H | D | H | H | D | H | D |
| VI-11 | VI'-11 | VI"-11 | H | D | H | D | H | H | D |
| VI-12 | VI'-12 | VI"-12 | H | D | H | D | D | H | D |
| VI-13 | VI'-13 | VI"-13 | H | D | D | H | H | H | D |
| VI-14 | VI'-14 | VI"-14 | H | D | D | H | D | H | D |
| VI-15 | VI'-15 | VI"-15 | H | D | D | D | H | H | D |
| VI-16 | VI'-16 | VI"-16 | H | D | D | D | D | H | D |
| VI-17 | VI'-17 | VI"-17 | D | H | H | H | H | H | D |
| VI-18 | VI'-18 | VI"-18 | D | H | H | H | D | H | D |
| VI-19 | VI'-19 | VI"-19 | D | H | H | D | H | H | D |
| VI-20 | VI'-20 | VI"-20 | D | H | H | D | D | H | D |
| VI-21 | VI'-21 | VI"-21 | D | H | D | H | H | H | D |
| VI-22 | VI'-22 | VI"-22 | D | H | D | H | D | H | D |
| VI-23 | VI'-23 | VI"-23 | D | H | D | D | H | H | D |
| VI-24 | VI'-24 | VI"-24 | D | H | D | D | D | H | D |
| VI-25 | VI'-25 | VI"-25 | D | D | H | H | H | H | D |
| VI-26 | VI'-26 | VI"-26 | D | D | H | H | D | H | D |
| VI-27 | VI'-27 | VI"-27 | D | D | H | D | H | H | D |
| VI-28 | VI'-28 | VI"-28 | D | D | H | D | D | H | D |
| VI-29 | VI'-29 | VI"-29 | D | D | D | H | H | H | D |
| VI-30 | VI'-30 | VI"-30 | D | D | D | H | D | H | D |
| VI-31 | VI'-31 | VI"-31 | D | D | D | D | H | H | D |
| VI-32 | VI'-32 | VI"-32 | D | D | D | D | D | H | D |
| VI-33 | VI'-33 | VI"-33 | H | H | H | H | H | D | H |
| VI-34 | VI'-34 | VI"-34 | H | H | H | H | D | D | H |
| VI-35 | VI'-35 | VI"-35 | H | H | H | D | H | D | H |
| VI-36 | VI'-36 | VI"-36 | H | H | H | D | D | D | H |
| VI-37 | VI'-37 | VI"-37 | H | H | D | H | H | D | H |
| VI-38 | VI'-38 | VI"-38 | H | H | D | H | D | D | H |
| VI-39 | VI'-39 | VI"-39 | H | H | D | D | H | D | H |
| VI-40 | VI'-40 | VI"-40 | H | H | D | D | D | D | H |
| VI-41 | VI'-41 | VI"-41 | H | D | H | H | H | D | H |
| VI-42 | VI'-42 | VI"-42 | H | D | H | H | D | D | H |
| VI-43 | VI'-43 | VI"-43 | H | D | H | D | H | D | H |
| VI-44 | VI'-44 | VI"-44 | H | D | H | D | D | D | H |
| VI-45 | VI'-45 | VI"-45 | H | D | D | H | H | D | H |
| VI-46 | VI'-46 | VI"-46 | H | D | D | H | D | D | H |
| VI-47 | VI'-47 | VI"-47 | H | D | D | D | H | D | H |
| VI-48 | VI'-48 | VI"-48 | H | D | D | D | D | D | H |
| VI-49 | VI'-49 | VI"-49 | D | H | H | H | H | D | H |
| VI-50 | VI'-50 | VI"-50 | D | H | H | H | D | D | H |
| VI-51 | VI'-51 | VI"-51 | D | H | H | D | H | D | H |
| VI-52 | VI'-52 | VI"-52 | D | H | H | D | D | D | H |
| VI-53 | VI'-53 | VI"-53 | D | H | D | H | H | D | H |
| VI-54 | VI'-54 | VI"-54 | D | H | D | H | D | D | H |
| VI-55 | VI'-55 | VI"-55 | D | H | D | D | H | D | H |
| VI-56 | VI'-56 | VI"-56 | D | H | D | D | D | D | H |
| VI-57 | VI'-57 | VI"-57 | D | D | H | H | H | D | H |
| VI-58 | VI'-58 | VI"-58 | D | D | H | H | D | D | H |
| VI-59 | VI'-59 | VI"-59 | D | D | H | D | H | D | H |
| VI-60 | VI'-60 | VI"-60 | D | D | H | D | D | D | H |
| VI-61 | VI'-61 | VI"-61 | D | D | D | H | H | D | H |
| VI-62 | VI'-62 | VI"-62 | D | D | D | H | D | D | H |
| VI-63 | VI'-63 | VI"-63 | D | D | D | D | H | D | H |
| VI-64 | VI'-64 | VI"-64 | D | D | D | D | D | D | H |
| VI-65 | VI'-65 | VI"-65 | H | H | H | H | H | D | D |
| VI-66 | VI'-66 | VI"-66 | H | H | H | H | D | D | D |
| VI-67 | VI'-67 | VI"-67 | H | H | H | D | H | D | D |
| VI-68 | VI'-68 | VI"-68 | H | H | H | D | D | D | D |
| VI-69 | VI'-69 | VI"-69 | H | H | D | H | H | D | D |
| VI-70 | VI'-70 | VI"-70 | H | H | D | H | D | D | D |
| VI-71 | VI'-71 | VI"-71 | H | H | D | D | H | D | D |
| VI-72 | VI'-72 | VI"-72 | H | H | D | D | D | D | D |
| VI-73 | VI'-73 | VI"-73 | H | D | H | H | H | D | D |
| VI-74 | VI'-74 | VI"-74 | H | D | H | H | D | D | D |
| VI-75 | VI'-75 | VI"-75 | H | D | H | D | H | D | D |
| VI-76 | VI'-76 | VI"-76 | H | D | H | D | D | D | D |
| VI-77 | VI'-77 | VI"-77 | H | D | D | H | H | D | D |
| VI-78 | VI'-78 | VI"-78 | H | D | D | H | D | D | D |
| VI-79 | VI'-79 | VI"-79 | H | D | D | D | H | D | D |
| VI-80 | VI'-80 | VI"-80 | H | D | D | D | D | D | D |
| VI-81 | VI'-81 | VI"-81 | D | H | H | H | H | D | D |
| VI-82 | VI'-82 | VI"-82 | D | H | H | H | D | D | D |
| VI-83 | VI'-83 | VI"-83 | D | H | H | D | H | D | D |
| VI-84 | VI'-84 | VI"-84 | D | H | H | D | D | D | D |
| VI-85 | VI'-85 | VI"-85 | D | H | D | H | H | D | D |
| VI-86 | VI'-86 | VI"-86 | D | H | D | H | D | D | D |
| VI-87 | VI'-87 | VI"-87 | D | H | D | D | H | D | D |
| VI-88 | VI'-88 | VI"-88 | D | H | D | D | D | D | D |
| VI-89 | VI'-89 | VI"-89 | D | D | H | H | H | D | D |
| VI-90 | VI'-90 | VI"-90 | D | D | H | H | D | D | D |
| VI-91 | VI'-91 | VI"-91 | D | D | H | D | H | D | D |
| VI-92 | VI'-92 | VI"-92 | D | D | H | D | D | D | D |
| VI-93 | VI'-93 | VI"-93 | D | D | D | H | H | D | D |
| VI-94 | VI'-94 | VI"-94 | D | D | D | H | D | D | D |
| VI-95 | VI'-95 | VI"-95 | D | D | D | D | H | D | D |
| VI-96 | VI'-96 | VI"-96 | D | D | D | D | D | D | D. |

35. The compound according to embodiment 33, wherein each of $R^{ya}$ and $R^{yb}$ is deuterium and the compound is selected from:

| Formula VI | Formula VI' | Formula VI" | $R^1/R^{1'}/R^{1"}$ | $R^2/R^{2'}/R^{2"}$ | $R^7/R^{7'}/R^{7"}$ | $R^8/R^{8'}/R^{8"}$ | $R^9$ | $R^{xa}$ | $R^{xb}$ |
|---|---|---|---|---|---|---|---|---|---|
| VI-97 | VI'-97 | VI"-97 | H | H | H | H | H | H | H |
| VI-98 | VI'-98 | VI"-98 | H | H | H | H | D | H | H |
| VI-99 | VI'-99 | VI"-99 | H | H | H | D | H | H | H |
| VI-100 | VI'-100 | VI"-100 | H | H | H | D | D | H | H |
| VI-101 | VI'-101 | VI"-101 | H | H | D | H | H | H | H |
| VI-102 | VI'-102 | VI"-102 | H | H | D | H | D | H | H |
| VI-103 | VI'-103 | VI"-103 | H | H | D | D | H | H | H |
| VI-104 | VI'-104 | VI"-104 | H | H | D | D | D | H | H |
| VI-105 | VI'-105 | VI"-105 | H | D | H | H | H | H | H |
| VI-106 | VI'-106 | VI"-106 | H | D | H | H | D | H | H |
| VI-107 | VI'-107 | VI"-107 | H | D | H | D | H | H | H |
| VI-108 | VI'-108 | VI"-108 | H | D | H | D | D | H | H |
| VI-109 | VI'-109 | VI"-109 | H | D | D | H | H | H | H |
| VI-110 | VI'-110 | VI"-110 | H | D | D | H | D | H | H |
| VI-111 | VI'-111 | VI"-111 | H | D | D | D | H | H | H |
| VI-112 | VI'-112 | VI"-112 | H | D | D | D | D | H | H |
| VI-113 | VI'-113 | VI"-113 | D | H | H | H | H | H | H |
| VI-114 | VI'-114 | VI"-114 | D | H | H | H | D | H | H |
| VI-115 | VI'-115 | VI"-115 | D | H | H | D | H | H | H |
| VI-116 | VI'-116 | VI"-116 | D | H | H | D | D | H | H |
| VI-117 | VI'-117 | VI"-117 | D | H | D | H | H | H | H |
| VI-118 | VI'-118 | VI"-118 | D | H | D | H | D | H | H |
| VI-119 | VI'-119 | VI"-119 | D | H | D | D | H | H | H |
| VI-120 | VI'-120 | VI"-120 | D | H | D | D | D | H | H |
| VI-121 | VI'-121 | VI"-121 | D | D | H | H | H | H | H |
| VI-122 | VI'-122 | VI"-122 | D | D | H | H | D | H | H |
| VI-123 | VI'-123 | VI"-123 | D | D | H | D | H | H | H |
| VI-124 | VI'-124 | VI"-124 | D | D | H | D | D | H | H |
| VI-125 | VI'-125 | VI"-125 | D | D | D | H | H | H | H |
| VI-126 | VI'-126 | VI"-126 | D | D | D | H | D | H | H |
| VI-127 | VI'-127 | VI"-127 | D | D | D | D | H | H | H |
| VI-128 | VI'-128 | VI"-128 | D | D | D | D | D | H | H |
| VI-129 | VI'-129 | VI"-129 | H | H | H | H | H | H | H |
| VI-130 | VI'-130 | VI"-130 | H | H | H | H | H | H | D |
| VI-131 | VI'-131 | VI"-131 | H | H | H | H | D | H | D |
| VI-132 | VI'-132 | VI"-132 | H | H | H | D | H | H | D |
| VI-133 | VI'-133 | VI"-133 | H | H | H | D | D | H | D |
| VI-134 | VI'-134 | VI"-134 | H | H | D | H | H | H | D |
| VI-135 | VI'-135 | VI"-135 | H | H | D | H | D | H | D |
| VI-136 | VI'-136 | VI"-136 | H | H | D | D | H | H | D |
| VI-137 | VI'-137 | VI"-137 | H | H | D | D | D | H | D |
| VI-138 | VI'-138 | VI"-138 | H | D | H | H | H | H | D |
| VI-139 | VI'-139 | VI"-139 | H | D | H | H | D | H | D |

| Formula VI | Formula VI' | Formula VI" | R¹/R¹'/R¹" | R²/R²'/R² | R⁷/R⁷' | R⁸/R⁸'/R⁸" | R⁹ | R^{xa} | R^{xb} |
|---|---|---|---|---|---|---|---|---|---|
| VI-140 | VI'-140 | VI"-140 | H | D | H | H | D | H | D |
| VI-141 | VI'-141 | VI"-141 | H | D | D | D | H | H | D |
| VI-142 | VI'-142 | VI"-142 | H | D | D | H | D | H | D |
| VI-143 | VI'-143 | VI"-143 | H | D | D | D | D | H | D |
| VI-144 | VI'-144 | VI"-144 | H | D | D | D | D | H | D |
| VI-145 | VI'-145 | VI"-145 | D | H | H | H | H | H | D |
| VI-146 | VI'-146 | VI"-146 | D | H | D | H | H | H | D |
| VI-147 | VI'-147 | VI"-147 | D | H | H | D | H | H | D |
| VI-148 | VI'-148 | VI"-148 | D | H | H | H | D | H | D |
| VI-149 | VI'-149 | VI"-149 | D | H | H | D | H | H | D |
| VI-150 | VI'-150 | VI"-150 | D | H | D | H | D | H | D |
| VI-151 | VI'-151 | VI"-151 | D | H | H | D | D | H | D |
| VI-152 | VI'-152 | VI"-152 | D | H | D | D | D | H | D |
| VI-153 | VI'-153 | VI"-153 | D | D | H | H | H | H | D |
| VI-154 | VI'-154 | VI"-154 | D | D | D | H | H | H | D |
| VI-155 | VI'-155 | VI"-155 | D | D | H | D | H | H | D |
| VI-156 | VI'-156 | VI"-156 | D | D | H | H | D | H | D |
| VI-157 | VI'-157 | VI"-157 | D | D | D | D | H | H | D |
| VI-158 | VI'-158 | VI"-158 | D | D | D | H | D | H | D |
| VI-159 | VI'-159 | VI"-159 | D | D | H | D | D | H | D |
| VI-160 | VI'-160 | VI"-160 | D | D | D | D | D | H | D |
| VI-161 | VI'-161 | VI"-161 | H | H | H | H | H | D | H |
| VI-162 | VI'-162 | VI"-162 | H | H | D | H | H | D | H |
| VI-163 | VI'-163 | VI"-163 | H | H | H | D | H | D | H |
| VI-164 | VI'-164 | VI"-164 | H | H | H | H | D | D | H |
| VI-165 | VI'-165 | VI"-165 | H | H | D | D | H | D | H |
| VI-166 | VI'-166 | VI"-166 | H | H | D | H | D | D | H |
| VI-167 | VI'-167 | VI"-167 | H | H | H | D | D | D | H |
| VI-168 | VI'-168 | VI"-168 | H | H | D | D | D | D | H |
| VI-169 | VI'-169 | VI"-169 | H | D | H | H | H | D | H |
| VI-170 | VI'-170 | VI"-170 | H | D | D | H | H | D | H |
| VI-171 | VI'-171 | VI"-171 | H | D | H | D | H | D | H |
| VI-172 | VI'-172 | VI"-172 | H | D | H | H | D | D | H |
| VI-173 | VI'-173 | VI"-173 | H | D | D | D | H | D | H |
| VI-174 | VI'-174 | VI"-174 | H | D | D | H | D | D | H |
| VI-175 | VI'-175 | VI"-175 | H | D | H | D | D | D | H |
| VI-176 | VI'-176 | VI"-176 | H | D | D | D | D | D | H |
| VI-177 | VI'-177 | VI"-177 | D | H | H | H | H | D | H |
| VI-178 | VI'-178 | VI"-178 | D | H | D | H | H | D | H |
| VI-179 | VI'-179 | VI"-179 | D | H | H | D | H | D | H |
| VI-180 | VI'-180 | VI"-180 | D | H | H | H | D | D | H |
| VI-181 | VI'-181 | VI"-181 | D | H | D | D | H | D | H |
| VI-182 | VI'-182 | VI"-182 | D | H | D | H | D | D | H |
| VI-183 | VI'-183 | VI"-183 | D | H | H | D | D | D | H |
| VI-184 | VI'-184 | VI"-184 | D | H | D | D | D | D | H |
| VI-185 | VI'-185 | VI"-185 | D | D | H | H | H | D | H |
| VI-186 | VI'-186 | VI"-186 | D | D | D | H | H | D | H |
| VI-187 | VI'-187 | VI"-187 | D | D | H | D | H | D | H |
| VI-188 | VI'-188 | VI"-188 | D | D | H | H | D | D | H |
| VI-189 | VI'-189 | VI"-189 | D | D | D | D | H | D | H |
| VI-190 | VI'-190 | VI"-190 | D | D | D | H | D | D | H |
| VI-191 | VI'-191 | VI"-191 | D | D | H | D | D | D | H |
| VI-192 | VI'-192 | VI"-192 | D | D | D | D | D | D | H |
| VI-193 | VI'-193 | VI"-193 | H | H | H | H | H | H | D |
| VI-194 | VI'-194 | VI"-194 | H | H | D | H | H | H | D |
| VI-195 | VI'-195 | VI"-195 | H | H | H | D | H | H | D |
| VI-196 | VI'-196 | VI"-196 | H | H | H | H | D | H | D |
| VI-197 | VI'-197 | VI"-197 | H | H | D | D | H | H | D |
| VI-198 | VI'-198 | VI"-198 | H | H | D | H | D | H | D |
| VI-199 | VI'-199 | VI"-199 | H | H | H | D | D | H | D |
| VI-200 | VI'-200 | VI"-200 | H | H | D | D | D | H | D |
| VI-201 | VI'-201 | VI"-201 | H | D | H | H | H | H | D |
| VI-202 | VI'-202 | VI"-202 | H | D | D | H | H | H | D |
| VI-203 | VI'-203 | VI"-203 | H | D | H | D | H | H | D |
| VI-204 | VI'-204 | VI"-204 | H | D | H | H | D | H | D |
| VI-205 | VI'-205 | VI"-205 | H | D | D | D | H | H | D |
| VI-206 | VI'-206 | VI"-206 | H | D | D | H | D | H | D |
| VI-207 | VI'-207 | VI"-207 | H | D | H | D | D | H | D |
| VI-208 | VI'-208 | VI"-208 | H | D | D | D | D | H | D |
| VI-209 | VI'-209 | VI"-209 | D | H | H | H | H | H | D |
| VI-210 | VI'-210 | VI"-210 | D | H | D | H | H | H | D |
| VI-211 | VI'-211 | VI"-211 | D | H | H | D | H | H | D |
| VI-212 | VI'-212 | VI"-212 | D | H | H | H | D | H | D |
| VI-213 | VI'-213 | VI"-213 | D | H | D | D | H | H | D |
| VI-214 | VI'-214 | VI"-214 | D | H | D | H | D | H | D |
| VI-215 | VI'-215 | VI"-215 | D | H | H | D | D | H | D |
| VI-216 | VI'-216 | VI"-216 | D | H | D | D | D | D | D |
| VI-217 | VI'-217 | VI"-217 | D | D | H | H | H | D | D |
| VI-218 | VI'-218 | VI"-218 | D | D | D | H | H | D | D |
| VI-219 | VI'-219 | VI"-219 | D | D | H | D | H | D | D |
| VI-220 | VI'-220 | VI"-220 | D | D | H | H | D | D | D |
| VI-221 | VI'-221 | VI"-221 | D | D | D | D | H | D | D |
| VI-222 | VI'-222 | VI"-222 | D | D | D | H | D | D | D |
| VI-223 | VI'-223 | VI"-223 | D | D | H | D | D | D | D |
| VI-224 | VI'-224 | VI"-224 | D | D | D | D | D | D | D. |

36. The compound according to embodiment 33, wherein each of $R^{ya}$ is hydrogen and $R^{yb}$ is deuterium and the compound is selected from:

| Formula VI | Formula VI' | Formula VI" | R¹/R¹'/R¹" | R²/R²'/R² | R⁷/R⁷' | R⁸/R⁸'/R⁸" | R⁹ | R^{xa} | R^{xb} |
|---|---|---|---|---|---|---|---|---|---|
| VI-225 | VI'-225 | VI"-225 | H | H | H | H | H | H | H |
| VI-226 | VI'-226 | VI"-226 | H | H | D | H | H | H | H |
| VI-227 | VI'-227 | VI"-227 | H | H | H | D | H | H | H |
| VI-228 | VI'-228 | VI"-228 | H | H | H | H | D | H | H |
| VI-229 | VI'-229 | VI"-229 | H | H | D | D | H | H | H |
| VI-230 | VI'-230 | VI"-230 | H | H | D | H | D | H | H |
| VI-231 | VI'-231 | VI"-231 | H | H | H | D | D | H | H |
| VI-232 | VI'-232 | VI"-232 | H | H | D | D | D | H | H |
| VI-233 | VI'-233 | VI"-233 | H | D | H | H | H | H | H |
| VI-234 | VI'-234 | VI"-234 | H | D | D | H | H | H | H |
| VI-235 | VI'-235 | VI"-235 | H | D | H | D | H | H | H |
| VI-236 | VI'-236 | VI"-236 | H | D | H | H | D | H | H |
| VI-237 | VI'-237 | VI"-237 | H | D | D | D | H | H | H |
| VI-238 | VI'-238 | VI"-238 | H | D | D | H | D | H | H |
| VI-239 | VI'-239 | VI"-239 | H | D | H | D | D | H | H |
| VI-240 | VI'-240 | VI"-240 | H | D | D | D | D | H | H |
| VI-241 | VI'-241 | VI"-241 | D | H | H | H | H | H | H |
| VI-242 | VI'-242 | VI"-242 | D | H | D | H | H | H | H |
| VI-243 | VI'-243 | VI"-243 | D | H | H | D | H | H | H |
| VI-244 | VI'-244 | VI"-244 | D | H | H | H | D | H | H |
| VI-245 | VI'-245 | VI"-245 | D | H | D | D | H | H | H |
| VI-246 | VI'-246 | VI"-246 | D | H | D | H | D | H | H |
| VI-247 | VI'-247 | VI"-247 | D | H | H | D | D | H | H |
| VI-248 | VI'-248 | VI"-248 | D | H | D | D | D | H | H |
| VI-249 | VI'-249 | VI"-249 | D | D | H | H | H | H | H |
| VI-250 | VI'-250 | VI"-250 | D | D | D | H | H | H | H |
| VI-251 | VI'-251 | VI"-251 | D | D | H | D | H | H | H |
| VI-252 | VI'-252 | VI"-252 | D | D | H | H | D | H | H |
| VI-253 | VI'-253 | VI"-253 | D | D | D | D | H | H | H |
| VI-254 | VI'-254 | VI"-254 | D | D | D | H | D | H | H |
| VI-255 | VI'-255 | VI"-255 | D | D | H | D | D | H | H |
| VI-256 | VI'-256 | VI"-256 | D | D | D | D | D | H | H |
| VI-257 | VI'-257 | VI"-257 | H | H | H | H | H | H | D |
| VI-258 | VI'-258 | VI"-258 | H | H | D | H | H | H | D |
| VI-259 | VI'-259 | VI"-259 | H | H | H | D | H | H | D |
| VI-260 | VI'-260 | VI"-260 | H | H | H | H | D | H | D |
| VI-261 | VI'-261 | VI"-261 | H | H | D | D | H | H | D |
| VI-262 | VI'-262 | VI"-262 | H | H | D | H | D | H | D |
| VI-263 | VI'-263 | VI"-263 | H | H | H | D | D | H | D |
| VI-264 | VI'-264 | VI"-264 | H | H | D | D | D | H | D |
| VI-265 | VI'-265 | VI"-265 | H | D | H | H | H | H | D |
| VI-266 | VI'-266 | VI"-266 | H | D | D | H | H | H | D |
| VI-267 | VI'-267 | VI"-267 | H | D | H | D | H | H | D |
| VI-268 | VI'-268 | VI"-268 | H | D | H | H | D | H | D |
| VI-269 | VI'-269 | VI"-269 | H | D | D | D | H | H | D |
| VI-270 | VI'-270 | VI"-270 | H | D | D | H | D | H | D |
| VI-271 | VI'-271 | VI"-271 | H | D | H | D | D | H | D |
| VI-272 | VI'-272 | VI"-272 | H | D | D | D | D | H | D |
| VI-273 | VI'-273 | VI"-273 | D | H | H | H | H | H | D |
| VI-274 | VI'-274 | VI"-274 | D | H | D | H | H | H | D |
| VI-275 | VI'-275 | VI"-275 | D | H | H | D | H | H | D |
| VI-276 | VI'-276 | VI"-276 | D | H | H | H | D | H | D |
| VI-277 | VI'-277 | VI"-277 | D | H | D | D | H | H | D |
| VI-278 | VI'-278 | VI"-278 | D | H | D | H | D | H | D |
| VI-279 | VI'-279 | VI"-279 | D | H | H | D | D | H | D |
| VI-280 | VI'-280 | VI"-280 | D | H | D | D | D | H | D |
| VI-281 | VI'-281 | VI"-281 | D | D | H | H | H | H | D |

-continued

| Formula VI | Formula VI' | Formula VI" | R¹/R¹'/R¹" | R²/R²'/R²" | R⁷/R⁷'/R⁷" | R⁸/R⁸'/R⁸" | R⁹ | R$^{xa}$ | R$^{xb}$ |
|---|---|---|---|---|---|---|---|---|---|
| VI-282 | VI'-282 | VI"-282 | D | D | D | H | H | H | D |
| VI-283 | VI'-283 | VI"-283 | D | D | H | D | H | H | D |
| VI-284 | VI'-284 | VI"-284 | D | D | H | H | D | H | D |
| VI-285 | VI'-285 | VI"-285 | D | D | D | D | H | H | D |
| VI-286 | VI'-286 | VI"-286 | D | D | D | H | D | H | D |
| VI-287 | VI'-287 | VI"-287 | D | D | D | H | H | H | D |
| VI-288 | VI'-288 | VI"-288 | D | D | D | D | D | H | D |
| VI-289 | VI'-289 | VI"-289 | H | H | H | H | H | D | H |
| VI-290 | VI'-290 | VI"-290 | H | H | H | D | H | D | H |
| VI-291 | VI'-291 | VI"-291 | H | H | H | H | D | D | H |
| VI-292 | VI'-292 | VI"-292 | H | H | H | D | D | D | H |
| VI-293 | VI'-293 | VI"-293 | H | H | D | D | H | D | H |
| VI-294 | VI'-294 | VI"-294 | H | H | D | H | D | D | H |
| VI-295 | VI'-295 | VI"-295 | H | H | H | D | D | D | H |
| VI-296 | VI'-296 | VI"-296 | H | H | D | D | D | D | H |
| VI-297 | VI'-297 | VI"-297 | H | D | H | H | H | D | H |
| VI-298 | VI'-298 | VI"-298 | H | D | H | D | H | D | H |
| VI-299 | VI'-299 | VI"-299 | H | D | H | H | D | D | H |
| VI-300 | VI'-300 | VI"-300 | H | D | H | D | D | D | H |
| VI-301 | VI'-301 | VI"-301 | H | D | D | H | H | D | H |
| VI-302 | VI'-302 | VI"-302 | H | D | D | D | H | D | H |
| VI-303 | VI'-303 | VI"-303 | H | D | D | H | D | D | H |
| VI-304 | VI'-304 | VI"-304 | H | D | D | D | D | D | H |
| VI-305 | VI'-305 | VI"-305 | D | H | H | H | H | D | H |
| VI-306 | VI'-306 | VI"-306 | D | H | H | D | H | D | H |
| VI-307 | VI'-307 | VI"-307 | D | H | H | H | D | D | H |
| VI-308 | VI'-308 | VI"-308 | D | H | H | D | D | D | H |
| VI-309 | VI'-309 | VI"-309 | D | H | D | H | H | D | H |
| VI-310 | VI'-310 | VI"-310 | D | H | D | D | H | D | H |
| VI-311 | VI'-311 | VI"-311 | D | H | D | H | D | D | H |
| VI-312 | VI'-312 | VI"-312 | D | H | D | D | D | D | H |
| VI-313 | VI'-313 | VI"-313 | D | D | H | H | H | D | H |
| VI-314 | VI'-314 | VI"-314 | D | D | H | D | H | D | H |
| VI-315 | VI'-315 | VI"-315 | D | D | H | H | D | D | H |
| VI-316 | VI'-316 | VI"-316 | D | D | H | D | D | D | H |
| VI-317 | VI'-317 | VI"-317 | D | D | D | H | H | D | H |
| VI-318 | VI'-318 | VI"-318 | D | D | D | D | H | D | H |
| VI-319 | VI'-319 | VI"-319 | D | D | D | H | D | D | H |
| VI-320 | VI'-320 | VI"-320 | D | D | D | D | D | D | H |
| VI-321 | VI'-321 | VI"-321 | H | H | H | H | H | H | D |
| VI-322 | VI'-322 | VI"-322 | H | H | H | D | H | H | D |
| VI-323 | VI'-323 | VI"-323 | H | H | H | H | D | H | D |
| VI-324 | VI'-324 | VI"-324 | H | H | H | D | D | H | D |
| VI-325 | VI'-325 | VI"-325 | H | H | D | H | H | H | D |
| VI-326 | VI'-326 | VI"-326 | H | H | D | D | H | H | D |
| VI-327 | VI'-327 | VI"-327 | H | H | D | H | D | H | D |
| VI-328 | VI'-328 | VI"-328 | H | H | D | D | D | H | D |
| VI-329 | VI'-329 | VI"-329 | H | D | H | H | H | H | D |
| VI-330 | VI'-330 | VI"-330 | H | D | H | D | H | H | D |
| VI-331 | VI'-331 | VI"-331 | H | D | H | H | D | H | D |
| VI-332 | VI'-332 | VI"-332 | H | D | H | D | D | H | D |
| VI-333 | VI'-333 | VI"-333 | H | D | D | H | H | H | D |
| VI-334 | VI'-334 | VI"-334 | H | D | D | D | H | H | D |
| VI-335 | VI'-335 | VI"-335 | H | D | D | H | D | H | D |
| VI-336 | VI'-336 | VI"-336 | H | D | D | D | D | H | D |
| VI-337 | VI'-337 | VI"-337 | D | H | H | H | H | H | D |
| VI-338 | VI'-338 | VI"-338 | D | H | H | D | H | H | D |
| VI-339 | VI'-339 | VI"-339 | D | H | H | H | D | H | D |
| VI-340 | VI'-340 | VI"-340 | D | H | H | D | D | H | D |
| VI-341 | VI'-341 | VI"-341 | D | H | D | H | H | H | D |
| VI-342 | VI'-342 | VI"-342 | D | H | D | D | H | H | D |
| VI-343 | VI'-343 | VI"-343 | D | H | D | H | D | H | D |
| VI-344 | VI'-344 | VI"-344 | D | H | D | D | D | H | D |
| VI-345 | VI'-345 | VI"-345 | D | D | H | H | H | H | D |
| VI-346 | VI'-346 | VI"-346 | D | D | H | D | H | H | D |
| VI-347 | VI'-347 | VI"-347 | D | D | H | H | D | H | D |
| VI-348 | VI'-348 | VI"-348 | D | D | H | D | D | H | D |
| VI-349 | VI'-349 | VI"-349 | D | D | D | H | H | H | D |
| VI-350 | VI'-350 | VI"-350 | D | D | D | D | H | H | D |
| VI-351 | VI'-351 | VI"-351 | D | D | D | H | D | H | D |
| VI-352 | VI'-352 | VI"-352 | D | D | D | D | D | H | D. |

37. The compound according to embodiment 33, wherein each of R$^{ya}$ is deuterium and R$^{yb}$ is hydrogen and the compound is selected from:

| Formula VI | Formula VI' | Formula VI" | R¹/R¹'/R¹" | R²/R²'/R²" | R⁷/R⁷'/R⁷" | R⁸/R⁸'/R⁸" | R⁹ | R$^{xa}$ | R$^{xb}$ |
|---|---|---|---|---|---|---|---|---|---|
| VI-353 | VI'-353 | VI"-353 | H | H | D | H | H | H | H |
| VI-354 | VI'-354 | VI"-354 | H | H | H | D | H | H | H |
| VI-355 | VI'-355 | VI"-355 | H | H | H | H | D | H | H |
| VI-356 | VI'-356 | VI"-356 | H | H | H | H | D | H | H |
| VI-357 | VI'-357 | VI"-357 | H | H | D | D | H | H | H |
| VI-358 | VI'-358 | VI"-358 | H | H | D | H | D | H | H |
| VI-359 | VI'-359 | VI"-359 | H | H | H | D | D | H | H |
| VI-360 | VI'-360 | VI"-360 | H | H | D | D | D | H | H |
| VI-361 | VI'-361 | VI"-361 | H | D | H | H | H | H | H |
| VI-362 | VI'-362 | VI"-362 | H | D | H | D | H | H | H |
| VI-363 | VI'-363 | VI"-363 | H | D | H | H | D | H | H |
| VI-364 | VI'-364 | VI"-364 | H | D | H | D | D | H | H |
| VI-365 | VI'-365 | VI"-365 | H | D | D | H | H | H | H |
| VI-366 | VI'-366 | VI"-366 | H | D | D | D | H | H | H |
| VI-367 | VI'-367 | VI"-367 | H | D | D | H | D | H | H |
| VI-368 | VI'-368 | VI"-368 | H | D | D | D | D | H | H |
| VI-369 | VI'-369 | VI"-369 | D | H | H | H | H | H | H |
| VI-370 | VI'-370 | VI"-370 | D | H | H | D | H | H | H |
| VI-371 | VI'-371 | VI"-371 | D | H | H | H | D | H | H |
| VI-372 | VI'-372 | VI"-372 | D | H | H | D | D | H | H |
| VI-373 | VI'-373 | VI"-373 | D | H | D | H | H | H | H |
| VI-374 | VI'-374 | VI"-374 | D | H | D | D | H | H | H |
| VI-375 | VI'-375 | VI"-375 | D | H | D | H | D | H | H |
| VI-376 | VI'-376 | VI"-376 | D | H | D | D | D | H | H |
| VI-377 | VI'-377 | VI"-377 | D | D | H | H | H | H | H |
| VI-378 | VI'-378 | VI"-378 | D | D | H | D | H | H | H |
| VI-379 | VI'-379 | VI"-379 | D | D | H | H | D | H | H |
| VI-380 | VI'-380 | VI"-380 | D | D | H | D | D | H | H |
| VI-381 | VI'-381 | VI"-381 | D | D | D | H | H | H | H |
| VI-382 | VI'-382 | VI"-382 | D | D | D | D | H | H | H |
| VI-383 | VI'-383 | VI"-383 | D | D | D | H | D | H | H |
| VI-384 | VI'-384 | VI"-384 | D | D | D | D | D | H | H |
| VI-385 | VI'-385 | VI"-385 | H | H | H | H | H | H | D |
| VI-386 | VI'-386 | VI"-386 | H | H | H | D | H | H | D |
| VI-387 | VI'-387 | VI"-387 | H | H | H | H | D | H | D |
| VI-388 | VI'-388 | VI"-388 | H | H | H | D | D | H | D |
| VI-389 | VI'-389 | VI"-389 | H | H | D | H | H | H | D |
| VI-390 | VI'-390 | VI"-390 | H | H | D | D | H | H | D |
| VI-391 | VI'-391 | VI"-391 | H | H | D | H | D | H | D |
| VI-392 | VI'-392 | VI"-392 | H | H | D | D | D | H | D |
| VI-393 | VI'-393 | VI"-393 | H | D | H | H | H | H | D |
| VI-394 | VI'-394 | VI"-394 | H | D | H | D | H | H | D |
| VI-395 | VI'-395 | VI"-395 | H | D | H | H | D | H | D |
| VI-396 | VI'-396 | VI"-396 | H | D | H | D | D | H | D |
| VI-397 | VI'-397 | VI"-397 | H | D | D | H | H | H | D |
| VI-398 | VI'-398 | VI"-398 | H | D | D | D | H | H | D |
| VI-399 | VI'-399 | VI"-399 | H | D | D | H | D | H | D |
| VI-400 | VI'-400 | VI"-400 | H | D | D | D | D | H | D |
| VI-401 | VI'-401 | VI"-401 | D | H | H | H | H | H | D |
| VI-402 | VI'-402 | VI"-402 | D | H | H | D | H | H | D |
| VI-403 | VI'-403 | VI"-403 | D | H | H | H | D | H | D |
| VI-404 | VI'-404 | VI"-404 | D | H | H | D | D | H | D |
| VI-405 | VI'-405 | VI"-405 | D | H | D | H | H | H | D |
| VI-406 | VI'-406 | VI"-406 | D | H | D | D | H | H | D |
| VI-407 | VI'-407 | VI"-407 | D | H | D | H | D | H | D |
| VI-408 | VI'-408 | VI"-408 | D | H | D | D | D | H | D |
| VI-409 | VI'-409 | VI"-409 | D | D | H | H | H | H | D |
| VI-410 | VI'-410 | VI"-410 | D | D | H | D | H | H | D |
| VI-411 | VI'-411 | VI"-411 | D | D | H | H | D | H | D |
| VI-412 | VI'-412 | VI"-412 | D | D | H | D | D | H | D |
| VI-413 | VI'-413 | VI"-413 | D | D | D | H | H | H | D |
| VI-414 | VI'-414 | VI"-414 | D | D | D | D | H | H | D |
| VI-415 | VI'-415 | VI"-415 | D | D | D | H | D | H | D |
| VI-416 | VI'-416 | VI"-416 | D | D | D | D | D | H | D |
| VI-417 | VI'-417 | VI"-417 | H | H | H | H | H | D | H |
| VI-418 | VI'-418 | VI"-418 | H | H | H | D | H | D | H |
| VI-419 | VI'-419 | VI"-419 | H | H | H | H | D | D | H |
| VI-420 | VI'-420 | VI"-420 | H | H | H | D | D | D | H |
| VI-421 | VI'-421 | VI"-421 | H | H | D | H | H | D | H |
| VI-422 | VI'-422 | VI"-422 | H | H | D | D | H | D | H |
| VI-423 | VI'-423 | VI"-423 | H | H | D | H | D | D | H |
| VI-424 | VI'-424 | VI"-424 | H | H | D | D | D | H | H |
| VI-425 | VI'-425 | VI"-425 | H | D | H | H | H | D | H |

| Formula VI | Formula VI' | Formula VI" | R¹/R¹'/R¹" | R²/R²' | R⁷/R⁷' | R⁸/R⁸'/R⁸" | R⁹ | R^{xa} | R^{xb} |
|---|---|---|---|---|---|---|---|---|---|
| VI-426 | VI'-426 | VI"-426 | H | D | D | H | H | D | H |
| VI-427 | VI'-427 | VI"-427 | H | D | H | D | H | D | H |
| VI-428 | VI'-428 | VI"-428 | H | D | H | H | D | D | H |
| VI-429 | VI'-429 | VI"-429 | H | D | D | D | H | D | H |
| VI-430 | VI'-430 | VI"-430 | H | D | D | H | D | D | H |
| VI-431 | VI'-431 | VI"-431 | H | D | H | D | D | D | H |
| VI-432 | VI'-432 | VI"-432 | H | D | D | D | D | D | H |
| VI-433 | VI'-433 | VI"-433 | D | H | H | H | H | D | H |
| VI-434 | VI'-434 | VI"-434 | D | H | D | H | H | D | H |
| VI-435 | VI'-435 | VI"-435 | D | H | H | D | H | D | H |
| VI-436 | VI'-436 | VI"-436 | D | H | H | H | D | D | H |
| VI-437 | VI'-437 | VI"-437 | D | H | D | D | H | D | H |
| VI-438 | VI'-438 | VI"-438 | D | H | D | H | D | D | H |
| VI-439 | VI'-439 | VI"-439 | D | H | H | D | D | D | H |
| VI-440 | VI'-440 | VI"-440 | D | H | D | D | D | D | H |
| VI-441 | VI'-441 | VI"-441 | D | D | H | H | H | D | H |
| VI-442 | VI'-442 | VI"-442 | D | D | D | H | H | D | H |
| VI-443 | VI'-443 | VI"-443 | D | D | H | D | H | D | H |
| VI-444 | VI'-444 | VI"-444 | D | D | H | H | D | D | H |
| VI-445 | VI'-445 | VI"-445 | D | D | D | D | H | D | H |
| VI-446 | VI'-446 | VI"-446 | D | D | D | H | D | D | H |
| VI-447 | VI'-447 | VI"-447 | D | D | H | D | D | D | H |
| VI-448 | VI'-448 | VI"-448 | D | D | D | D | D | D | H |
| VI-449 | VI'-449 | VI"-449 | H | H | H | H | H | D | D |
| VI-450 | VI'-450 | VI"-450 | H | H | D | H | H | D | D |
| VI-451 | VI'-451 | VI"-451 | H | H | H | D | H | D | D |
| VI-452 | VI'-452 | VI"-452 | H | H | H | H | D | D | D |
| VI-453 | VI'-453 | VI"-453 | H | H | D | D | H | D | D |
| VI-454 | VI'-454 | VI"-454 | H | H | D | H | D | D | D |
| VI-455 | VI'-455 | VI"-455 | H | H | H | D | D | D | D |
| VI-456 | VI'-456 | VI"-456 | H | H | D | D | D | D | D |
| VI-457 | VI'-457 | VI"-457 | H | D | H | H | H | D | D |
| VI-458 | VI'-458 | VI"-458 | H | D | D | H | H | D | D |
| VI-459 | VI'-459 | VI"-459 | H | D | H | D | H | D | D |
| VI-460 | VI'-460 | VI"-460 | H | D | H | H | D | D | D |
| VI-461 | VI'-461 | VI"-461 | H | D | D | D | H | D | D |
| VI-462 | VI'-462 | VI"-462 | H | D | D | H | D | D | D |
| VI-463 | VI'-463 | VI"-463 | H | D | H | D | D | D | D |
| VI-464 | VI'-464 | VI"-464 | H | D | D | D | D | D | D |
| VI-465 | VI'-465 | VI"-465 | D | H | H | H | H | D | D |
| VI-466 | VI'-466 | VI"-466 | D | H | D | H | H | D | D |
| VI-467 | VI'-467 | VI"-467 | D | H | H | D | H | D | D |
| VI-468 | VI'-468 | VI"-468 | D | H | H | H | D | D | D |
| VI-469 | VI'-469 | VI"-469 | D | H | D | D | H | D | D |
| VI-470 | VI'-470 | VI"-470 | D | H | D | H | D | D | D |
| VI-471 | VI'-471 | VI"-471 | D | H | H | D | D | D | D |
| VI-472 | VI'-472 | VI"-472 | D | H | D | D | D | D | D |
| VI-473 | VI'-473 | VI"-473 | D | D | H | H | H | D | D |
| VI-474 | VI'-474 | VI"-474 | D | D | D | H | H | D | D |
| VI-475 | VI'-475 | VI"-475 | D | D | H | D | H | D | D |
| VI-476 | VI'-476 | VI"-476 | D | D | H | H | D | D | D |
| VI-477 | VI'-477 | VI"-477 | D | D | D | D | H | D | D |
| VI-478 | VI'-478 | VI"-478 | D | D | D | H | D | D | D |
| VI-479 | VI'-479 | VI"-479 | D | D | H | D | D | D | D |
| VI-480 | VI'-480 | VI"-480 | D | D | D | D | D | D | D. |

38. The compound according to embodiment 1, wherein the compound is of Formulae VII, VII', or VII":

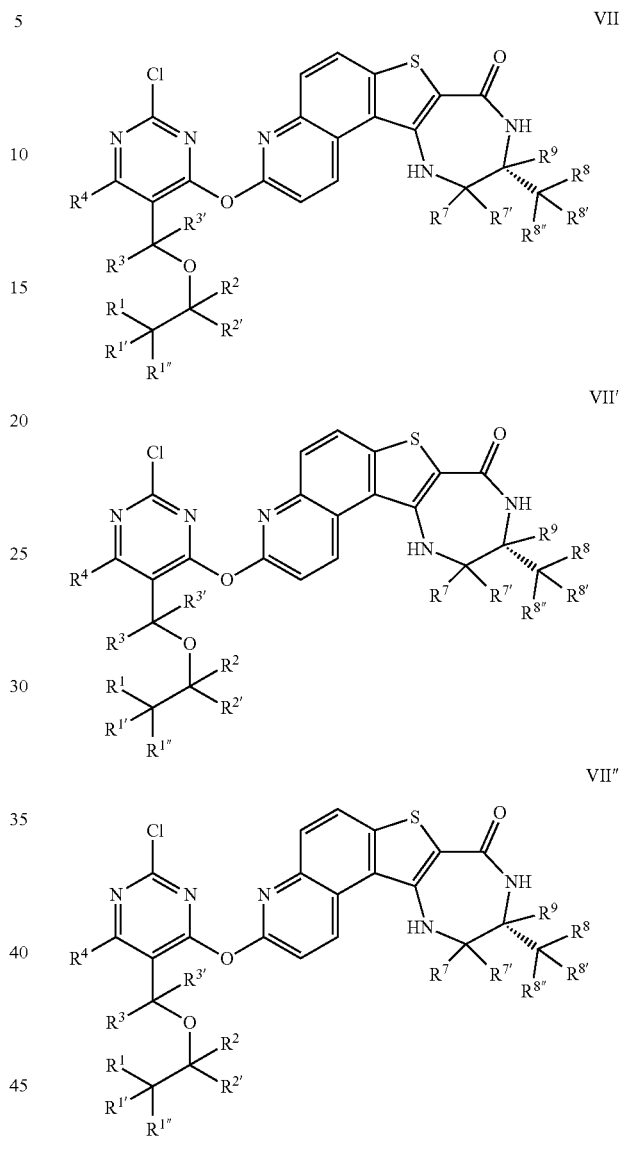

or a pharmaceutically acceptable salt thereof.

39. The compound according to embodiment 38, wherein each of R³, R³', and R⁴ are deuterium and the compound is selected from:

| Formula VII | Formula VII' | Formula VII" | R¹/R¹'/R¹" | R²/R²' | R⁷/R⁷' | R⁸/R⁸'/R⁸" | R⁹ |
|---|---|---|---|---|---|---|---|
| VII-1 | VII'-1 | VII"-1 | H | H | H | H | H |
| VII-2 | VII'-2 | VII"-2 | H | H | D | H | H |
| VII-3 | VII'-3 | VII"-3 | H | H | H | D | H |
| VII-4 | VII'-4 | VII"-4 | H | H | H | H | D |
| VII-5 | VII'-5 | VII"-5 | H | H | D | D | H |
| VII-6 | VII'-6 | VII"-6 | H | H | D | H | D |
| VII-7 | VII'-7 | VII"-7 | H | H | H | D | D |
| VII-8 | VII'-8 | VII"-8 | H | H | D | D | D |
| VII-9 | VII'-9 | VII"-9 | H | D | H | H | H |
| VII-10 | VII'-10 | VII"-10 | H | D | D | H | H |
| VII-11 | VII'-11 | VII"-11 | H | D | H | D | H |
| VII-12 | VII'-12 | VII"-12 | H | D | H | H | D |

| Formula VII | Formula VII' | Formula VII" | R¹/R¹'/R¹" | R²/R²' | R⁷/R⁷' | R⁸/R⁸'/R⁸" | R⁹ |
|---|---|---|---|---|---|---|---|
| VII-13 | VII'-13 | VII"-13 | H | D | D | D | H |
| VII-14 | VII'-14 | VII"-14 | H | D | D | H | D |
| VII-15 | VII'-15 | VII"-15 | H | D | H | D | D |
| VII-16 | VII'-16 | VII"-16 | H | D | D | D | D |
| VII-17 | VII'-17 | VII"-17 | D | H | H | H | H |
| VII-18 | VII'-18 | VII"-18 | D | H | D | H | H |
| VII-19 | VII'-19 | VII"-19 | D | H | H | D | H |
| VII-20 | VII'-20 | VII"-20 | D | H | H | H | D |
| VII-21 | VII'-21 | VII"-21 | D | H | D | D | H |
| VII-22 | VII'-22 | VII"-22 | D | H | D | H | D |
| VII-23 | VII'-23 | VII"-23 | D | H | H | D | D |
| VII-24 | VII'-24 | VII"-24 | D | H | D | D | D |
| VII-25 | VII'-25 | VII"-25 | D | D | H | H | H |
| VII-26 | VII'-26 | VII"-26 | D | D | D | H | H |
| VII-27 | VII'-27 | VII"-27 | D | D | H | D | H |
| VII-28 | VII'-28 | VII"-28 | D | D | H | H | D |
| VII-29 | VII'-29 | VII"-29 | D | D | D | D | H |
| VII-30 | VII'-30 | VII"-30 | D | D | D | H | D |
| VII-31 | VII'-31 | VII"-31 | D | D | H | D | D |
| VII-32 | VII'-32 | VII"-32 | D | D | D | D | D. |

40. The compound according to embodiment 38, wherein each of $R^3$ and $R^{3'}$ is deuterium and $R^4$ is hydrogen, and the compound is selected from:

| Formula VII | Formula VII' | Formula VII" | R¹/R¹'/R¹" | R²/R²' | R⁷/R⁷' | R⁸/R⁸'/R⁸" | R⁹ |
|---|---|---|---|---|---|---|---|
| VII-33 | VII'-33 | VII"-33 | H | H | H | H | H |
| VII-34 | VII'-34 | VII"-34 | H | H | D | H | H |
| VII-35 | VII'-35 | VII"-35 | H | H | H | D | H |
| VII-36 | VII'-36 | VII"-36 | H | H | H | H | D |
| VII-37 | VII'-37 | VII"-37 | H | H | D | D | H |
| VII-38 | VII'-38 | VII"-38 | H | H | D | H | D |
| VII-39 | VII'-39 | VII"-39 | H | H | H | D | D |
| VII-40 | VII'-40 | VII"-40 | H | H | D | D | D |
| VII-41 | VII'-41 | VII"-41 | H | D | H | H | H |
| VII-42 | VII'-42 | VII"-42 | H | D | D | H | H |
| VII-43 | VII'-43 | VII"-43 | H | D | H | D | H |
| VII-44 | VII'-44 | VII"-44 | H | D | H | H | D |
| VII-45 | VII'-45 | VII"-45 | H | D | D | D | H |
| VII-46 | VII'-46 | VII"-46 | H | D | D | H | D |
| VII-47 | VII'-47 | VII"-47 | H | D | H | D | D |
| VII-48 | VII'-48 | VII"-48 | H | D | D | D | D |
| VII-49 | VII'-49 | VII"-49 | D | H | H | H | H |
| VII-50 | VII'-50 | VII"-50 | D | H | D | H | H |
| VII-51 | VII'-51 | VII"-51 | D | H | H | D | H |
| VII-52 | VII'-52 | VII"-52 | D | H | H | H | D |
| VII-53 | VII'-53 | VII"-53 | D | H | D | D | H |
| VII-54 | VII'-54 | VII"-54 | D | H | D | H | D |
| VII-55 | VII'-55 | VII"-55 | D | H | H | D | D |
| VII-56 | VII'-56 | VII"-56 | D | H | D | D | D |
| VII-57 | VII'-57 | VII"-57 | D | D | H | H | H |
| VII-58 | VII'-58 | VII"-58 | D | D | D | H | H |
| VII-59 | VII'-59 | VII"-59 | D | D | H | D | H |
| VII-60 | VII'-60 | VII"-60 | D | D | H | H | D |
| VII-61 | VII'-61 | VII"-61 | D | D | D | D | H |
| VII-62 | VII'-62 | VII"-62 | D | D | D | H | D |
| VII-63 | VII'-63 | VII"-63 | D | D | H | D | D |
| VII-64 | VII'-64 | VII"-64 | D | D | D | D | D. |

41. The compound according to embodiment 38, wherein each of $R^3$ and $R^{3'}$ is hydrogen and $R^4$ is deuterium, and the compound is selected from:

| Formula VII | Formula VII' | Formula VII" | R¹/R¹'/R¹" | R²/R²' | R⁷/R⁷' | R⁸/R⁸'/R⁸" | R⁹ |
|---|---|---|---|---|---|---|---|
| VII-65 | VII'-65 | VII"-65 | H | H | H | H | H |
| VII-66 | VII'-66 | VII"-66 | H | H | D | H | H |
| VII-67 | VII'-67 | VII"-67 | H | H | H | D | H |
| VII-68 | VII'-68 | VII"-68 | H | H | H | H | D |
| VII-69 | VII'-69 | VII"-69 | H | H | D | D | H |
| VII-70 | VII'-70 | VII"-70 | H | H | D | H | D |
| VII-71 | VII'-71 | VII"-71 | H | H | H | D | D |
| VII-72 | VII'-72 | VII"-72 | H | H | D | D | D |
| VII-73 | VII'-73 | VII"-73 | H | D | H | H | H |
| VII-74 | VII'-74 | VII"-74 | H | D | D | H | H |
| VII-75 | VII'-75 | VII"-75 | H | D | H | D | H |
| VII-76 | VII'-76 | VII"-76 | H | D | H | H | D |
| VII-77 | VII'-77 | VII"-77 | H | D | D | D | H |
| VII-78 | VII'-78 | VII"-78 | H | D | D | H | D |
| VII-79 | VII'-79 | VII"-79 | H | D | H | D | D |
| VII-80 | VII'-80 | VII"-80 | H | D | D | D | D |
| VII-81 | VII'-81 | VII"-81 | D | H | H | H | H |
| VII-82 | VII'-82 | VII"-82 | D | H | D | H | H |
| VII-83 | VII'-83 | VII"-83 | D | H | H | D | H |
| VII-84 | VII'-84 | VII"-84 | D | H | H | H | D |
| VII-85 | VII'-85 | VII"-85 | D | H | D | D | H |
| VII-86 | VII'-86 | VII"-86 | D | H | D | H | D |
| VII-87 | VII'-87 | VII"-87 | D | H | H | D | D |
| VII-88 | VII'-88 | VII"-88 | D | H | D | D | D |
| VII-89 | VII'-89 | VII"-89 | D | D | H | H | H |
| VII-90 | VII'-90 | VII"-90 | D | D | D | H | H |
| VII-91 | VII'-91 | VII"-91 | D | D | H | D | H |
| VII-92 | VII'-92 | VII"-92 | D | D | H | H | D |
| VII-93 | VII'-93 | VII"-93 | D | D | D | D | H |
| VII-94 | VII'-94 | VII"-94 | D | D | D | H | D |
| VII-95 | VII'-95 | VII"-95 | D | D | H | D | D |
| VII-96 | VII'-96 | VII"-96 | D | D | D | D | D. |

42. The compound according to embodiment 1, wherein the compound is of Formulae VIII, VIII', or VIII":

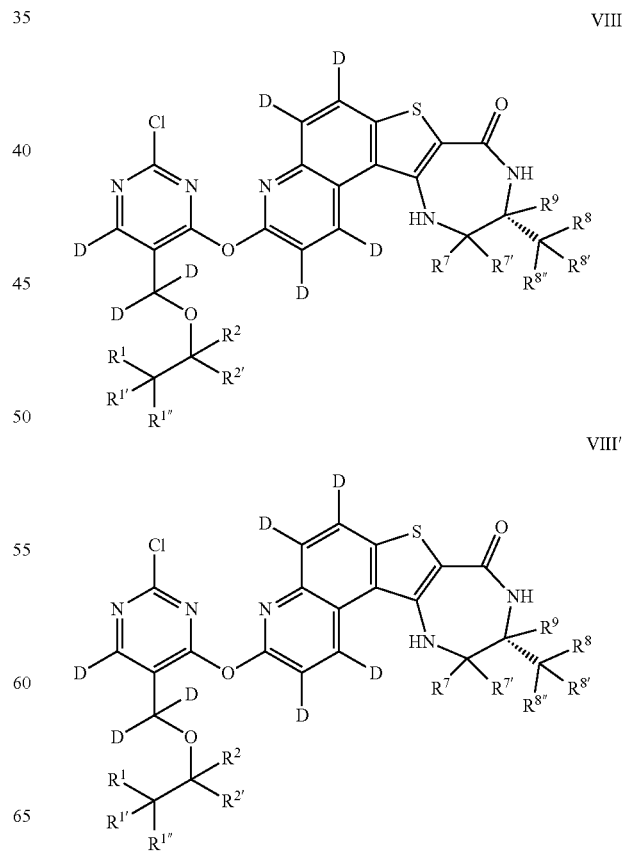

-continued

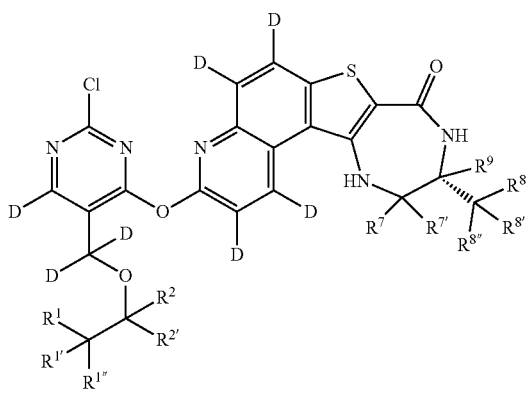

VIII"

or a pharmaceutically acceptable salt thereof 43. The compound according to embodiment 42, wherein the compound is selected from:

| Formula VIII | Formula VIII' | Formula VIII" | $R^1/R^{1'}/R^{1''}$ | $R^2/R^{2'}$ | $R^7/R^{7'}$ | $R^8/R^{8'}/R^{8''}$ | $R^9$ |
|---|---|---|---|---|---|---|---|
| VIII-1 | VIII'-1 | VIII"-1 | H | H | H | H | H |
| VIII-2 | VIII'-2 | VIII"-2 | H | H | D | H | H |
| VIII-3 | VIII'-3 | VIII"-3 | H | H | H | D | H |
| VIII-4 | VIII'-4 | VIII"-4 | H | H | H | H | D |
| VIII-5 | VIII'-5 | VIII"-5 | H | H | D | D | H |
| VIII-6 | VIII'-6 | VIII"-6 | H | H | D | H | D |
| VIII-7 | VIII'-7 | VIII"-7 | H | H | H | D | D |
| VIII-8 | VIII'-8 | VIII"-8 | H | H | D | D | D |
| VIII-9 | VIII'-9 | VIII"-9 | H | D | H | H | H |
| VIII-10 | VIII'-10 | VIII"-10 | H | D | D | H | H |
| VIII-11 | VIII'-11 | VIII"-11 | H | D | H | D | H |
| VIII-12 | VIII'-12 | VIII"-12 | H | D | H | H | D |
| VIII-13 | VIII'-13 | VIII"-13 | H | D | D | D | H |
| VIII-14 | VIII'-14 | VIII"-14 | H | D | D | H | D |
| VIII-15 | VIII'-15 | VIII"-15 | H | D | H | D | D |
| VIII-16 | VIII'-16 | VIII"-16 | H | D | D | D | D |
| VIII-17 | VIII'-17 | VIII"-17 | D | H | H | H | H |
| VIII-18 | VIII'-18 | VIII"-18 | D | H | D | H | H |
| VIII-19 | VIII'-19 | VIII"-19 | D | H | H | D | H |
| VIII-20 | VIII'-20 | VIII"-20 | D | H | H | H | D |
| VIII-21 | VIII'-21 | VIII"-21 | D | H | D | D | H |
| VIII-22 | VIII'-22 | VIII"-22 | D | H | D | H | D |
| VIII-23 | VIII'-23 | VIII"-23 | D | H | H | D | D |
| VIII-24 | VIII'-24 | VIII"-24 | D | H | D | D | D |
| VIII-25 | VIII'-25 | VIII"-25 | D | D | H | H | H |
| VIII-26 | VIII'-26 | VIII"-26 | D | D | D | H | H |
| VIII-27 | VIII'-27 | VIII"-27 | D | D | H | D | H |
| VIII-28 | VIII'-28 | VIII"-28 | D | D | H | H | D |
| VIII-29 | VIII'-29 | VIII"-29 | D | D | D | D | H |
| VIII-30 | VIII'-30 | VIII"-30 | D | D | D | H | D |
| VIII-31 | VIII'-31 | VIII"-31 | D | D | H | D | D |
| VIII-32 | VIII'-32 | VIII"-32 | D | D | D | D | D |

44. The compound according to any of embodiments 1-43, wherein the compound is other than:

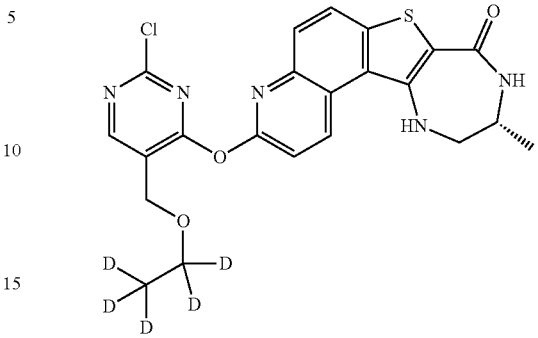

45. A pharmaceutically acceptable composition comprising the compound according to any one of embodiments 1-44 and a pharmaceutically acceptable carrier, adjuvant, or vehicle.
46. A method for inhibiting MK2 kinase, or a mutant thereof, activity in a biological sample comprising the step of contacting said biological sample with a compound according to any one of embodiments 1-44.
47. A method for inhibiting MK2 kinase, or a mutant thereof, activity in a patient comprising the step of administering to said patient the composition according to embodiment 45.
48. The method according to embodiment 47, wherein the MK2 kinase, or a mutant thereof, activity is inhibited irreversibly.
49. The method according to embodiment 48, wherein the MK2 kinase, or a mutant thereof, activity is inhibited irreversibly by covalently modifying Cys140 of MK2.
50. A method for treating an MK2-mediated disease or disorder in a patient in need thereof, comprising the step of administering to said patient the composition according to embodiment 45.
51. The method according to embodiment 50, wherein the MK2-mediated disease or disorder is an autoimmune disorder, chronic or acute inflammatory disorder, an auto-inflammatory disorder, a fibrotic disorder, a metabolic disorder, a neoplasia, or a cardiovascular or cerebrovascular disorder.
52. The method according to embodiment 51, wherein the MK2-mediated disease or disorder is an autoimmune disorder, chronic or acute inflammatory disorder, or an auto-inflammatory disorder.
53. The method according to embodiment 52, wherein the autoimmune disorder, chronic or acute inflammatory disorder, and/or auto-inflammatory disorder is selected from the group consisting of inflammatory bowel diseases, ulcerative colitis, Crohn's disease, multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic synderome, acute and chronic pancreatitis, atherosclerosis, gout, ankylosing spondylitis, fibrotic disorders, hepatic fibrosis, idiopathic pulmonary fibrosis, nephropathy, sarcoidosis, scleroderma, anaphylaxis, diabetes, diabetes mellitus type 1, diabetes mellitus type 2, diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes, temporal, Takayasu's and giant cell arteritis, Behget's disease, Wegener's granulomatosis, vitiligo, secondary hematologic manifestation of autoimmune diseases, anemias, drug-induced autoimmunity, Hashimoto's thyroiditis, hypophysitis, idiopathic thrombocytic pupura, metal-induced autoimmunity, myasthenia gravis, pemphigus, autoimmune deafness, Meniere's disease, Goodpasture's syndrome, Graves' disease, HW-related autoimmune syndromes, Gullain-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction, graft vs. host disease, allograft rejections, acute allograft rejection, chronic allograft rejection, early transplantation rejection, acute allograft rejection, reperfusion injury, pain, acute pain, chronic pain, neuropathic pain, fibromyalgia, chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

54. The method according to embodiment 47, wherein the MK2-mediated disease or disorder is a fibrotic disorder.

55. The method according to embodiment 50, wherein the fibrotic disorder is selected from the group consisting of systemic sclerosis/scleroderma, lupus nephritis, connective tissue disease, wound healing, surgical scarring, spinal cord injury, CNS scarring, acute lung injury, pulmonary fibrosis, idiopathic pulmonary fibrosis, cystic fibrosis, chronic obstructive pulmonary disease, adult respiratory distress syndrome, acute lung injury, drug-induced lung injury, glomerulonephritis, chronic kidney disease, diabetic nephropathy, hypertension-induced nephropathy, alimentary track or gastrointestinal fibrosis, renal fibrosis, hepatic or biliary fibrosis, liver fibrosis, nonalcoholic steatohepatitis, hepatitis C, hepatocellular carcinoma, cirrhosis, primary biliary cirrhosis, cirrhosis due to fatty liver disease cirrhosis due to alcoholic fatty liver disease, cirrhosis due to nonalcoholic steatosis/non-alcoholic fatty liver disease, radiation-induced fibrosis head and neck fibrosis, gastrointestinal fibrosis, pulmonary fibrosis, primary sclerosing cholangitis, restenosis, cardiac fibrosis, endomyocardial fibrosis, atrial fibrosis, opthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

56. The method according to embodiment 51, wherein the MK2-mediated disease or disorder is a metabolic disorder.

57. The method according to embodiment 56, wherein the metabolic disorder is selected from the group consisting of obesity, steroid-resistance, glucose intolerance, and metabolic syndrome.

58. The method according to embodiment 51, wherein the MK2-mediated disease or disorder is a neoplasia.

59. The method according to embodiment 58, wherein the neoplasia is selected from the group consisting of angiogenesis disorders, multiple myeloma, leukemias, acute lymphocytic leukemia, acute and chronic myelogenous leukemia, chronic lymphocytic leukemia, acute lymphoblastic leukemia, promyelocytic leukemia, lymphomas, B-cell lymphoma, T-cell lymphoma, mantle cell lymphoma, hairy cell lymphoma, Burkitt's lymphoma, mast cell tumors, Hodgkin's disease, non-Hodgkin's disease, myelodysplastic syndrome, fibrosarcoma, rhabdomyosarcoma; astrocytoma, neuroblastoma, glioma, schwannomas, melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, cancer of the bone, mouth/pharynx, esophagus, larynx, stomach, intestine, colon, rectum, lung, liver, pancreas, nerve, brain, head and neck, throat, ovary, uterus, prostate, testis, bladder, kidney, breast, gall bladder, cervix, thyroid, prostate, and skin, non-small cell lung cancer, small cell lung cancer, glioma, and glioblastoma multiforme.

60. The method according to embodiment 46 wherein the MK2-mediated disease or disorder is a cardiovascular or cerebrovascular disorder.

61. The method according to embodiment 60, wherein the cardiovascular or cerebrovascular disorder is selected from the group consisting of atherosclerosis, restenosis of an atherosclerotic coronary artery, acute coronary syndrome, myocardial infarction, cardiac-allograft vasculopathy, stroke, central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

We claim:

1. A compound of Formulae IV, IV', or IV":

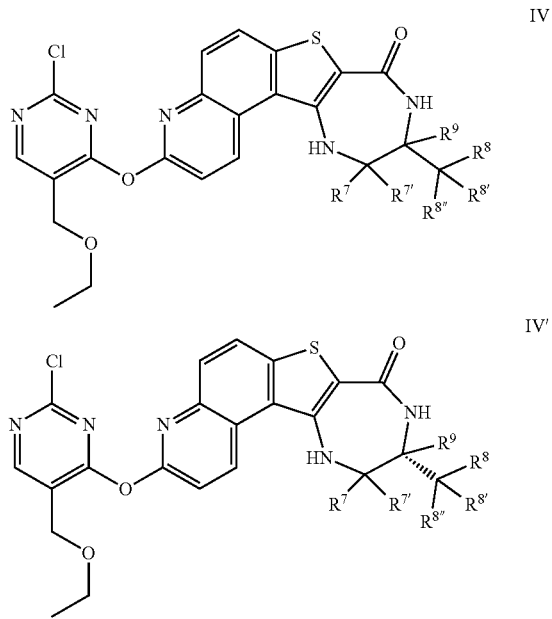

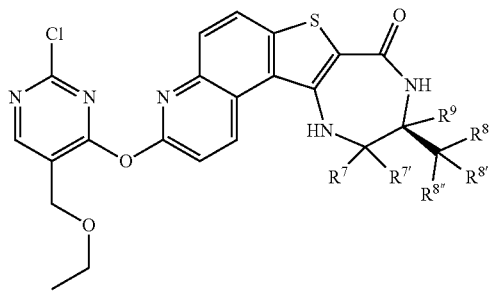

or a pharmaceutically acceptable salt thereof, whererin:
each of $R^7$, $R^{7'}$, $R^8$, $R^{8'}$, $R^{8''}$, and $R^9$ is independently selected from hydrogen or deuterium;
provided that at least one of $R^7$, $R^{7'}$, $R^8$, $R^{8'}$, $R^{8''}$, and $R^9$ is deuterium.

2. The compound according to claim 1, wherein the compound is selected from:

| Formula IV | Formula IV' | Formula IV'' | $R^7$ | $R^{7'}$ | $R^8$ | $R^{8'}$ | $R^{8''}$ | $R^9$ |
|---|---|---|---|---|---|---|---|---|
| IV-1 | IV'-1 | IV''-1 | H | H | D | H | H | H |
| IV-2 | IV'-2 | IV''-2 | H | H | H | D | H | H |
| IV-3 | IV'-3 | IV''-3 | H | H | H | H | D | H |
| IV-4 | IV'-4 | IV''-4 | H | H | D | D | H | H |
| IV-5 | IV'-5 | IV''-5 | H | H | D | H | D | H |
| IV-6 | IV'-6 | IV''-6 | H | H | H | D | D | H |
| IV-7 | IV'-7 | IV''-7 | H | H | D | D | D | H |
| IV-8 | IV'-8 | IV''-8 | H | D | H | H | H | H |
| IV-9 | IV'-9 | IV''-9 | H | D | D | H | H | H |
| IV-10 | IV'-10 | IV''-10 | H | D | H | D | H | H |
| IV-11 | IV'-11 | IV''-11 | H | D | H | H | D | H |
| IV-12 | IV'-12 | IV''-12 | H | D | D | D | H | H |
| IV-13 | IV'-13 | IV''-13 | H | D | D | H | D | H |
| IV-14 | IV'-14 | IV''-14 | H | D | H | D | D | H |
| IV-15 | IV'-15 | IV''-15 | H | D | D | D | D | H |
| IV-16 | IV'-16 | IV''-16 | D | H | H | H | H | H |
| IV-17 | IV'-17 | IV''-17 | D | H | D | H | H | H |
| IV-18 | IV'-18 | IV''-18 | D | H | H | D | H | H |
| IV-19 | IV'-19 | IV''-19 | D | H | H | H | D | H |
| IV-20 | IV'-20 | IV''-20 | D | H | D | D | H | H |
| IV-21 | IV'-21 | IV''-21 | D | H | D | H | D | H |
| IV-22 | IV'-22 | IV''-22 | D | H | H | D | D | H |
| IV-23 | IV'-23 | IV''-23 | D | H | D | D | D | H |
| IV-24 | IV'-24 | IV''-24 | D | D | H | H | H | H |
| IV-25 | IV'-25 | IV''-25 | D | D | D | H | H | H |
| IV-26 | IV'-26 | IV''-26 | D | D | H | D | H | H |
| IV-27 | IV'-27 | IV''-27 | D | D | H | H | D | H |
| IV-28 | IV'-28 | IV''-28 | D | D | D | D | H | H |
| IV-29 | IV'-29 | IV''-29 | D | D | D | H | D | H |
| IV-30 | IV'-30 | IV''-30 | D | D | H | D | D | H |
| IV-31 | IV'-31 | IV''-31 | D | D | D | D | D | H |
| IV-32 | IV'-32 | IV''-32 | H | H | H | H | H | D |
| IV-33 | IV'-33 | IV''-33 | H | H | D | H | H | D |
| IV-34 | IV'-34 | IV''-34 | H | H | H | D | H | D |
| IV-35 | IV'-35 | IV''-35 | H | H | H | H | D | D |
| IV-36 | IV'-36 | IV''-36 | H | H | D | D | H | D |
| IV-37 | IV'-37 | IV''-37 | H | H | D | H | D | D |
| IV-38 | IV'-38 | IV''-38 | H | H | H | D | D | D |
| IV-39 | IV'-39 | IV''-39 | H | H | D | D | D | D |
| IV-40 | IV'-40 | IV''-40 | H | D | H | H | H | D |
| IV-41 | IV'-41 | IV''-41 | H | D | D | H | H | D |
| IV-42 | IV'-42 | IV''-42 | H | D | H | D | H | D |
| IV-43 | IV'-43 | IV''-43 | H | D | H | H | D | D |
| IV-44 | IV'-44 | IV''-44 | H | D | D | D | H | D |
| IV-45 | IV'-45 | IV''-45 | H | D | D | H | D | D |
| IV-46 | IV'-46 | IV''-46 | H | D | H | D | D | D |
| IV-47 | IV'-47 | IV''-47 | H | D | D | D | D | D |
| IV-48 | IV'-48 | IV''-48 | D | H | H | H | H | D |
| IV-49 | IV'-49 | IV''-49 | D | H | D | H | H | D |
| IV-50 | IV'-50 | IV''-50 | D | H | H | D | H | D |
| IV-51 | IV'-51 | IV''-51 | D | H | H | H | D | D |
| IV-52 | IV'-52 | IV''-52 | D | H | D | D | H | D |
| IV-53 | IV'-53 | IV''-53 | D | H | D | H | D | D |
| IV-54 | IV'-54 | IV''-54 | D | H | H | D | D | D |
| IV-55 | IV'-55 | IV''-55 | D | H | D | D | D | D |
| IV-56 | IV'-56 | IV''-56 | D | D | H | H | H | D |
| IV-57 | IV'-57 | IV''-57 | D | D | D | H | H | D |
| IV-58 | IV'-58 | IV''-58 | D | D | H | D | H | D |
| IV-59 | IV'-59 | IV''-59 | D | D | H | H | D | D |
| IV-60 | IV'-60 | IV''-60 | D | D | D | D | H | D |
| IV-61 | IV'-61 | IV''-61 | D | D | D | H | D | D |
| IV-62 | IV'-62 | IV''-62 | D | D | H | D | D | D |
| IV-63 | IV'-63 | IV''-63 | D | D | D | D | D | D. |

3. A pharmaceutically acceptable composition comprising the compound according to any one of claims 1 and a pharmaceutically acceptable carrier, adjuvant, or vehicle.

4. A method for inhibiting MK2 kinase, or a mutant thereof, activity in a biological sample comprising the step of contacting said biological sample with a compound according to any one of claims 1.

5. A method for treating an MK2-mediated disease or disorder in a patient in need thereof, comprising the step of administering to said patient the composition according to claim 3.

6. The compound according to claim 1, wherein each of $R^7$ and $R^{7''}$ is deuterium.

7. The compound according to claim 1, wherein each of $R^8$, $R^{8'}$, and $R^{8''}$ is deuterium.

8. The compound according to claim 6, wherein each of $R^8$, $R^{8'}$, and $R^{8''}$ is deuterium.

9. The compound according to claim 7, wherein $R^9$ is deuterium.

10. The compound according to claim 6, wherein $R^9$ is deuterium.

11. The compound according to claim 7, wherein $R^9$ is deuterium.

12. The compound according to claim 1, wherein the compound is:

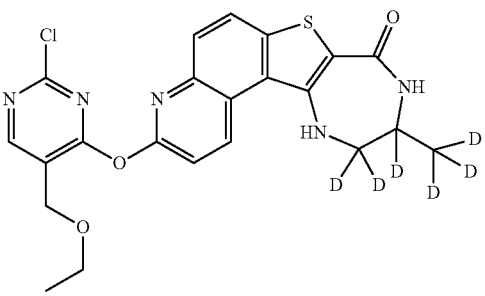

I-2 or a pharmaceutically acceptable salt thereof.

13. A pharmaceutically acceptable composition comprising the compound according to claim 12 and a pharmaceutically acceptable carrier, adjuvant, or vehicle.

* * * * *